(12) United States Patent
Soll et al.

(10) Patent No.: US 8,921,408 B2
(45) Date of Patent: Dec. 30, 2014

(54) COMPOSITIONS COMPRISING AN ARYL PYRAZOLE AND/OR A FORMAMIDINE, METHODS AND USES THEREOF

(71) Applicant: Merial Limited, Duluth, GA (US)

(72) Inventors: Mark David Soll, Alpharetta, GA (US); Luiz Gustavo Cramer, Cumming, GA (US); Patrice Wurtz, Sassenay, GA (US); James Pate, Hampton, GA (US); Natalya Shub, Allentown, PA (US); Loic Patrick Le Hir de Fallois, Atlanta, GA (US); Philip Reid Timmons, Durham, NC (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 13/901,077

(22) Filed: May 23, 2013

(65) Prior Publication Data

US 2013/0256170 A1    Oct. 3, 2013

Related U.S. Application Data

(62) Division of application No. 12/618,534, filed on Nov. 13, 2009, now Pat. No. 8,450,357.

(51) Int. Cl.
*A61K 31/415*     (2006.01)
(52) U.S. Cl.
USPC ........................... 514/407; 514/636; 514/638
(58) Field of Classification Search
USPC .......................................... 514/407, 636, 638
See application file for complete search history.

(56) References Cited

U.S. PATENT DOCUMENTS

| | | | |
|---|---|---|---|
| 3,781,355 A | 12/1973 | Harrison et al. | 260/564 |
| 3,864,497 A | 2/1975 | Harrison et al. | 424/326 |
| 3,950,360 A | 4/1976 | Aoki et al. | 549/264 |
| 4,199,569 A | 4/1980 | Chabala et al. | 514/30 |
| 4,239,774 A | 12/1980 | Kerry et al. | 424/288 |
| 4,310,519 A | 1/1982 | Albers-Schonberg et al. | 514/30 |
| 4,427,663 A | 1/1984 | Mrozik | 514/30 |
| 4,810,720 A | 3/1989 | Jensen-Korte et al. | 514/407 |
| 4,855,317 A | 8/1989 | Gehret | 514/450 |
| 4,859,657 A | 8/1989 | O'Sullivan et al. | 514/63 |
| 4,871,719 A | 10/1989 | Maienfisch | 514/63 |
| 4,874,749 A | 10/1989 | Mrozik | 514/30 |
| 4,920,148 A | 4/1990 | Gehret | 514/450 |
| 4,963,575 A | 10/1990 | Buntain et al. | 514/359 |
| 4,963,582 A | 10/1990 | Sato et al. | 514/450 |
| 4,973,711 A | 11/1990 | Maienfisch | 549/264 |
| 4,978,677 A | 12/1990 | Gehret | 514/450 |
| 5,045,536 A | 9/1991 | Baker | 514/63 |
| 5,055,596 A | 10/1991 | Baker et al. | 549/268 |
| 5,077,308 A | 12/1991 | Blizzard | 514/450 |
| 5,122,530 A | 6/1992 | Tomioka et al. | 514/341 |
| 5,223,073 A | 6/1993 | Fredi et al. | 156/381 |
| 5,232,940 A | 8/1993 | Hatton et al. | 514/407 |
| 5,236,938 A | 8/1993 | Huang et al. | 514/341 |
| 5,318,203 A | 6/1994 | Iaia | 222/94 |
| 5,353,961 A | 10/1994 | Debush | 222/94 |
| 5,547,974 A | 8/1996 | Hatton et al. | 514/406 |
| 5,567,429 A | 10/1996 | Senbo | 424/405 |
| 5,608,077 A | 3/1997 | Hatton et al. | 548/368.1 |
| 5,714,919 A | 2/1998 | Satoh et al. | 514/406 |
| 5,814,652 A | 9/1998 | Wu | 514/404 |
| 5,817,688 A | 10/1998 | Huang | 514/407 |
| D404,972 S | 2/1999 | Rodgers | D7/598 |
| 5,885,607 A | 3/1999 | Jeannin | 424/441 |
| 5,916,618 A | 6/1999 | Hatton et al. | 426/532 |
| 5,922,885 A | 7/1999 | Huang et al. | 548/370.1 |
| 5,994,386 A | 11/1999 | Huang et al. | 514/407 |
| 6,001,384 A | 12/1999 | Jeannin | 424/405 |
| 6,010,710 A | 1/2000 | Etchegaray | 424/405 |
| 6,069,157 A | 5/2000 | Banks et al. | 514/341 |
| 6,083,519 A | 7/2000 | Jeannin | 424/411 |
| 6,090,751 A | 7/2000 | Chen | 514/66 |
| 6,096,329 A | 8/2000 | Jeannin | 424/405 |
| 6,124,339 A | 9/2000 | Huang et al. | 514/407 |
| 6,161,729 A | 12/2000 | Gentile et al. | 222/94 |
| 6,180,798 B1 | 1/2001 | Huang et al. | 548/370.1 |
| 6,230,935 B1 | 5/2001 | Mack et al. | 222/137 |
| 6,260,735 B1 | 7/2001 | Fuquen | 222/94 |
| 6,337,345 B1 | 1/2002 | Fukuchi | 514/427 |
| 6,350,771 B1 | 2/2002 | Wu et al. | 514/404 |
| 6,395,765 B1 | 5/2002 | Etchegaray | 514/407 |
| 6,395,906 B1 | 5/2002 | Huang et al. | 548/370.1 |
| 6,413,542 B1 | 7/2002 | Etchegaray et al. | 424/438 |
| 6,426,333 B1 | 7/2002 | Huet et al. | 514/30 |
| 6,482,425 B1 | 11/2002 | Huet et al. | 424/406 |
| 6,534,529 B2 | 3/2003 | Uhr et al. | 514/241 |
| 6,538,013 B2 | 3/2003 | Goebel et al. | 514/357 |

(Continued)

FOREIGN PATENT DOCUMENTS

| | | | | |
|---|---|---|---|---|
| CA | 2311862 | 12/2001 | | A01N 25/00 |
| CN | 1079776 A | 12/2003 | | C11D 3/48 |

(Continued)

OTHER PUBLICATIONS

"Comparison of an amitraz-impregnated collar with topical administration of fipronil for prevention of experimental and natural infestations by the brown dog tick (Rhipicephalus sanguineus)" Estrada-Pena et al., Chemical Abstracts 1999:415153.

*Primary Examiner* — Re-tsang Shiao

(74) *Attorney, Agent, or Firm* — Judy Jarecki-Black; John Ezcurra; Merial Limited

(57) ABSTRACT

This invention relates to compositions for combating parasites in animals, comprising 1-arylpyrazole compounds alone or in combination with formamidine compounds. This invention also provides for an improved methods for eradicating, controlling, and preventing parasite infestation in an animal comprising administering the compositions of the invention to the animal in need thereof.

40 Claims, 7 Drawing Sheets

(56) References Cited

U.S. PATENT DOCUMENTS

| | | | |
|---|---|---|---|
| 6,685,954 B2 | 2/2004 | Jeannin | 424/405 |
| 6,750,230 B2 | 6/2004 | Corbau et al. | 514/326 |
| 6,883,295 B1 | 4/2005 | Negri et al. | 53/459 |
| 6,962,713 B2 | 11/2005 | Huet et al. | 424/405 |
| 6,998,131 B2 | 2/2006 | Soll et al. | 424/406 |
| 7,262,214 B2 | 8/2007 | Soll et al. | 514/407 |
| 7,345,092 B2 | 3/2008 | Cottrell et al. | 514/471 |
| 7,368,435 B2 | 5/2008 | Cottrell et al. | 514/30 |
| 7,531,186 B2 | 5/2009 | Boeckh et al. | 424/406 |
| 7,759,381 B2 | 7/2010 | Lee et al. | 514/406 |
| 8,242,161 B2 | 8/2012 | Boeckh et al. | 514/407 |
| 8,450,357 B2 * | 5/2013 | Soll et al. | 514/407 |
| 2002/0006924 A1 | 1/2002 | Uhr et al. | 514/241 |
| 2003/0203859 A1 | 10/2003 | Bruce | 424/28 |
| 2005/0020564 A1 | 1/2005 | Atkinson et al. | 514/210.2 |
| 2005/0074475 A1 | 4/2005 | Southworth | 424/405 |
| 2008/0031902 A1 | 2/2008 | Lee et al. | 424/400 |
| 2008/0194642 A1 | 8/2008 | Albright et al. | 514/341 |
| 2009/0192207 A1 | 7/2009 | Boeckh et al. | 424/406 |
| 2013/0023490 A1 | 1/2013 | Boeckh et al. | 514/30 |

FOREIGN PATENT DOCUMENTS

| | | | |
|---|---|---|---|
| EP | 0231510 | 8/1987 | |
| EP | 0234119 | 9/1987 | A01N 43/56 |
| EP | 0 295 117 A2 | 12/1988 | A01N 43/56 |
| EP | 0352944 A1 | 1/1990 | C07D 403/04 |
| EP | 0433909 | 6/1991 | A01N 47/34 |
| EP | 0500209 A1 | 8/1992 | C07D 401/04 |
| EP | 0780378 A1 | 6/1997 | C07D 231/14 |
| EP | 0846686 | 6/1998 | C07D 231/38 |
| EP | 1413201 | 4/2004 | A01N 47/34 |
| GB | 2220856 | 1/1990 | A01N 43/90 |
| JP | 53-38621 | 4/1978 | A01N 9/02 |
| JP | 53-41428 | 4/1978 | A01N 9/02 |
| JP | 54-44021 | 4/1979 | A01N 9/02 |
| JP | 54-101426 | 8/1979 | A01N 9/20 |
| JP | 10-324605 | 8/1998 | A01N 43/56 |
| WO | WO 87/03781 | 7/1987 | A01N 43/56 |
| WO | WO 98/28277 A1 | 7/1998 | C07D 231/12 |
| WO | WO 98/28278 A1 | 7/1998 | C07D 231/12 |
| WO | WO 98/39972 A1 | 9/1998 | A01N 47/02 |
| WO | WO 99/32086 | 7/1999 | A61K 9/08 |
| WO | WO 00/35844 | 6/2000 | C07C 29/141 |
| WO | WO 00/54591 | 9/2000 | A01N 47/00 |
| WO | WO 01/32663 | 5/2001 | C07D 495/04 |
| WO | WO 01/95715 A2 | 12/2001 | |
| WO | WO 02/058690 | 8/2002 | A61K 31/16 |
| WO | WO 03/015519 | 2/2003 | A01N 43/56 |
| WO | WO 03/057674 | 7/2003 | C07D 231/18 |
| WO | WO 2004/069658 | 8/2004 | B65B 9/04 |
| WO | WO 2005/094330 | 10/2005 | |
| WO | WO 2006/042099 | 4/2006 | A01N 37/52 |
| WO | WO 2008/065512 | 6/2008 | B65B 9/04 |

* cited by examiner

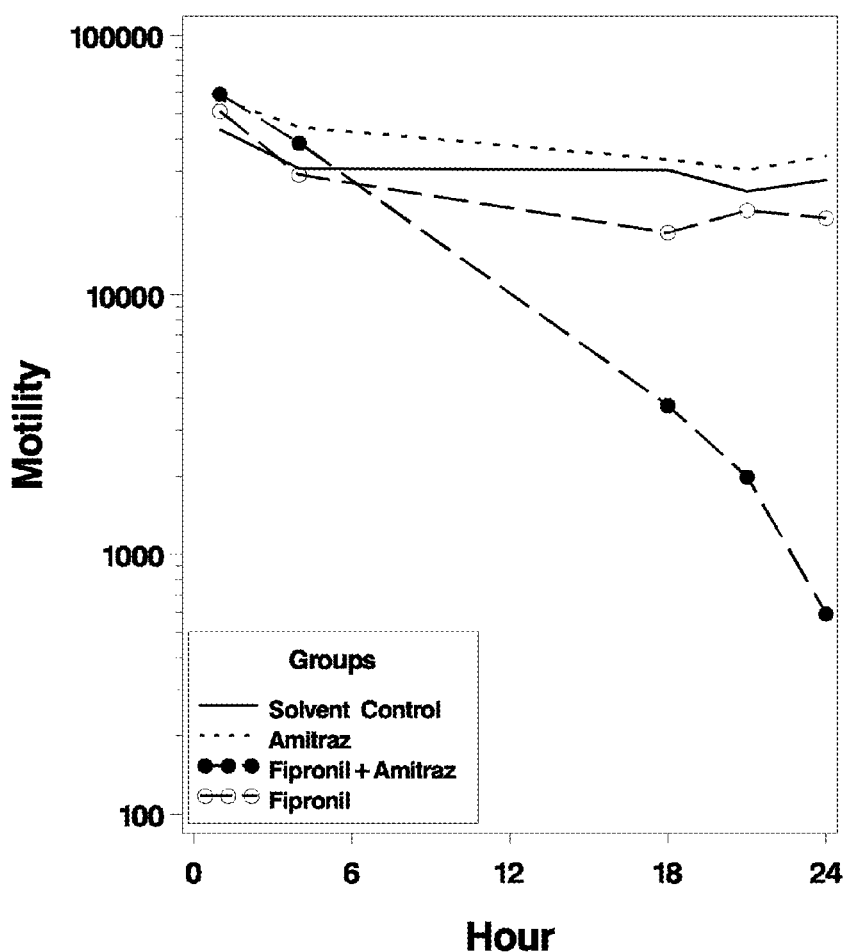
FIGURE 10. OVERALL GEOMETRIC MEAN OF MOTILITY FOR STIMULATED TICKS OVER TIME FIGURE 11. EFFICACY OF COMPOUND 1 AND FIPRONIL WITH AMITRAZ AGAINST FLEAS IN DOGS
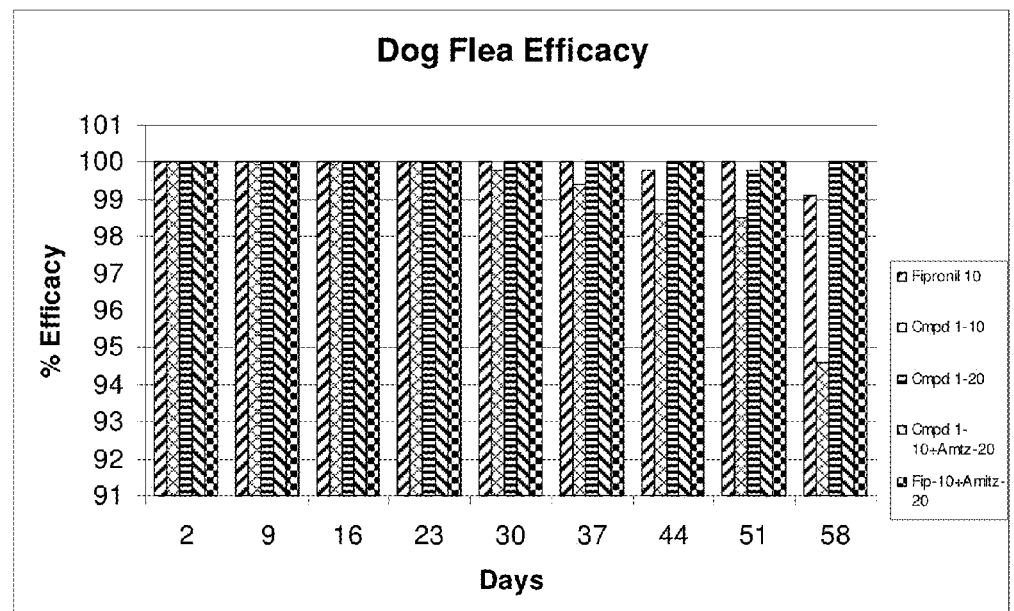
FIGURE 12. EFFICACY OF COMPOUND 1 AND FIPRONIL AGAINST FLEASE IN CATS
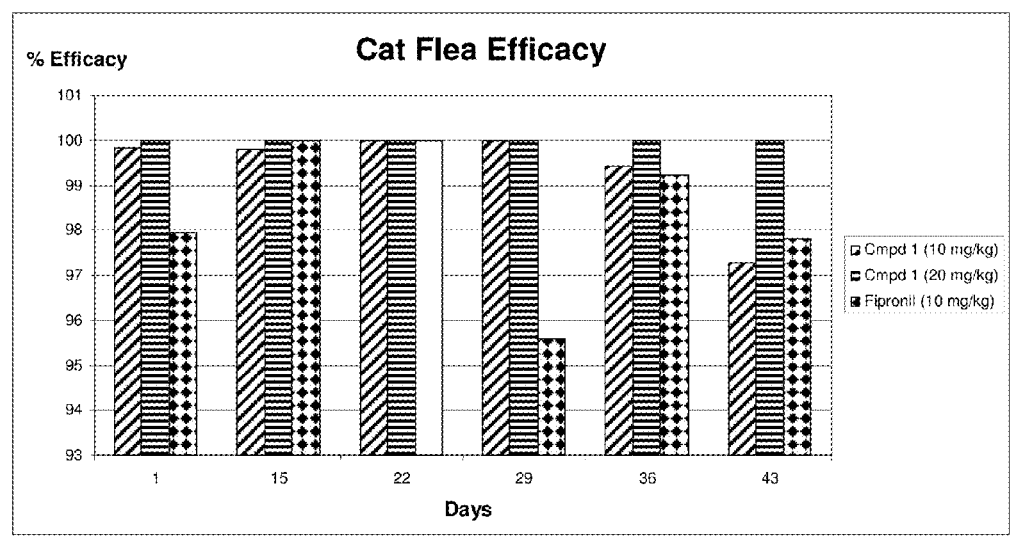

COMPOSITIONS COMPRISING AN ARYL PYRAZOLE AND/OR A FORMAMIDINE, METHODS AND USES THEREOF

CROSS REFERENCE TO RELATED APPLICATIONS

The present application is a divisional application of U.S. patent application Ser. No. 12/618,534 filed on Nov. 13, 2009; which claims the benefit of priority to U.S. Provisional Application Nos. 61/116,038, filed Nov. 19, 2008; 61/142,561, filed Jan. 5, 2009; and 61/167,381, filed Apr. 7, 2009; the disclosures of which are all incorporated herein by reference in their entirety.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Reference is made to U.S. Patent Publication Nos. US 2005/0234119 to Soll et al.; US 2008/0003282 to Soll et al.; US 2008/0031902 to Lee et al.; and U.S. Pat. No. 7,531,186, which issued on May 12, 2009, all of which are incorporated by reference herein in their entirety.

Citation or identification of any document in this application is not an admission that such document is available as prior art to the present invention.

FIELD OF THE INVENTION

The present invention provides veterinary compositions comprising 1-arylpyrazoles, alone or in combination with other active agents, for eradicating ectoparasites and/or endoparasites; the use of these compositions against ectoparasites and/or endoparasites, and methods for preventing or treating parasitic infestations of animals comprising administering the inventive composition of the invention to the animal. Also provided are compositions comprising a formamidine that exhibit improved stability, and a kit for treating or preventing parasitic infestations in animals, which comprises at least one 1-arylpyrazoles and at least one formamidines in a dual-cavity container.

BACKGROUND OF THE INVENTION

Animals such as mammals and birds are often susceptible to parasite infestations/infections. These parasites may be ectoparasites, such as insects, and endoparasites such as filariae and other worms. Domesticated animals, such as cats and dogs, are often infested with one or more of the following ectoparasites:

fleas (*Ctenocephalides* spp., such as *Ctenocephalides felis* and the like), ticks (*Rhipicephalus* spp., *Ixodes* spp., *Dermacentor* spp., *Amblyoma* spp., and the like), mites (*Demodex* spp., *Sarcoptes* spp., *Otodectes* spp., and the like), lice (*Trichodectes* spp., *Cheyletiella* spp., *Lignonathus* spp. and the like), mosquitoes (*Aedes* spp., *Culux* spp., *Anopheles* spp. and the like) and flies (*Hematobia* spp., *Musca* spp., *Stomoxys* spp., *Dematobia* spp., *Coclyomia* spp. and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents in both humans and animals. Major diseases which are caused by ticks include borrelioses (Lyme disease caused by *Borrelia burgdorferi*), babesioses (or piroplasmoses caused by *Babesia* spp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is the tick genus *Boophilus*, especially those of the species *microplus* (cattle tick), *decoloratus* and *annulatus*. Ticks, such as *Boophilus microplus*, are particularly difficult to control because they live in the pasture where farm animals graze. Other important parasites of cattle and sheep are listed as follows:

myiases-causing flies such as *Dermatobia hominis* (known as Berne in Brazil) and *Cochlyomia hominivorax* (greenbottle); sheep myiases-causing flies such as *Lucilia sericata, Lucilia cuprina* (known as blowfly strike in Australia, New Zealand and South Africa). These are flies whose larva constitutes the animal parasite;

flies proper, namely those whose adult constitutes the parasite, such as *Haematobia irritans* (horn fly);

lice such as *Linognathus vitulorum*, etc.; and mites such as *Sarcoptes scabiei* and *Psoroptes ovis*.

1-arylpyrazoles as a class of chemicals are well known in the art, and certain compounds in this class have been found to be potently active against a wide range of pests and parasites that are harmful to animals and plants. For example, 1-arylpyrazole derivatives are known in the art to prevent, treat or control ectoparasitic infestations in mammals, such as cats, dogs and cattle. Certain 1-arylpyrazoles and their use against pests are described in US Patent Publication Nos. US 2005/0182048; US 2006/0135778; US 2008/0132487; US 2008/0031902; U.S. Pat. Nos. 4,963,575; 5,122,530; 5,232,940; 5,236,938; 5,246,255; 5,547,974; 5,567,429; 5,576,429; 5,608,077; 5,714,191; 5,814,652; 5,885,607; 5,567,429; 5,817,688; 5,885,607; 5,916,618; 5,922,885; 5,994,386; 6,001,384; 6,010,710; 6,057,355; 6,069,157; 6,083,519; 6,090,751; 6,096,329; 6,124,339; 6,180,798; 6,335,357; 6,350,771; 6,372,774; 6,395,906; 6,413,542; 6,685,954; and 7,468,381. See also: EP 0 234 119, EP 0 295 117, EP 0 352 944, EP 0 500 209, EP 0 780 378, EP 0 846 686, and EP 0 948 485, all of which are incorporated herein by reference in their entirety.

The compounds of the families defined in these patents are extremely active and one of these compounds, 5-amino-3-cyano-1-(2,6-dichloro-4-trifluoromethylphenyl)-4-trifluoromethylsulfinylpyrazole, or fipronil, is particularly effective against pests, including fleas and ticks.

US 2008/031902 describes certain 1-arylpyrazole compounds that are substituted at the 5-position of the pyrazole ring with alkyl or $C_1$-$C_4$haloalkyl groups. These compounds were also found to be particularly effective against fleas and ticks.

These compounds are given as having activity against a very large number of parasites, including insects and acarines in fields as varied as agriculture, public health and veterinary medicine. The general teaching of these documents indicates that these active compounds may be administered via different routes: oral, parenteral, percutaneous and topical routes. Topical administration comprises, in particular, skin solutions (pour-on or spot-on), sprays, drenches, baths, showers, jets, powders, greases, shampoos, creams, etc. The pour-on type skin solutions may be designed for percutaneous administration.

Notwithstanding the effectiveness of certain arylpyrazole compounds certain parasites, it there continues to be a need for new formulations comprising 1-arylpyrazoles in pharmaceutically acceptable carriers that exhibit improved efficacy against parasites.

Other compounds that are known in the art to prevent, treat or control endo- and ectoparasitic infestations include milbemycin or avermectin derivatives, which are natural or semi-synthetic compounds that contain a 16-membered macrocyclic ring. The avermectin and milbemycin series of compounds are potent anthelmintic and antiparasitic agents against a wide range of internal and external parasites. The natural product avermectins are disclosed in U.S. Pat. No. 4,310,519 to Albers-Schonberg, et al., and the 22,23-dihydro-avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Naturally occurring milbemycins are described in Aoki et al., U.S. Pat. No. 3,950,360.

Another family of parasiticides are the formamidines which include but are not limited to amitraz (MITABAN®, Pfizer; POINT-GUARD®, Intervet; PREVENTIC®, Virbac; TAKTIC®, Intervet), chlordimeform, chloromebuform, formetanate and formparanate. Amitraz is a well-known acaracide/insecticide from the formamidine family acknowledged to be useful as a miticidal agent and for the control of ticks. See *Plumb's Veterinary Drug Handbook (Fifth Edition)*, ed. Donald C. Plumb, Blackwell Publishing, pg. 34, (2005). The formamidine family of compounds is distinguished by a characteristic —N=CR—NR'— moiety. Amitraz differs from other members of the formamidine family in that there are two such moieties in the compound. Amitraz has the following structure:

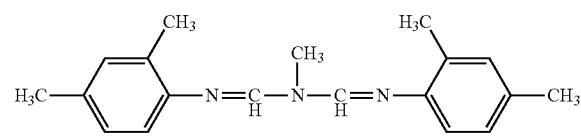

One problem associated with compositions comprising formamidine compounds, including amitraz, is the lack of long-term stability under certain conditions. For example, amitraz has been shown to degrade in aqueous solutions at certain pH ranges, as described, for example, in E. Corta, A. Bakkali, L. A. Berrueta, B. Gallo, F. Vicente, "Kinetics and Mechanism of Amitraz Hydrolysis in Aqueous Media by HPLC and GC-MS", Talanta 48 (1999) 189-199. Some amitraz degradates have further shown pesticidal efficacy, such as described, for example, in Osborne, M. P., "Actions of Formamidines, Local Anesthetics, Octopamine and Related Compounds Upon the Electrical Activity of Neurohaemal Organs of the Stick Insect (*Carausius morosus*) and Sense Organs of Fly Larvae (*Musca demstica, Calliphora erythrocephala*)", Pesticide Biochemistry and Physiology 23, 190-204 (1985).

Therefore, although formamidine parasiticides, including amitraz, have considerable utility for treating and preventing parasitic infestations, there are several problems associated with using amitraz as a parasiticide in a commercial veterinary pharmaceutical product. These problems include: (1) insufficient stability at certain pH values: while amitraz is stable at higher pH values, amitraz tends to hydrolyze over time at pH ranges commonly associated with physiological use (e.g. pH of about 5.0 to about 6.0); (2) amitraz is not effective for the control of fleas; and (3) compositions comprising amitraz may not provide a sufficiently long term shelf life in mixtures with some antiparisitic agents and certain carriers. For example, compositions containing amitraz may not have sufficient long term stability (shelf life) in certain solvent systems which are optimal for other antiparasitic agents with which it may be combined.

Potential solutions to the stability problems have often resulted in solutions with long lasting odors or adverse reactions which rendered these solutions unsuitable for once monthly pharmaceutical or veterinary use.

A composition comprising a 1-aryl-pyrazole with a formamidine compound, e.g. fipronil with amitraz, which exhibits synergistic efficacy against ectoparasites is described in U.S. Pat. No. 7,531,186 to Boeckh et al.; however certain embodiments of the composition, where a 1-arylpyrazole and a formamidine are present together in certain carriers, may not have a sufficiently long storage shelf life. One possible reason for the insufficient long term shelf life is that fipronil is stable at a pH of about 5.0 to about 6.0, while amitraz will degrade at this pH range. Thus, there remains a need in the art for formulations, methods of storage and methods of administration which provide 1-aryl-pyrazoles and formamidines in a synergistically active formulation to treat parasites. There also exists a need in the art to provide compositions comprising amitraz which provide enhanced stability with other active agents, including 1-arylpyrazoles, and improved dissipation of odor.

Citation or identification of any document in this application is not an admission that such document is available as prior art to the present invention.

SUMMARY OF THE INVENTION

The present invention provides compositions and formulations comprising a 1-arylpyrazole compound or a 1-arylpyrazole compound in combination with a formamidine compound, formulations and uses or veterinary uses thereof for the treatment or prophylaxis of parasitic infestations of animals (either wild or domesticated), including livestock and companion animals such as cats, dogs, horses, chickens, sheep, goats, pigs, turkeys and cattle, with the aim of ridding these hosts of parasites commonly encountered by such animals.

The invention also provides methods for the treatment or prevention of parasitic infestations in animals, comprising administering an effective amount of a composition comprising at least one 1-arylpyrazole or a 1-arylpyrazole in combination with at least one formamidine compound to the animal. Surprisingly, it has been found that the inventive compositions and formulations described herein exhibit superior stability and synergistic efficacy against harmful parasites over a long duration compared to compositions known in the art. In particular, the present invention has surprisingly overcome the problems associated with the instability of a formamidine in solution and the problems associated with the instability of a solution comprising a 1-arylpyrazole and a formamidine.

The compositions or formulations of the invention include spot-on, pour-on or spray formulations and may include a further ectoparasiticide, such as an insect growth regulator (IGR), an avermectin or milbemycin derivative, an acaricide, a pyrethroid insecticide, or an anthelmintic, such as benzimidazoles or imidazothiazoles.

One aspect of the invention provides compositions comprising at least one 1-aryl-5-alkyl or 1-aryl-5-haloakylpyrazole compound of formula (IA)

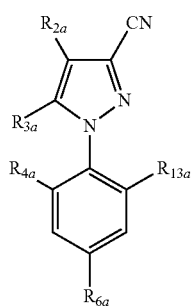

(IA)

wherein variables $R_{2a}$, $R_{3a}$, $R_{4a}$, $R_{6a}$ and $R_{13a}$ are as defined below, in combination with a veterinarily acceptable carrier, and optionally with at least one crystallization inhibitor.

Another object of the invention is to provide a composition for the treatment and prevention of a parasitic infestation in an animal comprising at least one 1-arylpyrazole compound in a first veterinarily acceptable carrier, at least one formamidine compound in a second veterinarily acceptable carrier, and optionally at least one crystallization inhibitor; wherein the 1-arylpyrazole compound(s) and first veterinarily acceptable carrier are isolated and not in fluid communication with the formamidine compound(s) and the second veterinarily acceptable carrier.

In some embodiments, the 1-arylpyrazole compounds have the formula (IB) shown below, where the variables $R_{2b}$, $R_{3b}$, $R_{4b}$, $R_{6b}$ and Z are described below.

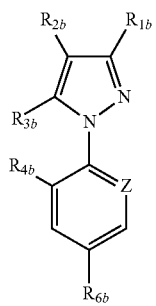

(IB)

In other embodiments, the formamidine compounds in the compositions of the invention have the formula (II) shown below, where variables $R_{14}$, $R_{15}$, $R_{16}$, $R_{17}$ and x are described below.

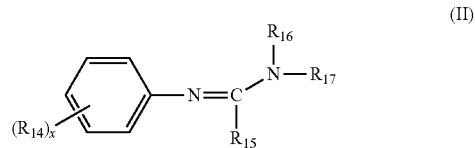

(II)

In some embodiments, the invention provides compositions and methods comprising at least one 1-arylpyrazole compound in a first veterinarily acceptable carrier and at least one formamidine compound in a second veterinarily acceptable carrier, where the compounds and veterinarily acceptable carriers are stored and administered from dual-cavity containers. The methods and compositions allow for stable synergistic compositions comprising 1-arylpyrazole compounds and formamidine compounds that have superior activity against parasites. In preferred embodiments, the 1-arylpyrazole compound is fipronil and the formamidine compound is amitraz. In some embodiments, the 1-arylpyrazole compound(s) and the corresponding carrier is administered simultaneously with the formamidine compound(s) in a second carrier.

Also provided are stable formamidine compositions in certain carriers. In some embodiments, the carriers include solvents with dielectric constants of about 2 to about 30 that are acceptable for pharmaceutical and/or veterinary use. In other embodiments, the carriers include aprotic solvents or polar aprotic solvents. In still other embodiments, the carrier includes aprotic solvents or polar aprotic solvents with dielectric constants of about 2 to about 30. In some embodiments, the formamidine compositions comprising a mixture of at least two solvents with dielectric constants of about 2 to about 30 exhibit surprisingly improved odor dissipation compared to prior art compositions.

The invention also provides a kit for the treatment or prevention of a parasitic infestation in an animal, which comprises at least one 1-arylpyrazole compound in a first veterinarily acceptable carrier, at least one formamidine compound in a second veterinarily acceptable carrier, and a multiple cavity container; wherein the one or more 1-arylpyrazole compound(s) in the first veterinarily acceptable carrier is in a first cavity of the multiple cavity container and the one or more formamidine compound(s) and the second veterinarily acceptable carrier are in a second cavity of the multiple cavity container.

Accordingly, it is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

BRIEF DESCRIPTION OF THE DRAWINGS

FIG. 10 shows the effect of fipronil alone, amitraz alone and a fipronil/amitraz combination on the geometric mean of tick motility over time
FIG. 11 shows the % efficacy of various compositions of the invention against fleas in dogs.
FIG. 12 shows the % efficacy of various compositions of the invention against fleas in cats.

DETAILED DESCRIPTION

Figure 1:
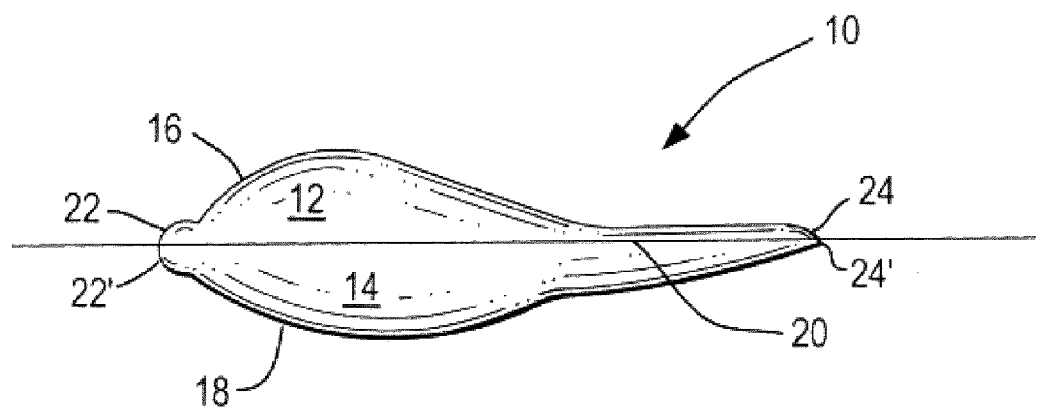
FIG. 1 is a side view of an embodiment of a container.

The present invention provides novel and inventive compositions and formulations comprising at least one 1-arylpyrazole compound alone or in combination nation with one or more formamidine compound(s) and a veterinarily acceptable carrier or diluent. Also provided are methods and uses for the treatment or prophylaxis of parasitic infections and infestations of animals, comprising administering an effective amount of a composition of the invention to the animal. Surprisingly, it has been found that the inventive compositions and formulations described herein comprising a 1-arylpyrazole compound alone or in combination with a formamidine compound exhibit superior stability and efficacy, including synergistic efficacy in some embodiments, against harmful parasites. In particular, the present invention has surprisingly overcome the problems associated with the lack of long term stability of a formamidine in solution and the problems associated with the insufficient shelf life of a composition comprising a 1-arylpyrazole and a formamidine in certain carriers.

The invention includes at least the following features:

(a) In one embodiment, the invention provides novel compositions comprising at least one 1-arylpyrazole of formula (I), or veterinarily acceptable salts thereof, together with a veterinarily acceptable carrier or diluent, that exhibit superior activity against animal parasites and improved stability;

(b) veterinary compositions comprising at least one formamidine of formula (II), or veterinarily acceptable salts thereof, together with a veterinarily acceptable carrier or diluent, that exhibit improved stability;

(c) veterinary composition comprising at least one 1-arylpyrazole of formula (I) and a formamidine of formula (II), or veterinarily acceptable salts thereof, together with one or more veterinarily acceptable carrier(s) or diluent(s), that exhibits synergistic efficacy against animal parasites and improved stability;

(d) methods for the treatment or prevention of parasitic infestations in an animal comprising administering an effective amount of a composition comprising at least one 1-arylpyrazole of formula (I), or veterinarily acceptable salts thereof, to the animal in a veterinarily acceptable carrier or diluent;

(e) methods for the treatment or prevention of parasitic infestations in animals comprising administering an effective amount of a composition comprising at least one formamidine of formula (II), or veterinarily acceptable salts thereof, in a veterinarily acceptable carrier or diluent, wherein the formamidine exhibits superior stability in solution;

(f) methods for the treatment or prevention of parasitic infestations in animals comprising administering an effective amount of at least one 1-arylpyrazole of formula (I) and at least one formamidine of formula (II), or veterinarily acceptable salts thereof, together with veterinarily acceptable carriers or diluents, wherein the 1-arylpyrazole(s) and the formamidine compound(s) are administered in separate carriers;

(g) methods for the treatment or prevention of parasitic infestations in animals comprising administering an effective amount of at least one 1-arylpyrazole of formula (I) and at least one formamidine of formula (II), or veterinarily acceptable salts thereof, together with veterinarily acceptable carriers or diluents, wherein the 1-arylpyrazole(s) and the formamidine compound(s) are administered simultaneously;

(h) methods for the treatment or prevention of parasitic infestations in animals comprising administering an effective amount of at least one 1-arylpyrazole of formula (I) and at least one formamidine of formula (II), or veterinarily acceptable salts thereof, together with veterinarily acceptable carriers or diluents, wherein the 1-arylpyrazole(s) and the formamidine(s) are administered simultaneously and the 1-arylpyrazole(s) and the formamidine(s) are in separate carriers;

(i) methods for the treatment or prevention of parasitic infestations in animals comprising administering an effective amount of at least one 1-arylpyrazole of formula (I) and at least one formamidine of formula (II), or veterinarily acceptable salts thereof, together with veterinarily acceptable carriers or diluents, wherein 1-arylpyrazole(s) and the formamidine(s) are administered simultaneously using a dual-cavity container that holds the 1-arylpyrazole and the formamidine in separate carriers; and (j) a dual-cavity container for storing and administering the compositions of the invention, wherein the container comprises a first cavity defined by a front wall and a divider wall, and a second cavity defined by a rear wall and a divider wall.

In this disclosure and in the claims, terms such as "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

It is also noted that in this disclosure and in the claims and/or paragraphs, the compounds of the invention are intended to include all stereoisomers and crystalline forms (which includes hydrated forms, polymorphic forms and amorphous forms with up to 15% by weight crystalline structure) thereof.

DEFINITIONS

Terms used herein will have their customary meaning in the art unless specified otherwise. The organic moieties mentioned in the definitions of the variables of formula (I) or (II)

are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals, including humans. Animals include, but are not limited to, humans, cats, dogs, cattle, chickens, cows, deer, goats, horses, llamas, pigs, sheep and yaks. It also includes an individual animal in all stages of development, including embryonic and fetal stages.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyl, may be referred to as "cycloalkyl" and include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Cycloalkenyl" refers to monovalent cyclic alkenyl groups of from 4 to 10 carbon atoms, preferably 5 to 8 carbon atoms, having single or multiple condensed rings which condensed rings may or may not be cycloalkenyl provided that the point of attachment is to a cycloalkenyl ring atom. Examples of cycloalkenyl groups include, by way of example, cyclopenten-4-yl, cyclooctene-5-yl and the like. Alkenyl and cycloalkenyl groups may be unsubstituted or substituted with one or more substituents as described for alkyl above.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Alkoxycarbonyl refers to —C($=$O)—O-alkyl, wherein alkoxy is as defined above;

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$)).

Stereoisomers and Polymorphic Forms

It will be appreciated by those of skill in the art that the compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The hydrates and solvates of the compounds of formula (I) or (II) are also the subject of the invention.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically or veterinarily acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinarily acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts (NH4+), alkyl- and dialkylammonium salts, and salts of cyclic amines such as the morpholine and piperidine salts.

A first aspect of the invention provides a formulation with increased stability and/or efficacy for treating or preventing an infestation of an animal with ectoparasites and/or endoparasites comprising:

(a) a 1-aryl pyrazole compound of formula (I), or a veterinarily acceptable salt thereof:

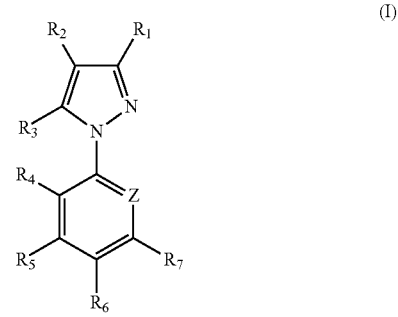

wherein:
$R_1$ is hydrogen, cyano, nitro, halogen, $R_3$, $R_8$, formyl, —C(O)$R_8$, —C(O)O$R_8$, —C(O)N$R_9R_{10}$, —C(=NOH)NH$_2$, —C(=NNH$_2$), or —C(S)NH$_2$;
$R_2$ is $R_8$, halogen, cyano, nitro, —SCN, 4-5-dicyanoimidazol-2-yl, or —S(O)$_m R_{11}$;
$R_3$ is alkyl, haloalkyl, OH, or N$R_9R_{10}$;
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —C(O)$R_{12}$, —S(O)$_n R_{12}$ or SF$_5$;
Z is a nitrogen atom or C—$R_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl, alkoxy, or —C(O)$R_8$;
wherein said alkyl, haloalkyl, alkoxy, or —C(O)$R_8$ groups are optionally substituted with alkyl, haloalkyl, cycloalkyl, alkoxy, aryl, or heteroaryl; wherein said aryl or heteroaryl groups are optionally substituted with one or more groups selected from the group consisting of alkyl, cycloalkyl, haloalkyl, aryl, halogen, C(O)$R_8$, —C(O)O$R_8$, —C(O)N$R_9R_9$, —C(S)NH$_2$, or —S(O)$_m R_{11}$
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof;
(b) a pharmaceutical or veterinarily acceptable carrier vehicle; and
(c) optionally, a crystallization inhibitor.

Compounds of formula (I) and methods for preparing the compounds are described, for example, in U.S. Pat. Nos. 6,096,329; 6,395,765; 6,685,954; 6,867,229; EP 0 205 117 and WO 87/03781, all of which are incorporated herein by reference in their entirety.

It is a second aspect of the invention to provide for formulations comprising 1-arylpyrazole compounds that exhibit improved efficacy and/or stability. It has been surprisingly been discovered that spot-on, pour-on or spray-on formulations of 1-arylpyrazole compounds in certain carriers exhibit enhanced stability and/or efficacy against ectoparasites and/or endoparasites compared to formulations of 1-arylpyrazoles of the prior art.

In one embodiment, the pharmaceutically or veterinarily acceptable carrier comprises acetone, acetonitrile, benzyl alcohol, ethanol, isopropanol, diisobutyl adipate, diisopropyl adipate (also known as CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, butyl acetate, octyl acetate, propylene carbonate, butylene carbonate, dimethyl sulfoxide, amides including dimethylformamide and dimethylacetamide, or any combination thereof.

In one preferred embodiment of the invention, the pharmaceutically or veterinarily acceptable carrier of the formulation includes $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

In another embodiment of the invention, the carrier may include diisopropyl adipate, dipropylene glycol monomethyl ether, propylene glycol monomethyl ether, 2-pyrrolidone including N-methylpyrrolidone, diethylene glycol monoethyl ether, triacetin, butyl acetate, octyl acetate, propylene carbonate, oleic acid, or a mixture of at least two of these solvents.

In yet another embodiment of the invention, the carrier may include triacetin or diethylene glycol monoethyl ether.

It is a further aspect of the invention to provide for formulations with enhanced efficacy against ectoparasites, such as fleas, ticks, mites, mosquitoes, flies and lice. The invention may also be effective against endoparasites, cestodes, nematodes, such as filariae, and roundworms of the digestive tract of animals and humans.

In another embodiment of the invention, the pharmaceutically or veterinarily acceptable carrier is an organic solvent commonly used in the formulation art. These organic solvents may be found, for example, in Remington Pharmaceutical Sciences, 16$^{th}$ Edition (1986). These solvents include, for example, acetone, ethyl acetate, methanol, ethanol, isopropanol, dimethylformamide, dichloromethane or diethylene glycol monoethyl ether (TRANSCUTOL), diisobutyl adipate, diisopropyl adipate (CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, acetates of $C_1$-$C_{10}$ alcohols, $C_{10}$-$C_{18}$ monounsaturated fatty acids or esters thereof, propylene carbonate, butylene carbonate, or any combination thereof. These solvents can be supplemented by various excipients according to the nature of the desired phases, such as $C_8$-$C_{10}$ caprylic/capric triglyceride (ESTASAN or MIGLYOL 812), oleic acid or propylene glycol.

In one embodiment, the invention provides a formulation that comprises a 1-arylpyrazole of formula (I) wherein $R_1$ is cyano, —C(O)$R_8$, —C(O)O$R_8$, —C(O)N$R_9R_{10}$, —C(=NOH)NH$_2$, —C(=NNH$_2$), or —C(S)NH$_2$, and all the other variables are as defined above.

In another embodiment, the invention provides a formulation comprising a 1-arylpyrazole of formula (I) wherein $R_3$ is alkyl or haloalkyl.

In one embodiment, the invention provides a formulation comprising a 1-arylpyrazole of formula (I) wherein:
$R_1$ is cyano, —C(O)$R_8$, —C(O)O$R_8$, —C(O)N$R_9R_{10}$, —C(=NOH)NH$_2$, —C(=NNH$_2$), or —C(S)NH$_2$; and
$R_2$ is —SCN, 4-5-dicyanoimidazol-2-yl, or —S(O)$_m$$R_{11}$.

In another embodiment, the invention provides a formulation comprising a 1-arylpyrazole of formula (I) wherein:
$R_1$ is cyano, —C(O)$R_8$, —C(O)O$R_8$, —C(O)N$R_9R_{10}$, —C(=NOH)NH$_2$, —C(=NNH$_2$), or —C(S)NH$_2$;
$R_2$ is —SCN, 4-5-dicyanoimidazol-2-yl, or —S(O)$_m$$R_{11}$; and
$R_3$ is alkyl or haloalkyl.

In still another embodiment, the invention provides a formulation comprising a 1-arylpyrazole of formula (I) wherein:
$R_1$ is cyano;
$R_2$ is —SCN, 4-5-dicyanoimidazol-2-yl, or —S(O)$_m$$R_{11}$;
$R_3$ is alkyl or haloalkyl;
$R_4$, $R_5$ and $R_7$ are independently hydrogen, or halogen; and
Z is C—$R_{13}$.

In another embodiment, the invention provides a formulation comprising a 1-arylpyrazole of formula (I) wherein:
$R_1$ is cyano;
$R_2$ is —SCN, 4-5-dicyanoimidazol-2-yl, or —S(O)$_m$$R_{11}$;
$R_3$ is $C_1$-$C_4$alkyl or $C_1$-$C_4$haloalkyl;
$R_6$ is halogen, haloalkyl or SF$_5$; and
Z is C—$R_{13}$.

In one embodiment, the invention provides a formulation comprising a 1-arylpyrazole of formula (I) wherein:
$R_1$ is cyano;
$R_2$ is —S(O)$_m$$R_{11}$;
$R_3$ is $C_1$-$C_4$alkyl, $C_1$-$C_4$haloalkyl, or N$R_9R_{10}$;
$R_4$, $R_5$ and $R_7$ are independently hydrogen, or halogen;
$R_6$ is halogen, $C_1$-$C_4$alkyl, $C_1$-$C_4$haloalkyl, or SF$_5$;
Z is C—$R_{13}$; and
$R_{13}$ is halogen or $C_1$-$C_4$haloalkyl.

In another embodiment of the formulation, a 1-arylpyrazole of formula (I) is provided wherein:
$R_1$ is cyano;
$R_2$ is —S(O)$_m$$R_{11}$;
$R_3$ is methyl, ethyl, propyl, or $C_1$-$C_4$haloalkyl;
$R_4$ is halogen;
$R_5$ and $R_7$ are hydrogen;
$R_6$ is $C_1$-$C_4$haloalkyl;
Z is C—$R_{13}$;
$R_{11}$ is —CF$_3$, —CClF$_2$, or CFCl$_2$; and
$R_{13}$ is halogen.

In still another embodiment, the invention provides a formulation comprising a 1-arylpyrazole of formula (I) wherein:
$R_1$ is cyano;
$R_2$ is —S(O)$_m$$R_{11}$;
$R_3$ is methyl or ethyl;
$R_4$ is chloro or fluoro;
$R_5$ and $R_7$ are hydrogen;
$R_6$ is —CF$_3$;
Z is C—$R_{13}$;
$R_{11}$ is —CFCl$_2$; and
$R_{13}$ is chloro or fluoro.

In another embodiment, the invention provides a formulation comprising a 1-aryl-alkyl or 5-haloalkylpyrazole of formula (I) that has the structure of formula (IA) below in com bination with a veterinarily acceptable carrier and optionally a crystallization inhibitor:

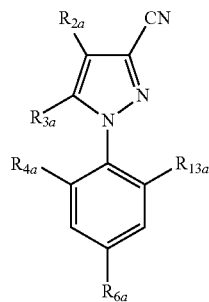

or a salt thereof, wherein:
$R_{2a}$ is —S(O)$_m$R$_{11a}$;
$R_{3a}$ is methyl, ethyl or $C_1$-$C_4$ haloalkyl;
$R_{4a}$ is halogen;
$R_{6a}$ is $C_1$-$C_4$ alkyl or haloalkyl;
$R_{13a}$ is halogen;
$R_{11a}$ is $C_1$-$C_4$ haloalkyl; and
m is 0, 1 or 2.

Compounds of formula (IA) as well as process for the preparation of these compounds are described in US 2008/0031902 A1 to Lee et al., which is incorporated herein by reference in its entirety.

In another embodiment, the invention provides a formulation that comprises a 1-aryl-5-alkyl pyrazole compound of formula (IA) wherein:
$R_{2a}$ is —S(O)$_m$R$_{11a}$;
$R_{3a}$ is methyl, or ethyl;
$R_{4a}$ is halogen;
$R_{6a}$ is $C_1$-$C_4$ haloalkyl;
$R_{13a}$ is halogen;
$R_{11a}$ is —CF$_3$, —CClF$_2$, or —CFCl$_2$; and
m is 0, 1 or 2.

In another embodiment, the invention provides a formulation that comprises a 1-aryl-5-alkyl pyrazole compound of formula (IA) wherein:
$R_{2a}$ is —S(O)$_m$R$_{11a}$;
$R_{3a}$ is methyl, or ethyl;
$R_{4a}$ is halogen;
$R_{6a}$ is $C_1$-$C_4$ haloalkyl;
$R_{13a}$ is halogen;
$R_{11a}$ is —CF$_3$, —CClF$_2$, or —CFCl$_2$; and
m is 0, 1 or 2.

In still another embodiment of the invention, a formulation is provided that comprises a 1-aryl-5-alkyl pyrazole compound of formula (IA) wherein:
$R_{2a}$ is —S(O)$_m$R$_{11a}$;
$R_{3a}$ is methyl;
$R_{4a}$ is —Cl;
$R_{6a}$ is —CF$_3$;
$R_{13a}$ is —F;
$R_{11a}$ is —CFCl$_2$; and
m is 0, 1 or 2.

In another embodiment, the invention provides a formulation comprising 3-cyano-1-(2-chloro-6-fluoro-4-trifluoromethylphenyl)-4-dichlorofluoromethylsulfinyl-5-methyl-1H-pyrazole (Compound 1) in combination with a pharmaceutically or veterinarily acceptable carrier and optionally a crystallization inhibitor.

It has been surprisingly discovered that 1-aryl-5-alkyl or 5-haloalkyl pyrazole compounds are highly efficacious against ectoparasites and provide long-lasting protection against ectoparasites for at least 30, at least 40 or at least 60 days. Thus, 1-aryl-5-alkyl or 5-haloalkyl pyrazoles of formula (IA) are extremely useful and offer substantial advantages to other paraciticidal compounds. Furthermore, it has been discovered that 1-aryl-5-alkyl or 5-haloalkyl pyrazole compounds of formula (IA) are able to eradicate parasites, particularly fleas and ticks, from animals more quickly than other parasiticides.

A third aspect of the invention provides a composition comprising one or more formamidine compounds including, but not limited to amitraz, that exhibits enhanced stability. The formamidine compositions of the invention typically comprise amitraz in combination with an aprotic solvent. In preferred embodiments, the compositions comprise a veterinarily effective amount of a formamidine in combination with a polar aprotic solvent. Aprotic solvents and polar aprotic solvents are well known in the art, and the invention provides compositions comprising any veterinarily acceptable aprotic or polar aprotic solvent that provides sufficient solubility for the formamidine compound may be used. Particularly preferred polar aprotic solvents include carboxylic acid esters, ketones and aryl ethers.

In other embodiments, the stable formamidine compositions of the invention comprise a veterinarily effective amount of one or more formamidine compounds and solvent with a dielectric constant of about 2 to about 30. In some preferred embodiments, the stable formamidine compositions of the invention comprise aprotic solvents that have a dielectric constant of about 2 to about 30. In still more preferred embodiments, the stable formamidine compositions comprise polar aprotic solvents that have a dielectric constant of about 2 to about 30.

In other embodiments of the invention, the carrier comprises a solvent with a dielectric constant of about 2 to about 40, 2 to about 20, 5 to about 30, or 10 to about 30. Preferably, the solvent with dielectric constants of about 2 to about 40 is an aprotic solvent or a polar aprotic solvent.

In other embodiments, the carrier comprises one or more solvents with a dielectric constant of about 2 to about 15 or about 3 to about 10. In still another embodiment, the dielectric constant of the one or more solvents is about 3.5 to about 10. In another embodiment, the dielectric constant of the one or more solvents is about 4 to about 6.5.

In other embodiments of the invention, the carrier comprises one or more aprotic solvents with dielectric constants of about 2 to about 40, 2 to about 20, 5 to about 30, or 10 to about 30.

In other embodiments, the carrier comprises one or more aprotic solvents with dielectric constants of about 2 to about 15 or about 3 to about 10. In still another embodiment, the dielectric constant of the one or more aprotic solvents is about 3.5 to about 10. In another embodiment, the dielectric constant of the one or more aprotic solvents is about 4 to about 6.5.

In other embodiments of the invention, the carrier comprises one or more polar aprotic solvents with dielectric constants of about 2 to about 40, 2 to about 20, 5 to about 30, or 10 to about 30.

In other embodiments, the carrier comprises one or more polar aprotic solvents with dielectric constants of about 2 to about 15 or about 3 to about 10. In still another embodiment, the dielectric constant of the one or more polar aprotic solvents is about 3.5 to about 10. In another embodiment, the dielectric constant of the one or more polar aprotic solvents is about 4 to about 6.5.

In one embodiment, the carrier comprises a single solvent with a dielectric constant of about 2 to about 30. In still another embodiment, the carrier comprises a mixture of two or more solvents with a dielectric constant of about 2 to about 30, which may preferably be aprotic or polar aprotic.

In still another embodiment, the carrier comprises a solvent with a dielectric constant of about 2 to about 30 in combination with one or more solvents that do not have a dielectric constant of about 2 to about 30.

In other embodiments, the solvent in the stable formamidine compositions will contain less than about 0.5% or less than about 0.3% (w/w) water. In other embodiments, the solvent will typically contain less than 0.2% (w/w) water. Preferably, the solvent will contain less than about 0.1%, or less than about 0.05% or less than about 0.025% (w/w) water. In other embodiments, the solvent will contain from about 0.0001% (w/w) to about 0.5% (w/w) water. More typically, the solvent will contain about 0.0001% to about 0.3%, about 0.001% to about 0.3%, about 0.001% to about 0.1% or about 0.001% to about 0.05% (w/w) water. Preferably, the solvent will contain from about 0.001% to about 0.025% (w/w) water. As discussed above, amitraz has been shown to be unstable in aqueous solutions at certain pH ranges or solutions containing significant amounts of water at certain pH ranges.

Furthermore, it has been found that formamidine compounds, and amitraz in particular, may not have sufficient long term stability in certain solvent systems. For example, in certain solvent systems amitraz may not provide a sufficient shelf life for use as a commercial veterinary pharmaceutical product. Therefore, compositions of formamidines in certain carriers that exhibit enhanced stability are highly desired.

In one embodiment, the invention provides a composition comprising a formamidine, including amitraz, in combination with a suitable carrier that is stable for up to about 2 months at about 50° C. It will be appreciated by those of skill in the art that a stable composition comprising a formamidine, as described herein, will show less than about 5% degradation of the formamidine compound at the indicated conditions (temperature and relative humidity) relative to the initial measure of purity or concentration, as tested by a suitable stability-indicating method for a given period of time. Preferably, the stability of a formulation is evaluated by HPLC by measuring the change in concentration of the active in the formulation over time against a reference standard.

In another embodiment, the invention provides a composition comprising a formamidine, including amitraz, that is stable for at least about 3 months at about 50° C. In still other embodiments, the invention provides a composition comprising a formamidine, including amitraz, that is stable for at least about 4 months, at least about 5 months or at least about 6 months at about 50° C.

In another embodiment, the invention provides a composition comprising a formamidine compound, including amitraz, that is stable for at least 3 months at about 40° C. and about 75% relative humidity (RH). In still another embodiment, the composition comprising a formamidine compound will be stable for at least 6 months at about 40° C. and 75% RH. In still another embodiment, the composition comprising a formamidine will be stable for at least 9 months at about 40° C. and 75% RH.

In another embodiment, the invention provides a composition comprising a formamidine, including amitraz, that is stable for at least about 12 months at about 25° C. and about 60% RH. In other embodiments, the invention provides a composition comprising a formamidine, including amitraz, that is stable for at least about 18 months, about 24 months or about 36 months at about 25° C. and about 60% RH.

In some embodiments, the invention provides stable compositions comprising a formamidine in combination with one or more of amides including dimethylformamide, dimethylacetamide, N-methylpyrrolidone and the like; one or more sulfoxides including dimethyl sulfoxide and the like; and combinations thereof.

In one embodiment, the solvent includes aryl ethers including alkoxybenzene compounds; carboxylic acid esters, including aliphatic and aromatic carboxylic acids such as benzoic acid esters, and compounds with multiple carboxylate groups; aliphatic ketones, saturated aliphatic ketones, cyclic ketones, or mixtures thereof.

In another embodiment, the solvent includes $C_1$-$C_{10}$ carboxylic acid esters, phenyl carboxylic acid esters, carboxylic acid benzyl esters, benzoic acid $C_1$-$C_4$ alkyl esters, $C_1$-$C_6$ saturated aliphatic ketones, and mixtures thereof.

Examples of carboxylic acid esters include, but are not limited to $C_1$-$C_{20}$ alkyl esters of alkanoic acids. In one embodiment, the solvent includes $C_1$-$C_{20}$ alkyl esters of $C_1$-$C_{12}$ alkanoic acids. In other embodiments, the solvent includes $C_1$-$C_{12}$ alkyl esters of $C_1$-$C_{12}$ alkanoic acids, $C_1$-$C_{12}$ alkyl esters of $C_1$-$C_{10}$ alkanoic acids, $C_1$-$C_{12}$ alkyl esters of $C_1$-$C_8$ alkanoic acids, $C_1$-$C_{12}$ alkyl esters of $C_1$-$C_6$ alkanoic acids or $C_1$-$C_{12}$ alkyl esters of $C_1$-$C_4$ alkanoic acids. In various embodiments, the solvent includes $C_1$-$C_{12}$ alkyl esters of formic acid, acetic acid, propionic acid, butanoic acid, pentanoic acid, isobutanoic acid, hexanoic acid, heptanoic acid, octanoic acid, nonanoic acid, decanoic acid, and the like.

Also encompassed by the invention are phenyl and benzyl esters of alkyl carboxylic acids. Other carboxylic acid esters include $C_1$-$C_{20}$ alkyl esters of di-carboxylic and tri-carboxylic acids including, but not limited to, malonic acid, succinic acid, glutaric acid, adipic acid, citric acid, and the like.

Aromatic carboxylic acid esters are also contemplated, including $C_1$-$C_{20}$ alkyl esters of aromatic carboxylic acids as well as well as benzyl esters of aromatic carboxylic acids. Non-limiting examples of aromatic carboxylic acids include, but are not limited to, benzoic acid, phenylacetic acid, salicylic acid, mandelic acid, phthalic acid, cynnamic acid, and the like.

Aliphatic ketones that may be used as solvents for veterinary formulations are well known in the art and include, but are not limited to, acetone, methyl ethyl ketone, methyl isobutyl ketone, methyl isopropyl ketone, 2-butanone, 2-pentanone, 3-pentanone, 2-hexanone, 3-hexanone, and the like.

Aryl ethers that may be used include, but are not limited to, $C_1$-$C_{12}$ alkyl-aryl ethers such as anisole and derivatives of anisole, ethyl phenyl ether (phenetole), propyl phenyl ether, butyl phenyl ether, and the like.

In still another embodiment of the third aspect of the invention, the solvent of the stable formamidine compositions includes $C_1$-$C_4$-alkoxybenzene, $C_1$-$C_{10}$ carboxylic acid esters, phenyl carboxylic acid esters, carboxylic acid benzyl esters, $C_1$-$C_6$ saturated aliphatic ketones, benzoic acid $C_1$-$C_4$ esters or mixtures thereof.

In other embodiments, the solvent includes methoxybenzene (4.33), butyl acetate (5.0), benzyl acetate (5.0), methyl isobutyl ketone (13.1), ethyl benzoate (6.02), benzyl benzoate (4.8), octyl acetate or mixtures thereof. (Dielectric constants in parentheses)

In one embodiment, the solvent is a mixture of butyl acetate and anisole or a mixture of butyl acetate and methyl isobutyl ketone.

In another embodiment of the invention, the solvent is octyl acetate. In another embodiment, the carrier comprises a mixture of octyl acetate with another aprotic solvent or with a solvent having a dielectric constant of about 2 to about 30. In a preferred embodiment, the solvent will be a polar aprotic solvent with a dielectric constant of about 2 to about 30. In still another embodiment, the carrier comprises a mixture of octyl acetate with one or more of butyl acetate, methyl isobutyl ketone or anisole.

In one embodiment of the invention, the [weight/volume]% solubility of amitraz at room temperature in the solvent is from about 20% to about 50%. In another embodiment, the [weight/volume]% solubility of amitraz at room temperature is from about 24% to about 46%. In still other embodiments, the [weight/volume]% solubility of amitraz at room temperature in the solvent is from about 10% to about 60%, about 20% to about 60%, or about 10% to about 50%.

A fourth aspect of the invention provides a formamidine composition (e.g. amitraz) with enhanced odor dissipation after application or administration which comprises a veterinarily effective amount of formamidine and one or at least two aprotic solvents, preferably at least two polar aprotic solvents, or at least two solvents each with a dielectric constant of about 2 to about 30, including the solvents described above. As used herein, enhanced odor dissipation refers to the faster dissipation of the initial odor exhibited by the formulation within a period of time compared to the time required for dissipation of odor by formulations of the prior art. For example, in one embodiment of the fifth aspect of the invention, the odor dissipation occurs within about 5 to about 25 minutes. In another embodiment, the odor dissipation occurs within about 10 to about 15 minutes. In still another embodiment, the odor dissipation occurs within about 5 minutes to about 15 minutes, within about 10 minutes to about 25 minutes or within 15 minutes to about 25 minutes. In comparison, formamidine formulations of the prior art exhibit an odor that does not dissipate within 25 minutes.

In other embodiments, the formamidine composition with enhanced odor dissipation properties comprises one or more solvents with dielectric constants of about 2 to about 20, about 5 to about 30, or about 10 to about 30. More typically, the dielectric constant of the one or more solvents will be between about 2 to about 15 or about 2 to about 10.

In other embodiments, the formamidine composition with enhanced odor dissipation properties comprises one or more aprotic solvents, preferably one or more polar aprotic solvents, with dielectric constants of about 2 to about 20, about 5 to about 30, or about 10 to about 30. More typically, the dielectric constant of the one or more polar aprotic solvents will be between about 2 to about 15 or about 2 to about 10.

In one embodiment, the one or at least two solvents that improve the odor dissipation of formamidine compositions include, but are not limited to, an alkoxybenzene, carboxylic acid esters, aliphatic ketones, saturated aliphatic ketones, benzoic acid esters or mixtures thereof.

In another embodiment, the one or more solvents that improve the odor dissipation of formamidine compositions include, but are not limited to, aryl ethers including alkoxybenzene compounds; carboxylic acid esters, including esters of aliphatic and aromatic carboxylic acids such as benzoic acid esters, and compounds with multiple carboxylate groups; aliphatic ketones, cyclic ketones, or mixtures thereof.

In one embodiment, the one or at least two solvents that improve the odor dissipation of formamidine compositions include $C_1$-$C_4$-alkoxybenzene, $C_1$-$C_{10}$ carboxylic acid esters, phenyl carboxylic acid esters, carboxylic acid benzyl esters, carboxylic acid phenyl esters, benzyl carboxylic acid esters, $C_1$-$C_6$ saturated aliphatic ketones, $C_1$-$C_4$ benzoic acid esters and mixtures thereof.

In additional embodiment of the invention, the formamidine compositions with improved odor dissipation comprise one or at least two aprotic solvents each with a dielectric constant of about 2 to about 15 including, but not limited to, methoxybenzene (4.33), butyl acetate (5.0), benzyl acetate (5.0), methyl isobutyl ketone (13.1), ethyl benzoate (6.02), benzyl benzoate (4.8), octyl acetate and mixtures thereof. (dielectric constants in parentheses)

In still other embodiments, the dielectric constant of the one or more solvents is about 3 to about 10, about 3.5 to about 10, or about 4 to about 6.5.

In a preferred embodiment, the solvent is octyl acetate.

In another preferred embodiment, the at least two solvents in the formamidine compositions with improved odor dissipation is a mixture of butyl acetate and anisole or a mixture of butyl acetate and methyl isobutyl ketone.

A fifth aspect of the invention provides a composition for the treatment and/or prevention of a parasitic infestation in an animal comprising at least one (i.e. one or more) 1-arylpyrazole compound(s) and at least one formamidine compound(s) in combination with one or more pharmaceutically or veterinarily acceptable carrier(s) and optionally a crystallization inhibitor, wherein the 1-arylpyrazole compound (s) and the formamidine compound (s) may be together in the same carrier or each active compound may be in a separate carrier.

In one embodiment, the one or more 1-arylpyrazole compound(s) are in a first carrier and the formamidine compound(s) are in a second carrier, wherein the compounds and the first and second carriers are compartmentalized separately from each other and are not in fluid communication before administration.

In another embodiment of the fifth aspect of the invention, the one or more 1-arylpyrazole compound(s) and the formamidine compound(s) are in one common carrier.

It will be appreciated by those of skill in the art that the first carrier and the second carrier may be the same or different. For example, the first and second carriers may comprise the same solvent or may include different solvents or combinations of solvents.

In one embodiment of the fifth aspect of the invention, the composition comprises:

(a) at least one 1-arylpyrazole compound of formula (IB):

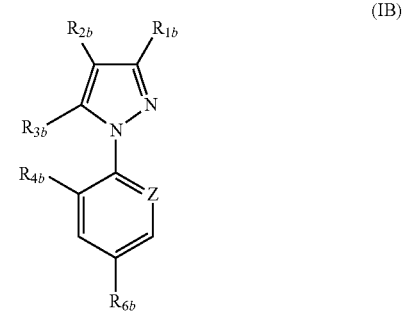

in which:
$R_{1b}$ is alkyl, CN or halogen;
$R_{2b}$ is $S(O)_n R_{14b}$ or 4,5-dicyanoimidazol-2-yl or haloalkyl;
$R_{14b}$ is alkyl or haloalkyl;
$R_{3b}$ is a hydrogen, halogen, —$NR_{7b}R_{8b}$, —$S(O)_m R_{9b}$, —$C(O)R_{9b}$, —$C(O)OR_{9b}$, alkyl, haloalkyl, —$OR_{10b}$ or an —$N$=$C(R_{11b})(R_{12b})$;

$R_{6b}$ is a halogen, haloalkyl, haloalkoxy, $S(O)_qCF_3$ or $SF_5$ group;

$R_{7B}$ and $R_{8B}$ independently represent a hydrogen, alkyl, haloalkyl, —C(O)alkyl, —S(O)$_r$CF$_3$, acyl or alkoxycarbonyl; or $R_{7b}$ and $R_{8b}$ can together form a divalent alkylene radical which is optionally interrupted by one or two divalent heteroatoms;

$R_{9b}$ is an alkyl or haloalkyl;

$R_{10b}$ is hydrogen, alkyl or haloalkyl;

$R_{11b}$ is hydrogen or alkyl radical;

$R_{12b}$ is an optionally substituted aryl or an optionally substituted heteroaryl group;

$R_{4b}$ and $R_{13b}$ represent, independently of one another, hydrogen, halogen CN or NO$_2$;

m, n, q and r represent, independently of one another, an integer equal to 0, 1 or 2;

Z represents a trivalent nitrogen atom or a C—$R_{13b}$ radical, the three other valencies of the carbon atom forming part of the aromatic ring; and (b) at least one formamidine compound comprises at least one compound of formula (II):

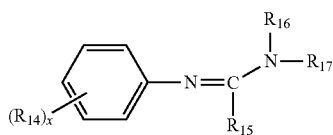

(II)

wherein:

x is an integer from 0-5;

$R_{14}$ is alkyl, halogen or —OC(=O)NR$_a$R$_b$, wherein R$_a$ and R$_b$ are independently hydrogen or alkyl;

$R_{15}$ is hydrogen or alkyl;

$R_{16}$ is hydrogen or alkyl;

$R_{17}$ is hydrogen, alkyl or

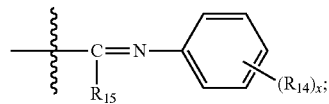

(c) one or more veterinarily acceptable carrier(s); and (d) optionally, at least one crystallization inhibitor.

In another embodiment of the fifth aspect of the invention, the 1-arylpyrazole(s) is a compound of formula (IB), wherein $R_{1b}$ is methyl, CN or halogen;

$R_{14b}$ is C$_1$-C$_6$-alkyl or C$_1$-C$_6$-haloalkyl;

$R_{3b}$ is a hydrogen, halogen, —NR$_{7b}$R$_{8b}$, —S(O)$_m$R$_{9b}$, —C(O)R$_{9b}$, —C(O)OR$_{9b}$, C$_1$-C$_6$ alkyl, C$_1$-C$_6$ haloalkyl, —OR$_{10b}$ or —N=C(R$_{11b}$)(R$_{12b}$);

$R_{7b}$ and $R_{8b}$ independently represent a hydrogen, C$_1$-C$_6$-alkyl, C$_1$-C$_6$-haloalkyl, —C(O)C$_1$-C$_6$-alkyl, —S(O)$_r$CF$_3$, C$_1$-C$_6$-acyl or C$_1$-C$_6$-alkoxycarbonyl radical; or $R_{7b}$ and $R_{8b}$ may together form a divalent alkylene radical which may be interrupted by one or two divalent hetero atoms selected from the group consisting of oxygen or sulfur;

$R_{9b}$ is a C$_1$-C$_6$-alkyl or C$_1$-C$_6$-haloalkyl radical;

$R_{10b}$ is a C$_1$-C$_6$-alkyl or C$_1$-C$_6$-haloalkyl radical or a hydrogen atom;

$R_{11b}$ is a C$_1$-C$_6$-alkyl radical or a hydrogen atom;

$R_{12b}$ is an optionally substituted phenyl or optionally substituted heteroaryl group wherein the substituents are selected from the group consisting of halogen, —OH, —O—C$_1$-C$_6$-alkyl, —S—C$_1$-C$_6$-alkyl, cyano and C$_1$-C$_6$-alkyl;

$R_{6b}$ is a halogen, C$_1$-C$_6$-haloalkyl, C$_1$-C$_6$-haloalkoxy, $S(O)_qCF_3$ or $SF_5$ group; and Z is a C—$R_{13b}$ radical.

In another embodiment of the fifth aspect of the invention, the 1-arylpyrazole(s) is a compound of formula (IB), wherein $R_{1b}$ is methyl, CN or halogen;

$R_{2b}$ is S(O)$_n$R$_{14b}$;

$R_{14b}$ is C$_1$-C$_6$-alkyl or C$_1$-C$_6$-haloalkyl;

$R_{3b}$ is —NR$_{7b}$R$_{8b}$;

$R_{7b}$ and $R_{8b}$ independently represent a hydrogen, C$_1$-C$_6$-alkyl, C$_1$-C$_6$-haloalkyl, —C(O)C$_1$-C$_6$-alkyl, —S(O)$_r$CF$_3$, C$_1$-C$_6$-acyl or C$_1$-C$_6$-alkoxycarbonyl radical;

$R_{6b}$ is a halogen, C$_1$-C$_6$-haloalkyl, or C$_1$-C$_6$-haloalkoxy;

m, n, q and r represent, independently of one another, an integer equal to 0 or 1; and Z is a C—$R_{13b}$ radical.

In still another embodiment of the fifth aspect of the invention, the 1-arylpyrazole(s) is a compound of formula (IB), wherein $R_{1b}$ is CN;

$R_{2b}$ is S(O)$_n$R$_{14b}$;

$R_{14b}$ is CF$_3$;

$R_{3b}$ is NR$_{7b}$R$_{8b}$;

$R_{7b}$ and $R_{8b}$ are hydrogen;

$R_{4b}$ and $R_{13b}$ are each Cl;

$R_{6b}$ is CF$_3$.

(this compound is also known as fipronil or 1-[2,6-dichloro-4-trifluoromethyl phenyl]-3-cyano-4-trifluoromethylsulfinyl-5-amino pyrazole).

In another embodiment of the fifth aspect of the invention, the formulation comprises at least one formamidine compound and at least one 1-arylpyrazole of formula (I) as described above, one or more pharmaceutically acceptable carrier(s), and optionally one or more crystallization inhibitors.

In another embodiment of the fifth aspect of the invention, the formulation comprises at least one formamidine compound of formula (II) described above and at least one 1-arylpyrazole compound of formula (I) described above, one or more pharmaceutically acceptable carrier(s), and optionally one or more crystallization inhibitors.

In another embodiment of the fifth aspect of the invention, the formulation comprises at least one 1-arylpyrazole of formula (I) wherein R$_1$ is cyano, —C(O)R$_8$, —C(O)OR$_8$, —C(O)NR$_9$R$_{10}$, —C(=NOH)NH$_2$, —C(=NNH$_2$), or —C(S)NH$_2$.

In another embodiment of the formulation, the 1-arylpyrazole(s) of formula (I) is provided wherein R$_3$ is alkyl or haloalkyl.

In one embodiment of the fifth aspect of the invention, the formulation comprises a 1-arylpyrazole(s) of formula (I) wherein:

R$_1$ is cyano, —C(O)R$_8$, —C(O)OR$_8$, —C(O)NR$_9$R$_{10}$, —C(=NOH)NH$_2$, —C(=NNH$_2$), or —C(S)NH$_2$; and R$_2$ is —SCN, 4-5-dicyanoimidazol-2-yl, or —S(O)$_m$R$_{11}$.

In another embodiment of the formulation, the 1-arylpyrazole(s) of formula (I) is provided wherein:

R$_1$ is cyano, —C(O)R$_8$, —C(O)OR$_8$, —C(O)NR$_9$R$_{10}$, —C(=NOH)NH$_2$, —C(=NNH$_2$), or —C(S)NH$_2$;

R$_2$ is —SCN, 4-5-dicyanoimidazol-2-yl, or —S(O)$_m$R$_{11}$; and

R$_3$ is alkyl or haloalkyl.

In still another embodiment of the fifth aspect of the invention, the 1-arylpyrazole(s) of formula (I) is provided wherein:

R$_1$ is cyano;

$R_2$ is —SCN, 4-5-dicyanoimidazol-2-yl, or —S(O)$_m$R$_{11}$;
$R_3$ is alkyl or haloalkyl;
$R_4$, $R_5$ and $R_7$ are independently hydrogen, or halogen; and
Z is C—R$_{13}$.

In another embodiment of the fifth aspect of the invention, the formulation comprises at least one 1-arylpyrazole(s) of formula (I) is provided wherein:
$R_1$ is cyano;
$R_2$ is —SCN, 4-5-dicyanoimidazol-2-yl, or —S(O)$_m$R$_{1i}$;
$R_3$ is C$_1$-C$_4$alkyl or C$_1$-C$_4$haloalkyl;
$R_6$ is halogen, haloalkyl or SF$_5$; and
Z is C—R$_{13}$.

In one embodiment of the fifth aspect of the invention, the formulation comprises at least one 1-arylpyrazole(s) of formula (I) wherein:
$R_1$ is cyano;
$R_2$ is —S(O)$_m$R$_{11}$;
$R_3$ is C$_1$-C$_4$alkyl, C$_1$-C$_4$haloalkyl, or NR$_9$R$_{10}$;
$R_4$, $R_5$ and $R_7$ are independently hydrogen, or halogen;
$R_6$ is halogen, C$_1$-C$_4$alkyl, C$_1$-C$_4$haloalkyl, or SF$_5$;
Z is C—R$_{13}$; and
$R_{13}$ is halogen or C$_1$-C$_4$haloalkyl.

In another embodiment of the fifth aspect of the invention, the formulation comprises at least one 1-arylpyrazole of formula (I) wherein:
$R_1$ is cyano;
$R_2$ is —S(O)$_m$R$_{11}$;
$R_3$ is methyl, ethyl, propyl, or C$_1$-C$_4$haloalkyl;
$R_4$ is halogen;
$R_5$ and $R_7$ are hydrogen;
$R_6$ is C$_1$-C$_4$haloalkyl;
Z is C—R$_{13}$;
$R_{11}$ is —CF$_3$, —CClF$_2$, or CFCl$_2$; and
$R_{13}$ is halogen.

In still another embodiment of the fifth aspect of the invention, the formulation comprises at least one 1-arylpyrazole of formula (I) wherein:
$R_1$ is cyano;
$R_2$ is —S(O)$_m$R$_{11}$;
$R_3$ is methyl or ethyl;
$R_4$ is chloro or fluoro;
$R_5$ and $R_7$ are hydrogen;
$R_6$ is —CF$_3$;
Z is C—R$_{13}$;
$R_{11}$ is —CFCl$_2$; and
$R_{13}$ is chloro or fluoro.

In another embodiment of the fifth aspect of the invention the formulation comprising at least one 1-arylpyrazole and at least one formamidine compound comprises at least one 1-arylpyrazole of formula (IA) as described above, or a salt thereof, a pharmaceutically or veterinarily acceptable carrier, and optionally at least one crystallization inhibitor.

In another embodiment of the fifth aspect of the invention, the formulation comprises at least one formamidine of formula (II) described above and at least one 1-arylpyrazole compound of formula (IA) described above, or salts thereof, a pharmaceutically or veterinarily acceptable carrier, and optionally at least one crystallization inhibitor.

In another embodiment of the fifth aspect of the invention, the formulation comprises at least one 1-aryl-5-alkyl pyrazole compound of formula (IA) wherein:
$R_{2a}$ is —S(O)$_m$R$_{11a}$;
$R_{3a}$ is methyl, or ethyl;
$R_{4a}$ is halogen;
$R_{6a}$ is C$_1$-C$_4$ haloalkyl;
$R_{13a}$ is halogen;
$R_{11a}$ is —CF$_3$, —CClF$_2$, or —CFCl$_2$; and
m is 0, 1 or 2.

In another embodiment of the fifth aspect of the invention, the formulation comprises at least one 1-aryl-5-alkyl pyrazole compound of formula (IA) wherein:
$R_{2a}$ is —S(O)$_m$R$_{11a}$;
$R_{3a}$ is methyl, or ethyl;
$R_{4a}$ is halogen;
$R_{6a}$ is C$_1$-C$_4$ haloalkyl;
$R_{13a}$ is halogen;
$R_{11a}$ is —CF$_3$, —CClF$_2$, or —CFCl$_2$; and
m is 0, 1 or 2.

In still another embodiment of the fifth aspect of the invention, the compound(s) of formula (IA) is a compound wherein:
$R_{2a}$ is —S(O)$_m$R$_{11a}$;
$R_{3a}$ is methyl;
$R_{4a}$ is —Cl;
$R_{6a}$ is —CF$_3$;
$R_{13a}$ is —F;
$R_{11a}$ is —CFCl$_2$; and
m is 0, 1 or 2.

In still another embodiment of the fifth aspect of the invention, the formamidine compound(s) in the formulation is a compound of formula (II), wherein
x is an integer from 1 to 3;
$R_{14}$ is C$_1$-C$_4$ alkyl, fluoro, chloro or bromo or —OC(=O)NR$_a$R$_b$,
wherein R$_a$ and R$_b$ are independently hydrogen or C$_1$-C$_4$ alkyl;
$R_{15}$ is hydrogen or C$_1$-C$_4$ alkyl;
$R_{16}$ is hydrogen or C$_1$-C$_4$ alkyl;
$R_{17}$ is hydrogen, C$_1$-C$_4$ alkyl; or

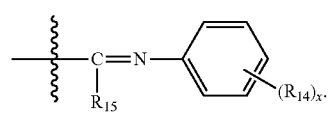

In another embodiment, the formamidine compound(s) is a compound of formula (II), wherein
x is an integer from 1 to 2;
$R_{14}$ is methyl, chloro or —OC(=O)NR$_a$R$_b$,
wherein R$_a$ is hydrogen and R$_b$ is methyl;
$R_{15}$ is hydrogen or methyl;
$R_{16}$ is hydrogen or methyl;
$R_{17}$ is hydrogen, methyl; or

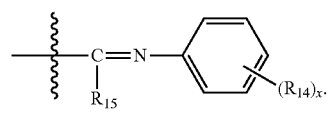

In a further embodiment of the fifth aspect of the invention, the formamidine compound(s) is selected from the group consisting of:

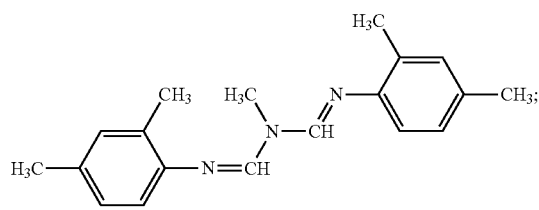

amitraz

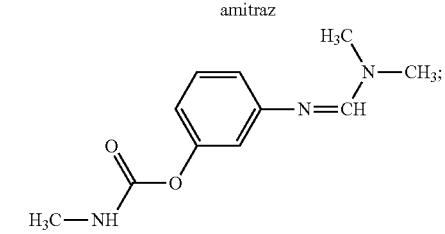

formetanate

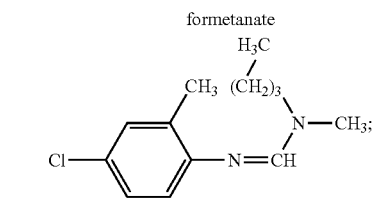

chloromebuform

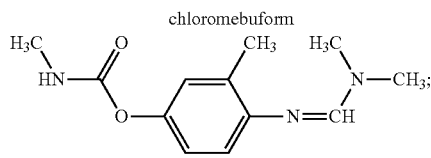

formparanate

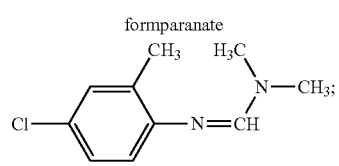

chlordimeform and mixtures thereof.

In another embodiment of the fifth aspect of the invention, the formamidine compound is:

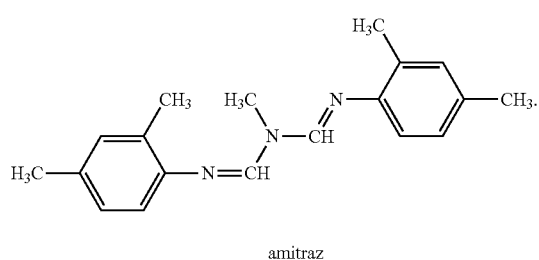 [SMILES: Cc1ccc(N=CN(C)/C=N/c2ccc(C)cc2C)c(C)c1]

amitraz

In a preferred embodiment of the fifth aspect of the invention, the 1-arylpyrazole is fipronil and the formamidine compound is amitraz.

In another preferred embodiment of the fifth aspect of the invention, the 1-arylpyrazole compound(s) is in one carrier system and the formamidine compound(s) is in a separate second carrier system.

A sixth aspect of the invention provides composition for the treatment and prevention of parasites in an animal in need thereof which comprises:

(a) at least one formamidine compound of formula (II):

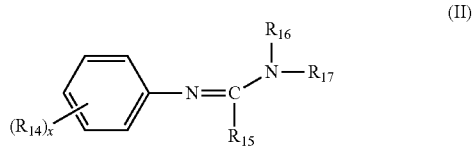

(II)

wherein:
x is an integer from 0-5;
$R_{14}$ is alkyl, halogen or —OC(=O)$NR_aR_b$, wherein $R_a$ and $R_b$ are independently hydrogen or alkyl;
$R_{15}$ is hydrogen or alkyl;
$R_{16}$ is hydrogen or alkyl;
$R_{17}$ is hydrogen, alkyl or

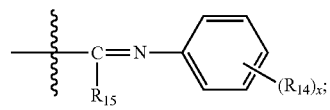

and
(b) a veterinarily acceptable carrier.

In one embodiment of the sixth aspect of the invention, the formamidine(s) of formula (II) is provided wherein:
$R_{14}$ is $C_1$-$C_4$alkyl or halogen;
$R_{15}$ is hydrogen or $C_1$-$C_4$alkyl; and
$R_{16}$ is hydrogen or $C_1$-$C_4$alkyl.

In another embodiment of the sixth aspect of the invention, formamidine(s) of formula (II) is provided wherein $R_{17}$ is

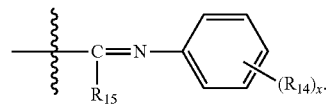

In still another embodiment, the formulation comprises formamidine compound(s) wherein:
x is an integer from 1, 2 or 3;
$R_{14}$ is $C_1$-$C_4$alkyl, halogen or —OC(=O)$NR_aR_b$, wherein $R_a$ and $R_b$ are independently hydrogen or $C_1$-$C_4$alkyl;
$R_{15}$ is hydrogen or $C_1$-$C_4$alkyl;
$R_{16}$ is hydrogen or $C_1$-$C_4$alkyl;
$R_{17}$ is hydrogen, $C_1$-$C_4$alkyl or

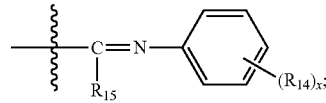

In another embodiment of the sixth aspect of the invention, the composition has enhanced odor dissipation following application or administration.

In a still another embodiment of the sixth aspect of the invention, the composition has enhanced stability compared to compositions comprising formamidines of the prior art.

In a another embodiment of the sixth aspect of the invention, the composition comprises one or at least two aprotic solvents each with a dielectric constant of about 2 to about 30.

In a preferred embodiment, the composition comprises octyl acetate.

In another preferred embodiment of the sixth aspect of the invention, the composition comprises at least two solvents in a mixture of butyl acetate and anisole or a mixture of butyl acetate and methyl isobutyl ketone.

In another preferred embodiment of the sixth aspect of the invention, the formamidine compound (a) is amitraz.

Methods of Treatment

In an seventh aspect of the invention, a method for preventing or treating a parasite infestation/infection in an animal is provided, comprising administering a composition comprising an effective amount of at least one 1-arylpyrazole compound of formula (I), (IA) or (IB) together with a pharmaceutically or veterinarily acceptable carrier and optionally a crystallization inhibitor. The compositions or formulations of the invention have long-lasting efficacy against fleas and ticks and are also able to quickly eradicate flea and tick infestations.

By "treating" or "treat" or "treatment" is intended the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

In one embodiment, a formulation comprising a 1-arylpyrazole compound of formula (IA) has an efficacy of about 90% or greater against fleas 30 days after application. In another embodiment, a formulation comprising a 1-arylpyrazole compound of formula (IA) has an efficacy of about 99% or greater against fleas 51 days or 58 days after application.

In still another embodiment, a formulation comprising a 1-arylpyrazole compound of formula (IA) has an efficacy of about 85% or greater against ticks 23 days after application. In yet another embodiment, a formulation comprising a 1-arylpyrazole compound of formula (IA) has an efficacy of about 90% or greater against ticks 44 days or 58 days after application. In still another embodiment, a formulation comprising a 1-arylpyrazole compound of formula (IA) has an efficacy of about 99% or greater against ticks 58 days after application.

In another embodiment, a formulation comprising a 1-arylpyrazole of formula (IA) is able to eradicate a flea infestation (as tested in the examples herein) more quickly than 1-arylpyrazole compounds of the prior art. In an embodiment, the 1-arylpyrazole compound is able to eradicate a flea infestation in less than 10 hours or less than 9 hours after application.

In another embodiment, a formulation comprising a 1-arylpyrazole of formula (IA) is able to eradicate a tick infestation (as tested in the examples herein) in less than 20 hours after application.

In one embodiment, the invention provides a method for preventing or treating an ectoparasitic infestation/infection in an animal. In another embodiment, the invention provides a method for preventing or treating an endoparasitic infestation/infection in an animal. In certain embodiments for treating an endoparasitic infestation, the compositions of the invention may include an additional anthelmintic agent.

In one embodiment of the method, the composition comprising the 1-arylpyrazole compound (s) and the carrier exhibits enhanced stability and/or enhanced efficacy.

An eighth aspect of the invention provides a method for treating or preventing a parasite infestation in an animal in need thereof comprising administering an effective amount of a composition of the invention that comprises at least one 1-arylpyrazole compound, at least one formamidine compound or at least one formamide compound, or combinations thereof, and optionally at least one crystallization inhibitor; wherein the 1-arylpyrazole is administered in a first carrier and the formamidine compound is administered in a second carrier, and wherein the first carrier is isolated from the second carrier and not in fluid communication with the second carrier within the administration device.

In one embodiment of the eighth aspect of the invention, the 1-arylpyrazole compound (s) is a compound of formula (I), (IA) or (IB). In another embodiment of the eighth aspect of the invention, the formamidine compound (s) is a formamidine compound of formula (II).

It will be appreciated by those of skill in the art that the method of the invention encompasses administering the 1-arylpyrazole compound(s) separately from the formamidine compound as well as administering the 1-arylpyrazole compound(s) together with the formamidine compound(s), although the two compounds may be in separate carriers. For example, the 1-arylpyrazole compound(s) may be administered at the same location on the animal as the formamidine compound(s) or the 1-arylpyrazole compound(s) may be administered at a different location on the animal. Furthermore, the 1-arylpyrazole compound(s) may be administered by one mode of administration (e.g. topical, oral, parenteral, etc.) while the formamidine compound(s) may be administered by a different mode of administration. The method of the invention also encompasses the administration of the 1-arylpyrazole compound(s) simultaneously with the formamidine compound(s) or sequentially with the formamidine compound(s) (i.e. at different times).

In one embodiment, the first carrier comprises a first solvent system and the second carrier comprises a second solvent system that is different from the first solvent system.

In one embodiment of the eighth aspect of the invention, the method comprises administering the 1-arylpyrazole (s) separately from the formamidine compound(s).

In another embodiment, the 1-arylpyrazole (s) is administered simultaneously with the formamidine compound(s).

In yet another embodiment of the eighth aspect of the invention, the arylpyrazole(s) is administered separately and simultaneously with the formamidine compound(s).

In a ninth aspect of the invention, a method for preventing or treating a parasite infestation in an animal is provided, comprising administering an effective amount of at least one 1-arylpyrazole compound and an effective amount of at least one formamidine or formamide compound to the animal in need thereof, wherein the compounds are administered via a multiple-cavity container, wherein a first cavity is used to store the veterinarily effective amount of one or more formamidine compounds, formamide compounds, or mixtures thereof, in a first veterinarily acceptable carrier and administer the composition to the animal therefrom; and wherein a second cavity is used to store the veterinarily effective amount of a 1-arylpyrazole compound in a second veterinarily acceptable carrier and administer the composition to the animal therefrom. The multiple cavity container may have two or more cavities, that may contain different active agents and different carriers. Alternatively, the multiple cavity containers may be used to include multiple doses of the same active agent for easy administration. In one embodiment, the multiple cavity container is a dual-cavity container. Other embodiments include multiple cavity containers with three, four, or more cavities. As discussed below, the multiple cavity containers will comprise delivery ports for administering the compositions.

In one embodiment, the multiple cavity container is a dual cavity container that comprises:

a first cavity defined by a front wall and a divider wall; and
a second cavity defined by a rear wall the divider wall;
wherein the first cavity is used to store and administer a veterinarily effective amount of at least one formamidine compounds, at least one formamide compounds, or mixtures thereof; and wherein the second cavity is used to store and administer a veterinarily effective amount of at least one 1-arylpyrazole compound.

In one embodiment of the ninth aspect of the invention, an effective amount of the active compounds of the invention are administered via a dual-cavity container comprising:

a first cavity defined by a front wall and a divider wall;
a second cavity defined by a rear wall and a divider wall;
wherein a veterinarily effective amount of at least one 1-arylpyrazole compound is administered via the first cavity; and wherein a veterinarily effective amount of at least one formamidine compound is administered via the second cavity.

In another embodiment of the ninth aspect of the invention, a method is provided wherein an effective amount of fipronil is administered via a first cavity of a multiple-cavity container and an effective amount of a formamidine compound is administered via a second cavity of a multiple-cavity container.

In still another embodiment of the ninth aspect of the invention, a method is provided wherein an effective amount of a 1-arylpyrazole compound of formula (I), (IA) or (IB) is administered via a first cavity of a dual-cavity container, and an effective amount of a formamidine of formula (II) is administered via a second cavity of a dual cavity container.

In still another embodiment of the ninth aspect of the invention, a method is provided wherein an effective amount of fipronil is administered to the animal via a first cavity of a dual-cavity container, and an effective amount of amitraz is administered via a second cavity of a dual-cavity container.

In yet another embodiment of the ninth aspect of the invention, a method is provided wherein an effective amount of a 1-arylpyrazole compound of formula (IA) is administered to the animal via a first cavity of a dual-cavity container, and an effective amount of amitraz is administered via a second cavity of a dual-cavity container.

Other dual chamber dispensers which can be incorporated into the invention include but are not limited to the dispensers referred to in U.S. Pat. Nos. 5,318,203; 5,353,961; 6,161,729; 6,230,935, 6,883,295 and U.S. Design Ser. No 404,972, the disclosures of which are hereby incorporated by reference in their entirety.

In some embodiments, a composition of the invention may be delivered from a container having two or more cavities. Each cavity may include a component of the composition. For example, a container may include two distinct cavities, three distinct cavities or more. Each cavity may include one or more components of the composition, which may be in the same or different carriers. This aspect of the invention allows for the administration of combination of active compounds that may not be compatible together in the same carrier, or for the administration of compounds that require different carriers and/or excipients to provide sufficient stability and/or efficacy.

As discussed above, it has been found that formulations comprising both a 1-arylpyrazole compound and a formamidine compound present together in certain carriers may not have sufficient storage shelf lives. Such a situation is problematic for commercial products that may be stored at ambient conditions for extended periods of time (months to years). Therefore, the compositions and methods of the invention that provide for the administration of a 1-arylpyrazole compound and a formamidine compound via a dual cavity container are particularly useful because they allow the administration of highly efficacious compositions for treating parasitic infestations and also provide for an extended storage shelf life.

As shown in FIG. 1 some embodiments of the dual-cavity container may include container 10 having thermoformed dual cavities, upper cavity 12 and lower cavity 14. Container 10 may include front wall 16, rear wall 18, and divider wall 20 which may define the cavities of the container. For example, as shown in FIG. 1, the front wall, rear wall and divider wall define a dual-cavity container.

In some embodiments, divider wall 20 may be thinner than either front wall 16 or rear wall 18. For example, divider wall 20 may have a thickness in a range from about 5% to about 80% of either of the rear wall or front wall. Some embodiments may include a divider wall having a thickness in a range from about 20% to about 70% of either the rear wall or the front wall. Typically, the divider wall will have a thickness of from about 30% to about 70% or from about 40% to about 60% of either the front or rear wall. In another embodiment, the divider wall has a thickness of about 10% to about 40% of either of the rear wall or front wall. Alternately, some embodiments may include a divider wall having a thickness greater than a front wall, a rear wall and/or both the front and rear walls.

The front wall and the rear wall may be constructed from materials including, but not limited to films, rigid monolayers, laminate rigid films and/or any materials known in the art. For example, suitable materials include, but are not limited to, polyethylene terephthalate (PET), amorphous polyethylene terephthalate (APET), polyethylene terephthalate glycol (PETG) or crystalline polyethylene terephthalate (CPET), polyvinyl chloride (PVC), polypropylene (PP) polyethylene (PE), polyamide (PA), cycloolefin copolymers such as those known under the tradename COC®, poly acrylonitrile (PAN) such as known under the tradename BAREX®, and fluoropolymer or poly chlorotrifluoroethylene (PCTFE such as that as known under the tradename ACLAR®.

The divider wall may be constructed from materials including, but not limited to barrier films, flexible monolayers, laminate flexible films and/or any materials known in the art. For example, it includes polyester (PET), polypropylene (PP) polyethylene (PE), ethyl vinyl alcohol (EVOH), ethyl vinyl acetate (EVA), polyamide (PA), poly acrylonitrile (PAN) such as known under the tradename BAREX®, fluoropolymer or poly chlorotrifluoroethylene (PCTFE such as that as known under the tradename ACLAR® and aluminium foil. Preferably, the aluminium foil has a thickness of less than 60 µm.

U.S. Pat. No. 6,260,735 to Fuquen, and Published International Application WO 2001/087736, both incorporated herein by reference in their entirety, describes combinations of suitable construction material for dual chamber sachet. These materials are also suitable for the multiple cavity containers of the present application. In particular, this publication describes that suitable combinations of materials of construction for the front and rear wall including PET/Aluminum Foil/polyacrylonitriie (BAREX®), PET/Aluminum Foil/low density polyethylene (LDPE), Bi-Orientated polypropylene (BOPP)/Aluminum Foil/BAREX®, BOPP/Aluminum Foil/LDPE and LDPE/ethylene-vinyl alcohol polymer (EVOH)/

LDPE, PET/EVOH/LDPE, BOPP/EVOH/LPDE, LPDE Based Monolayer or Polyefins Blend, Sealable PET Based Monolayer, PET/PE/Sealable PET, PET/Foil/Sealable PET, Nylon/Foil/PE, and Nylon/PE/Sealable PET.

In addition to the material combinations described above, other suitable combinations of construction materials for the multiple containers of the invention include, but are not limited to, PP/PE and PP/PE-EVOH-PE and PP/PP and PP/BAREX® and COC®/PE and COC®/PE-EVOH-PE and COC®/PP and COC/BAREX® and ACLAR®/APET/PE and ACLAR®/APET/PE-EVOH-PE and ACLAR®/APET/PP and ACLAR®/APET/BAREX® and ACLAR®/PETG/PE and ACLAR®/PETG/PE-EVOH-PE and ACLAR®/PETG/PP/and ACLAR®/PETG/BAREX® and ACLAR®/PVC/PE and ACLAR®/PVC/PE-EVOH-PE and ACLAR®/PVC/PP and ACLAR®/PVC/BAREX®.

For the divider wall U.S. Pat. No. 6,260,735 describes the following material combinations: LPDE Based Or Polyefins Blend Monolayer, BAREX® Monolayer, LDPE/Aluminum Foil/LDPE, BAREX®/Aluminum Foil/BAREX® LDPE/EVOH/LDPE, Sealable PET/PE/Sealable PET, Sealable PET/Foil/Sealable PET, and PE/Nylon/PE. Additional combinations of materials suitable for the divider wall of the container of the present invention include, but are not limited to, PE-EVOH-PE:Alu foil/PE-EVOH-PE and PE-EVOH-EVA-PE/Alu foil/PE-EVA-EVOH-PE and PP/Alu foil/PP and PP/PE/Alu foil/PE/PP and PE/ACLAR®/PE and PP/ACLAR®/PP and BAREX®/ACLAR®/BAREX® and PE-EVOH-PE/PA/PE-EVOH-PE.

The walls may be coupled along a part of their perimeter to define the cavities. For example, the walls may be bonded together along the perimeter.

FIG. 1 depicts upper cavity 12 and lower cavity 14 having substantially the same proximal ends 22 and distal ends 24. Alternately, some embodiments may include ends which vary. For example, FIG. 2 shows upper cavity 12 being shorter at distal end 24 than distal end 24' of lower cavity 14.

Figure 2:
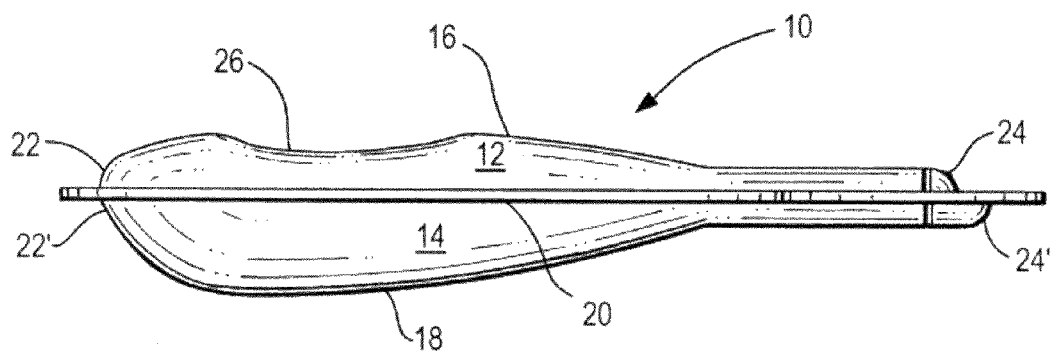
FIG. 2 is a side view of an embodiment of a container.
Figure 3:
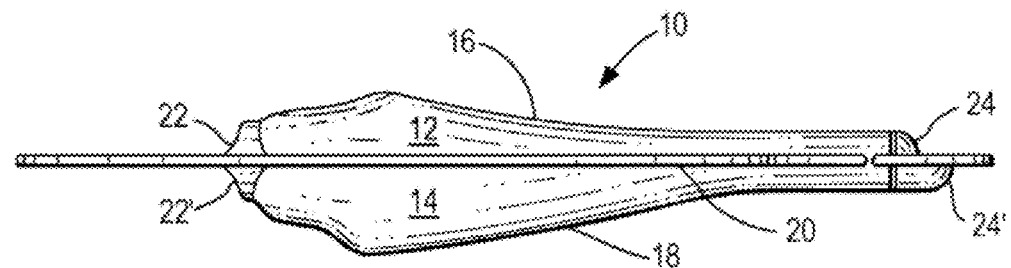
FIG. 3 is a side view of an embodiment of a container.
Figure 4:
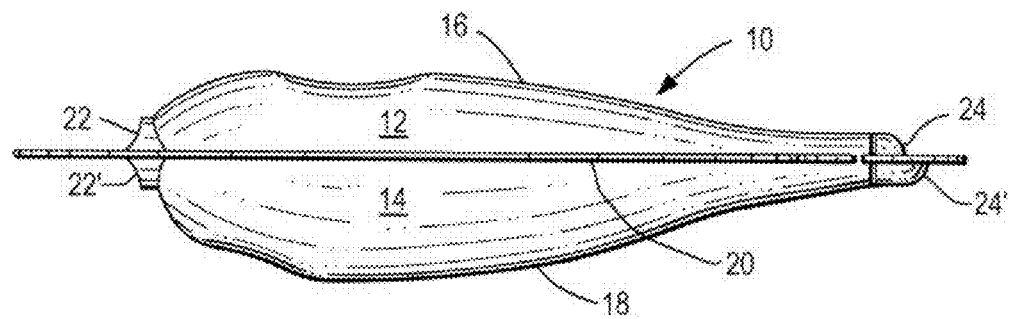
FIG. 4 is a side view of an embodiment of a container.

As shown in FIGS. 1-4, cavities 12, 14 may have different volumes. For example, FIG. 2 depicts upper cavity 12 having a smaller volume than lower cavity 14.

In some embodiments, a multi-cavity container may be used to deliver a liquid, a paste, a cream, powder, and/or granules. Multi-cavity containers may be to deliver drugs, cosmetics, food, household supplies, shampoos, conditioners, detergent, and/or adhesives. In an alternate embodiment, two or more components may be delivered by squeezing or pressing the external wall of the multi-cavity container. The components in the cavities may differ. For example, in FIGS. 1-4, upper cavity 12 may include a component which differs from lower cavity 14. In alternate embodiments, upper cavity 12 and lower cavity 14 may include substantially similar components.

As shown in FIG. 2, container 10 may include indenture 26. Indenture 26 may be positioned to allow for uniform delivery of the components. For example, indenture 26 may positioned on front wall 16 defining upper cavity 12. In some embodiments, there may be an indent positioned on both the front and rear walls. Indentures may be shaped to conform to a finger. Indentures may also be shaped to conform to a thumb. In some embodiments, indentures may allow for improved gripping.

Container 10 may include transparent external walls. In some embodiments, the front and rear walls may be configured to allow for accurate and full squeezing. In some embodiments, a multi-cavity container may be configured to dispense without any tilt, bend, and/or movement after opening.

Figure 5:
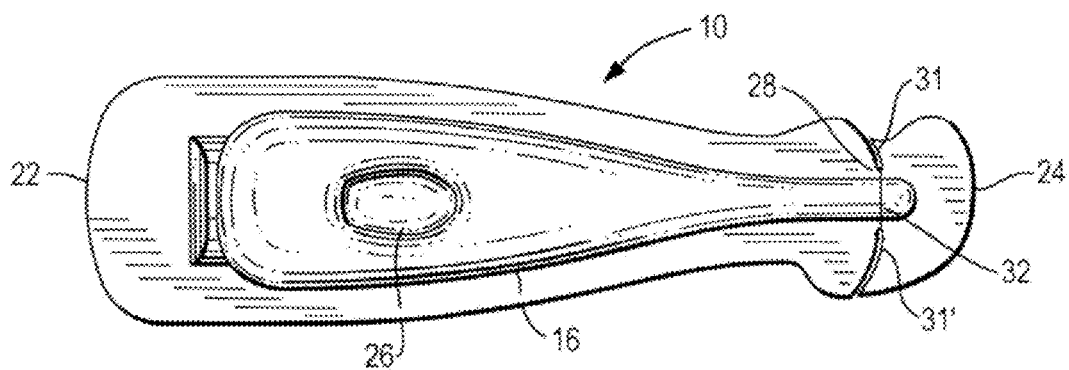
FIG. 5 is a top view of an embodiment of a container.

FIG. 5 depicts opening mechanism 28. Opening mechanism 28 may include but is not limited to a fracture line 32, a die cut, a perforation or any other design known in the art. In some embodiments as shown in FIG. 5, opening mechanism may be a die cut. Opening mechanism 28 may include one half moon shape 31. For example, a half moon shaped die cut may be made. In some embodiments, two half moon shaped die cuts 31 and 31' may be made perpendicular to a fracture line 32.

Figure 6:
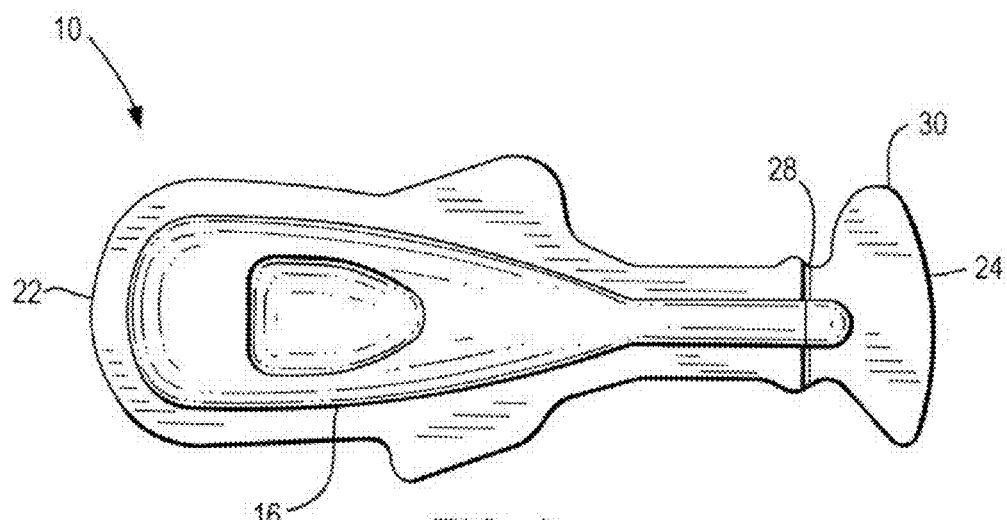
FIG. 6 is a top view of an embodiment of a container.
Figure 7:
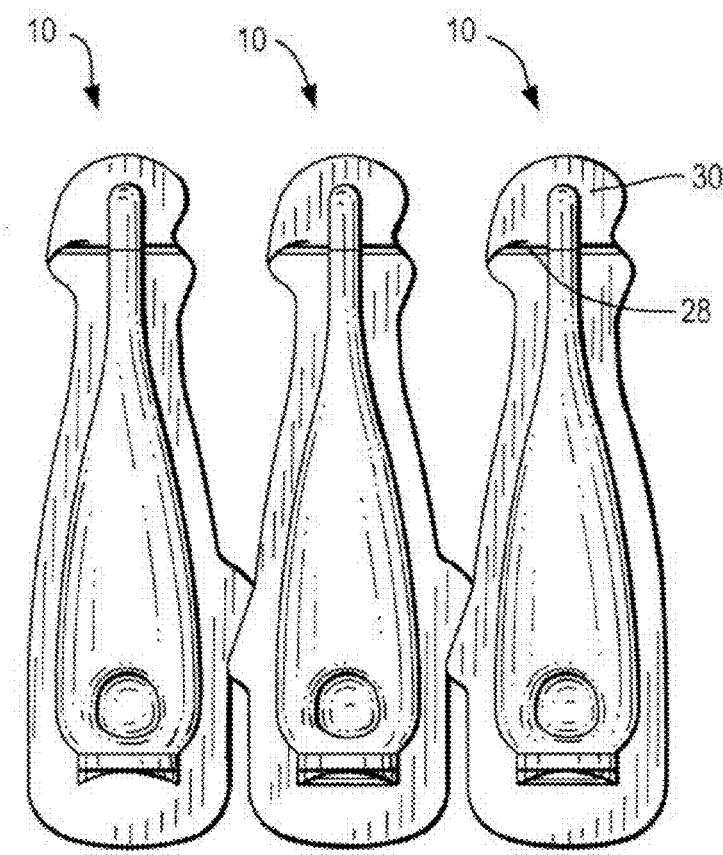
FIG. 7 is a top view of an embodiment of a strip of 3 containers.
Figure 8:
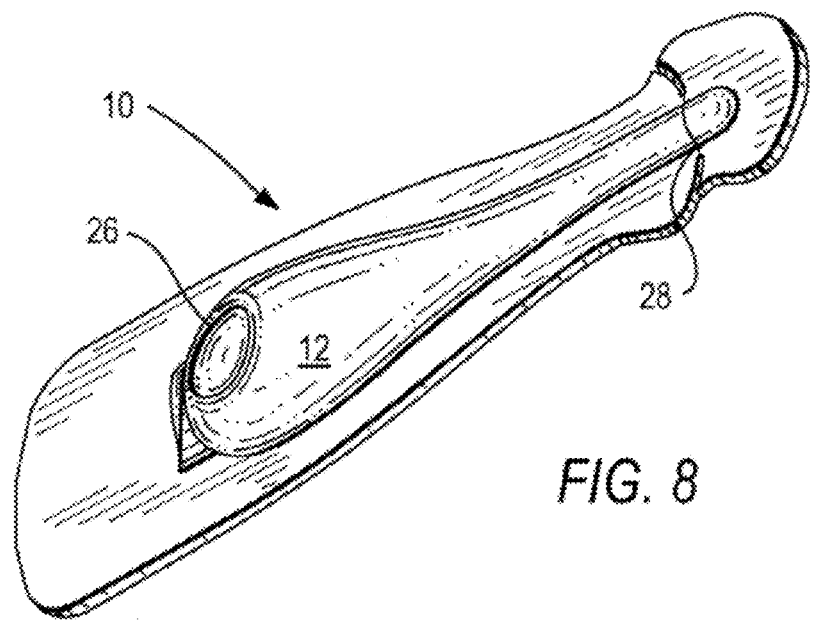
FIG. 8 is a 3CAD view top view of an embodiment of an individual small container.
Figure 9A:
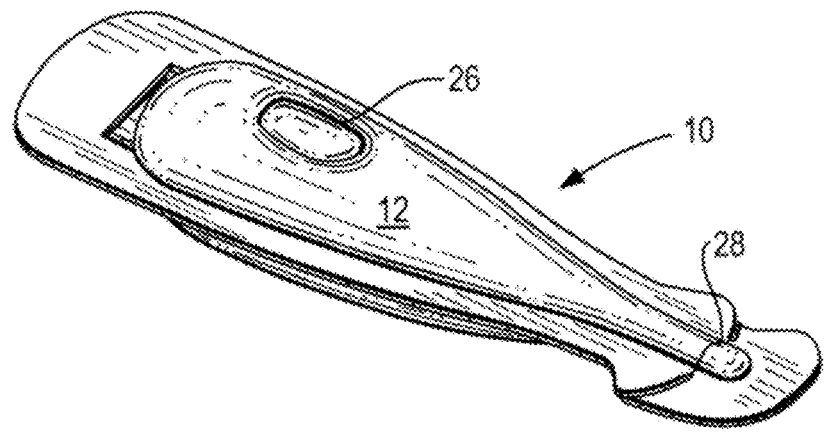
FIGS. 9a and 9b are 3CAD views of an embodiment of an individual large container.
Figure 9B:
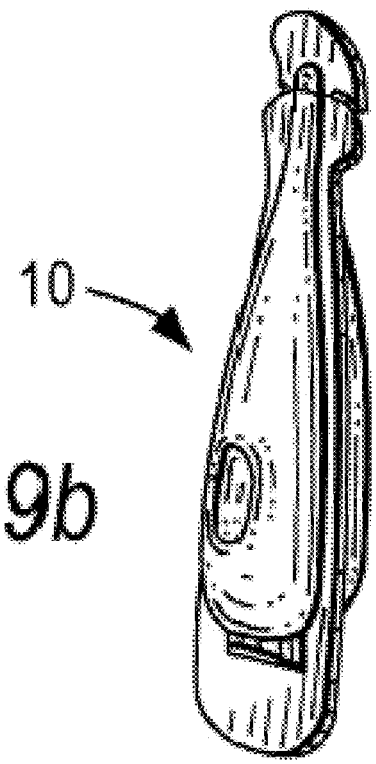

Alternately, an opening mechanism may have any geometry including but not limited to a line, a curve, or any geometry known in the art. The opening mechanism may tear a divider wall with no elongation. Further, the opening mechanism may be configure so that there are no sharp edges to the standard perpendicular connection between fracture line and perimeter of rigid front/rear walls. For example, FIG. 6 depicts opening mechanism 28 as a line. As shown in FIGS. 6-8, some embodiments may include tip 30 which may be twisted off along opening mechanism 28.

In some embodiments, a multi-cavity container may be configured to dispense without any tilt, bend, and/or movement after opening.

Some embodiments may include marks to position front and rear walls prior to coupling. For example, materials for the construction of the walls may be preprinted with a printing mark to customize each side with perfect positioning.

As shown in FIG. 7, a strip of containers may be connected prior to use.

A container may be constructed from a central ribbon for the divider wall and an external ribbon for the front and rear walls. A thermoforming station may form the front and rear walls prior to a feeding station delivering the central ribbon. Then, the wall perimeters may be coupled together, for example, by bonding or welding. The thermoforming process is a very well known process, and has been described in U.S. Pat. Nos. 5,223,073, 6,883,295, and in International Application Publication Nos. WO 2004/069658 A2, WO 2005/094330 and WO 2008/065512, all incorporated herein by reference in their entirety. In addition, some embodiments may include a cooling period in the thermoforming station prior to coupling the wall perimeters.

Some embodiments may include positioning the central ribbon to extend beyond the external ribbon. Positioning the ribbons in this manner may ensure a complete seal between the cavities.

A tenth aspect of the invention is a kit for the treatment or prevention of a parasitic infestation in an animal, comprising one or more 1-arylpyrazole compound(s) in a first veterinarily acceptable carrier, one or more formamidine compound(s) in a second veterinarily acceptable carrier, and a multiple cavity container; wherein the one or more 1-arylpyrazole compound(s) in a first veterinarily acceptable carrier is in a first cavity of the multiple cavity container and the one or more formamidine compound(s) in a second veterinarily acceptable carrier is in a second cavity of the multiple cavity container; and wherein the first cavity is defined by a front wall and a divider wall; and the second cavity defined by a rear wall the divider wall.

As discussed above, it has been surprisingly been found that compositions comprising formamidine compounds in combination with some 1-arylpyrazole compounds in certain solvent carriers do not have sufficient storage shelf lives for commercial use. The inventive kit described herein allow for the long term storage and subsequent administration of compositions comprising 1-arylpyrazoles and formamidines. Furthermore, certain synergistic compositions of 1-arylpyrazoles and amitraz may be stored and administered using the kit without degradation for long periods of time, allowing for the superior control of parasites in animals.

The kit may include any of the 1-arylpyrazle compositions described above in one or more of the cavities, including any of the veterinarily acceptable carriers previously described.

In one embodiment, the first veterinarily acceptable carrier that is combined with the 1-arylpyrazole compound(s) includes, but is not limited to, $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

In another embodiment, the first veterinarily acceptable carrier includes, but is not limited to, acetone, acetonitrile, benzyl alcohol, ethanol, isopropanol, diisobutyl adipate, diisopropyl adipate (also known as CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, butyl acetate, octyl acetate, propylene carbonate, butylene carbonate, dimethyl sulfoxide, amides including dimethylformamide and dimethylacetamide, or any combination thereof.

In another embodiment, the second veterinarily acceptable carrier includes, but is not limited to, aryl ethers including alkoxybenzene compounds; carboxylic acid esters, including aliphatic and aromatic carboxylic acids such as benzoic acid esters, and compounds with multiple carboxylate groups; aliphatic ketones, saturated aliphatic ketones, cyclic ketones, or mixtures thereof.

In yet another embodiment, the second veterinarily acceptable carrier includes, but is not limited to, $C_1$-$C_{10}$ carboxylic acid esters, phenyl carboxylic acid esters, carboxylic acid benzyl esters, benzoic acid $C_1$-$C_4$ alkyl esters, $C_1$-$C_6$ saturated aliphatic ketones, and mixtures thereof.

In still another embodiment, the second veterinarily acceptable carrier includes, but is not limited to, methoxybenzene, butyl acetate, benzyl acetate, methyl isobutyl ketone, ethyl benzoate, benzyl benzoate, octyl acetate or mixtures thereof.

In another embodiment, the second veterinarily acceptable carrier includes one or more solvent(s) with a dielectric constant of about 2 to about 30. In other embodiments of the invention, the second veterinarily acceptable carrier comprises a solvent with a dielectric constant of about 2 to about 40, 2 to about 20, 5 to about 30, or 10 to about 30.

In still other embodiments, the second veterinarily acceptable carrier comprises one or more solvents with a dielectric constant of about 2 to about 15 or about 3 to about 10. In still another embodiment, the dielectric constant of the one or more solvents is about 3.5 to about 10. In another embodiment, the dielectric constant of the one or more solvents is about 4 to about 6.5.

In another embodiment, the second veterinarily acceptable carrier includes one or more aprotic solvents, preferably polar aprotic solvents, with dielectric constants of about 2 to about 30. In other embodiments of the invention, the second veterinarily acceptable carrier comprises one or more aprotic solvent(s) with a dielectric constant of about 2 to about 40, 2 to about 20, 5 to about 30, or 10 to about 30.

In still other embodiments, the second veterinarily acceptable carrier comprises one or more aprotic solvent(s) with a dielectric constant of about 2 to about 15 or about 3 to about 10. In still another embodiment, the dielectric constant of the one or more aprotic solvent(s) is about 3.5 to about 10. In another embodiment, the dielectric constant of the one or more aprotic solvent(s) is about 4 to about 6.5. In some preferred embodiments, the solvents will be polar aprotic solvents with dielectric constants in the ranges described above.

In another embodiment, the solvent(s) with a dielectric constants of about 2 to about 30 comprised by the second veterinarily acceptable carrier will contain less than about 0.5% or less than about 0.3% (w/w) water. In other embodiments, the solvent with a dielectric constant of about 2 to about 30 will typically contain less than 0.2% (w/w) water. Preferably, the solvent will contain less than about 0.1%, or less than about 0.05% or less than about 0.025% (w/w) water. In other embodiments, the solvent will contain from about 0.0001% (w/w) to about 0.5% (w/w) water. More typically, the solvent with a dielectric constant of about 2 to about 30 will contain about 0.0001% to about 0.3%, about 0.001% to about 0.3%, about 0.001% to about 0.1% or about 0.001% to about 0.05% (w/w) water. Preferably, the solvent will contain from about 0.001% to about 0.025% (w/w) water.

The compositions of the invention can be in a variety of forms suitable for different forms of administration including, but are not limited to, oral formulations, injectable formulations, and topical, dermal or subdermal formulations.

The compositions of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874, which are incorporated herein by reference in their entirety, to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides. In another embodiment of the oily phase, the triglycerides are medium-chain triglycerides, for example $C_8$-$C_{10}$ caprylic/capric triglyceride. Another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, the ratio will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889, both of which are incorporated herein by reference. In addition to the active agent of the invention, the paste can also contain fumed silica; a viscosity modifier; a carrier; optionally, an absorbent; and optionally, a colorant, stabilizer, surfactant, or preservative.

The process for preparing a paste formulation comprises the steps of:

(a) dissolving or dispersing the active agent into the carrier by mixing;

(b) adding the fumed silica to the carrier containing the dissolved active agent compound and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste.

The above steps are illustrative, but not limiting. For example, step (a) can be the last step.

In one embodiment of the formulation, the formulation is a paste containing the active agent compound, fumed silica, a viscosity modifier, an absorbent, a colorant; and a hydrophilic carrier which is a triacetin, a monoglyceride, a diglyceride, or a triglyceride. The paste may also include a viscosity modifier including, but is not limited to, PEG 200, PEG 300, PEG 400, PEG 600, monoethanolamine, triethanolamine, glycerol, propylene glycol, polyoxyethylene (20) sorbitan mono-oleate (polysorbate 80 or Tween 80), or polyoxamers (e.g., Pluronic L 81); an absorbent including, but not limited to, magnesium carbonate, calcium carbonate, starch, or cellulose and its derivatives.

Colorants may be added to the inventive formulations. Colorants contemplated by the present invention are those commonly known in the art. Specific colorants include, for example, dyes, FD&C Blue #1 Aluminum Lake, caramel, colorant based upon iron oxide or a mixture of any of the foregoing. Especially preferred are organic dyes and titanium dioxide. Preferred ranges include from about 0.5% to about 25%.

The compositions may be in the form of a sterile injectable solutions or aqueous or oleagenous suspensions. These suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions. Topical application of an inventive compound or of a composition including at least one inventive compound among active agent(s) therein, a spot-on composition, can allow for the inventive compound to be distributed through the glands (e.g. sebaceous glands) of the animal and/or allow active agent(s) to achieve a systemic effect (plasma concentration) or throughout the haircoat. When the compound is distributed throughout glands, the glands can act as a reservoir, whereby there can be a long-lasting, e.g. 1-2 months effect or longer. Cotchet and co-workers reported the distribution of fipronil, a 1-arylpyrazole compound, to the stratum corneum, the viable epidermis and the sebaceous glands and epithelial layers of beagle dogs after spot-on administration (see Cochet et al., *Eur. J. Drug Metab. Pharmacokinet.*, 1997, 22(3), 211-216). Using $^{14}$C radiolabeled drug, the publication demonstrated that fipronil is displaced from the point of application and distributed to the whole skin, where it was persistently detected for up to 56 days after treatment. Spot-on formulations are typically applied in a localized region which refers to an area other than the entire animal. In one embodiment of a localized region, the location is between the shoulders. In another embodiment, the localized region is a stripe, e.g. a stripe from head to tail of the animal.

Pour-on formulations are described, for example, in U.S. Pat. No. 6,010,710, which is incorporated herein by reference. The pour-on formulations are advantageously oily, and generally comprise a diluent or vehicle and also a solvent (e.g. an organic solvent) for the active ingredient if the latter is not soluble in the diluent. Pour-on formulation may be administered to livestock animals such as cattle and sheep. In one embodiment, the process comprises applying the solution to livestock animals before they arrive in the Feed Lot, it being possible for this application to be the final one before the animals are slaughtered.

The compositions of the invention can also be formed in a collar such as those described in U.S. Pat. No. 5,885,607, which is incorporated herein by reference. Within the scope of the invention, matrices usually used to make collars may be used. In one embodiment of the collars which may be mentioned are matrices based on PVC (polyvinyl chloride), as described in U.S. Pat. Nos. 3,318,769; 3,852,416; 4,150,109 and 5,437,869, (all incorporated by reference) and other vinyl polymers.

The plasticizers may be chosen in particular from adipates, phthalates, phosphates and citrates. In another embodiment of the collar, one or more plasticizers are also added to the PVC, these plasticizers being chosen in particular from the following compounds: diethyl phthalate, dioctyl sebacate, dioctyl adipate, diisodecyl phthalate, acetyl tributyl citrate, diethyl hexyl phthalate, di-n-butyl phthalate, benzyl butyl phthalate, acetyl tributyl citrate, tricresyl phosphate, and 2-ethylhexyl diphenyl phosphate.

In another embodiment of the collar, a PVC matrix will be used in the presence of a primary remanent plasticizer and a secondary plasticizer, in particular according to EP 0 539 295 and EP 0 537 998.

Among the secondary plasticizers, mention may be made of the following products: acetyl triethyl citrate, triethyl citrate, triacetin, diethylene glycol monoethyl ether, triphenyl phosphate. A common stabilizer may also be added thereto.

For the purposes of the present invention, the term external device should be understood to refer to any device which can be attached externally to the animal in order to provide the same function as a collar.

In one embodiment of the invention, the active agent is present in the formulation at a concentration of about 0.05 to about 40% (w/v). In another embodiment of the invention, the active agent is present in the formulation as a concentration from about 1 to about 30% or about 1 to about 20% (w/v). In yet another embodiment of the invention, the active agent is present in the formulation as a concentration from about 5 to about 15% (w/v). In still another embodiment of the invention, the active agent is present in the formulation as a concentration about 10% (w/v), about 20% (w/v) or about 30% (w/v).

In one embodiment of the invention, the combination of 1-arylpyrazole and formamidine is present in the formulation at a concentration of about 2% to about 55% (w/v); about 10% to about 35% w/v; or about 18% to about 27% w/v. In another embodiment of the invention, the amount of 1-arylpyrazole is present in the formulation as a concentration of about 1% to about 25% (w/v); about 5% to about 15% (w/v); or about 8% to about 12% (w/v).

In another embodiment of the invention, the amount of formamidine in the formulations is about 1% to about 30 (w/v); about 5% to about 20% (w/v); or about 10% to about 15% (w/v).

The veterinarily acceptable carrier will generally comprise a diluent or vehicle and also a solvent (e.g. an organic solvent) for the active ingredient if the latter is not soluble, not stable or is degraded in the diluent.

Organic solvents that can be used in the invention include those described above, and include but are not limited to: acetyltributyl citrate, oleic acid, fatty acid esters such as the dimethyl ester, diisobutyl adipate, diisopropyl adipate (also known as CERAPHYL 230), ketones including acetone, methylisobutyl ketone (MIK) and methyl ethyl ketone and the like, acetonitrile, benzyl alcohol, methanol, ethyl alcohol, isopropanol, butanol, aromatic ethers such as anisole, butyl diglycol, amides including dimethylacetamide and dimethylformamide, dimethyl sulfoxide, propylene glycol monomethyl ether, propylene glycol monoethyl ether, dipropylene glycol n-butyl ether, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, triacetin, $C_1$-$C_{10}$ esters of carboxylic acids such as butyl or octyl acetate, benzyl acetate, aryl esters including benzyl benzoate, ethyl benzoate and the like, propylene carbonate, butylene carbonate, and diethyl phthalate, or a mixture of at least two of these solvents.

In one preferred embodiment of the invention, the pharmaceutically or veterinarily acceptable carrier of the formulation comprises $C_1$-$C_{10}$ alcohols or esters thereof (including acetates, such as ethyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

In another embodiment of the invention, the organic solvents may comprise diisopropyl adipate, dipropylene glycol monomethyl ether, propylene glycol monomethyl ether, 2-pyrrolidone including N-methylpyrrolidone, diethylene glycol monoethyl ether, triacetin, butyl acetate, octyl acetate, propylene carbonate, oleic acid, or a mixture of at least two of these solvents.

In one embodiment, preferred solvents include $C_1$-$C_{10}$ esters of carboxylic acids such as butyl or octyl acetate.

Particularly preferred solvents include diethyleneglycol monoethyl ether, triacetin, butyl acetate and octyl acetate, and mixtures thereof.

In some embodiments, the organic solvent will have a dielectric constant of between about 2 to about 35, between about 10 to about 35, or between about 20 to about 30. In other embodiments, the solvent will have a dielectric constant of between about 2 and about 20, or between about 2 and about 10. The content of this organic solvent in the overall composition will represent the complement to 100% of the composition. As discussed above, the organic solvents with dielectric constants within these ranges will typically be aprotic solvents, preferably polar aprotic solvents.

The carrier may comprise a mixture of solvents. In one embodiment, the formulations comprise an organic solvent and an organic co-solvent. In some embodiments, the formulations comprise a co-solvent having a boiling point of below about 300° C. or below about 250° C. In other embodiments, the co-solvent has a boiling point of below about 200° C., or below about 130° C. In other embodiments, the co-solvent has a dielectric constant of between about 2 to about 40 or between about 10 to about 40. In other embodiments, the co-solvent has a dielectric constant of between about 20 to about 30. In still another embodiment of the invention, the co-solvent has a dielectric constant of between about 2 to about 10.

When the formulations comprise an organic solvent and a co-solvent, in some embodiments the co-solvent may be present in the composition in a organic co-solvent/organic solvent weight/weight (W/W) ratio of between about 1/15 to about 1/2. In some embodiments, the co-solvent is volatile so as to act as a drying promoter, and is miscible with the organic solvent and may or may not be miscible with water.

The solvent will be used in proportion with the concentration of the active agent compound and its solubility in this solvent. It will be sought to have the lowest possible volume. The vehicle makes up the difference to 100%.

A vehicle or diluent can be dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent will be added. One embodiment of the emollient and/or spreading and/or film-forming agents are those agents selected from the group consisting of:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''Y^-$, in which the R radicals are optionally hydroxylated hydrocarbon radicals and $Y^-$ is an anion of a strong acid such as the halide, sulfate and sulphonate anions; cetyltrimethylammonium bromide is among the cationic surfactants which can be used, (d) amine salts of formula $N^+R'R''R'''$ in which the R radicals are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine, and (g) a mixture of at least two of these agents.

In one embodiment of the amount of emollient, the emollient is used in a proportion selected from the group consisting of from about 0.1 to about 10%, and about 0.25 to about 5%, by volume.

In another embodiment of the invention, the composition can be in ready-to-use solution form as is described, for example, in U.S. Pat. No. 6,395,765, which is incorporated herein by reference. In addition to the active agent compound, the ready-to-use solution can contain a crystallization inhibitor, an organic solvent and an organic co-solvent.

In some embodiments, the crystallization inhibitor can be present in a proportion of about 1 to about 30% (w/v). Typically, the crystallization inhibitor may be present in a proportion of about 1% to about 20% (w/v) or about 5% to about 15% (w/v). Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the 1-arylpyrazole in a solvent as described above with 10% (w/v) of the crystallization inhibitor will result in less 20, preferably less than 10 crystals when placed on a glass slide at 20° C. for 24 hours.

Crystallization inhibitors which are useful for the invention include but are not limited to:

(a) polyvinylpyrrolidone, polyvinyl alcohols, copolymers of vinyl acetate and of vinylpyrrolidone, 2-pyrrolidone including N-methylpyrrolidone, dimethylsufoxide, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and polymers derived from acrylic monomers, a solvent as described herein that inhibits the crystallization of the active agent, and others;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulphonate anions; cetyltrimethylammonium bromide is one of the cationic surfactants which can be used;

(d) amine salts of formula $N^+R'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents can be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants. In another embodiment of the surface active agents, the agent is a polyoxyethylenated esters of sorbitan. In yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned above.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

The formulation can also comprise an antioxidizing agent intended to inhibit oxidation in air, this agent being present in a proportion selected from a range consisting of about 0.005 to about 1% (w/v), and about 0.01 to about 0.05% (w/v).

In one embodiment of the antioxidizing agents, the agents are those conventional in the art and include, but are not limited to, butylated hydroxyanisole, butylated hydroxytoluene, ascorbic acid, sodium metabisulphite, propyl gallate, sodium thiosulfate or a mixture of not more than two of them.

The formulation adjuvants are well known to the practitioner in this art and may be obtained commercially or through known techniques. These concentrated compositions are generally prepared by simple mixing of the constituents as defined above. Advantageously, the starting point is to mix the active material in the main solvent and then the other ingredients or adjuvants are added.

The volume applied is not restricted as long as the amount of substance administered is shown to be safe and efficacious. Typically, the volume applied depends on the size and weight of the animal as well as the concentration of active, the extent of infestation by parasites and the type of administration. The volume applied is typically of the order of about 0.3 to about 1 ml, or about 0.3 ml to about 5 ml, or about 0.3 ml to about 10 ml. In other embodiments, the volume may be about 4 ml to about 7 ml. For larger animals, the volume may be higher including, but not limited to, up to 10 ml, up to 20 ml or up to 30 ml, or higher. In one embodiment of the volume, the volume is on the order of about 0.5 ml to about 1 ml for cats, and on the order of about 0.3 to about 3 ml or 4 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

Spot-on formulations are well known techniques for topically delivering an antiparasitic agent to a limited area of the host. For example, U.S. Pat. Nos. 5,045,536 6,426,333; 6,482,425; 6,962,713; and 6,998,131, all incorporated herein by reference, describe spot-on formulations. WO 01/957715, also incorporated herein by reference, describes a method for controlling ectoparasites in small rodents as well as interrupting or preventing the diseases caused by arthropods or small rodents, which comprise applying topical formulations, such as spot-on compositions, to the skin, or hair of the rodents.

For spot-on formulations, the carrier can be a liquid carrier vehicle as described, for example, in U.S. Pat. No. 6,426,333. Liquid carriers for spot-on formulations include the organic solvents and co-solvents described above, among other solvents known in the art.

The liquid carrier vehicle can optionally contain a crystallization inhibitor such as the crystallization inhibitors described above, or mixtures thereof.

Spot-on formulations, described for example in U.S. Pat. No. 7,262,214 (incorporated herein by reference), may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ecto-parasiticidal and endoparasiticidal agents.

Veterinary pharmaceutical agents that may be included in the compositions of the invention are well-known in the art (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, chlorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, other arylpyrazole compounds such as phenylpyrazoles described above in the Background, are known in the art and are suitable for combination with the 1-aryl-5-alkyl pyrazole compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.).

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins, such as abamectin, dimadectin, doramectin, emamectin, eprinomectin, ivermectin, latidectin, lepimectin, selamectin, ML-1,694,554 and milbemycins, such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, Ga.).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag, or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference). Examples of IGRs suitable for use include but are not limited to methoprene, pyriproxyfen, hydroprene, cyromazine, fluazuron, lufenuron, novaluron, pyrethroids, formamidines such as amitraz, 1-(2,6-difluorobenzoyl)-3-(2-fluoro-4-(trifluoromethyl)phenylurea, and novaluron.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In some embodiments, the compositions of the invention may include one or more antinematodal agents including, but not limited to, active agents in the benzimidazoles, imidazothiazoles, tetrahydropyrimidines, organophosphates class of compounds. In some embodiments, benzimidazoles including, but not limited to, thiabendazole, cambendazole, parbendazole, oxibendazole, mebendazole, flubendazole, fenbandazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against artropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfuram, isobornyl thiocyanato acetate, methroprene, monosulfuram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

An insecticidal agent that can be combined with the compound of the invention to form a composition can be a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular infection of an insect.

In certain embodiments, an insecticidal agent that can be combined with the compositions of the invention is a semicarbazone, such as metaflumizone.

In another embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelminitic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in US 2008/0312272 to Soll et al., which is incorporated herein in its entirety, and thioamide derivatives of these compounds, as described in U.S. patent application Ser. No. 12/582,486, filed Oct. 20, 2009, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

In general, the additional active agent is included in a dose of between about 0.1 μg and about 1000 mg. More typically, the additional active agent may be included in a dose of about 10 μg to about 500 mg, about 1 mg to about 300 mg, about 10 mg to about 200 mg or about 10 mg to about 100 mg. In one embodiment of the invention, the additional active agent is included in a dose of between about 1 μg and about 10 mg. In other embodiments of the invention, the additional active agent may be included in a dose of about 5 µg/kg to about 50 mg/kg per weight of the animal. In other embodiments, the additional active agent may be present in a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

The proportions, by weight, of the combinations of N-aryl-pyrazole compound/formamidine compound and the additional active agent are for example between about 1/10,000 and about 10,000/1. More typically, the proportions are in a proportion by weight of about 1/100 to about 10,000/1, about 1/1 to about 10,00/1, or about 5/1 to about 10,000/1, or about preferably about 5/1 to about 1000/1. However, one of ordinary skill in the art would be able to select the appropriate ratio of N-aryl-pyrazole compound/formamidine compound and the additional active agent for the intended host and use thereof.

Optionally, a fragrance may be added to any of the compositions of the invention. Fragrances which are useful for the invention include but are not limited to:

(i) carboxylic acid esters such as octyl acetate, isoamyl acetate, isopropyl acetate and isobutyl acetate;

(ii) fragrant oils such as lavender oil.

The compositions of the invention are made by mixing the appropriate amount of N-aryl-pyrazole compound and formamidine compound, veterinarily acceptable solvent and optionally a crystallization inhibitor, film former, odor dissipation enhancer, etc., to form a composition of the invention. Various forms (e.g. tablets, pastes, pour-on, spot-on, collars, etc.) of the composition can be obtained by following the method of making these forms described above by the description of making these forms found in general formulation text known to those in the art, e.g. *Remington—The Science and Practice of Pharmacy* (21$^{st}$ *Edition*) (2005), *Goodman & Gilman's The Pharmacological Basis of Therapeutics* (11$^{th}$ *Edition*) (2005) and *Ansel's Pharmaceutical Dosage Forms and Drug Delivery Systems* (8$^{th}$ *Edition*), edited by Allen et al., Lippincott Williams & Wilkins, (2005).

The inventive formulations may contain other inert ingredients such as antioxidants, preservatives, or pH stabilizers. These compounds are well known in the formulation art. Antioxidant such as an alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, with about 0.05 to about 1.0% being especially preferred. Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tataric acid/tartrate, lactic acid/lactate, phosphoric acid/phosphate, glycine/glycimate, tris, glutamic acid/glutamates and sodium carbonate.

The compositions of the invention are administered in antiparasiticidally effective amounts which are determined by the route of administration, e.g. oral, parenteral, topical, etc. In one embodiment of the invention, the compositions of the invention are applied as a pour-on or spot-on formulation.

In each aspect of the invention, the compounds and compositions of the invention can be applied against a single pest or combinations thereof.

The compositions of the invention that contain 1-arylpyrazole compounds, optionally in combination with a formamidine compound, may be administered continuously, for treatment or prevention, by known methods. In this manner, an effective amount of the compounds is administered to the animal in need thereof. By "effective amount" is intended a sufficient amount of a composition of the invention to eradicate or reduce the number of parasites infesting the animal. Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In one treatment embodiment, the treatment is carried out so as to administer to the animal, on a single occasion, a dose containing between about 0.001 and about 100 mg/kg of a 1-arylpyrazole compound. In another treatment embodiment, the treatment is via a direct topical administration such as a pour-on, ready-to-use, spot-on, spray, etc. type formulation. Higher amounts may be provided for very prolonged release in or on the body of the animal. In another treatment embodiment, the amount of 1-arylpyrazole compound for birds and other animals which are small in size is greater than about 0.01 mg/kg, and in another embodiment for the treatment of small-sized birds and other animals, the amount of 1-aryl-5-alkyl pyrazole compound is between about 1 and about 100 mg/kg of weight of animal.

The solutions according to the invention may be applied using any means known per se, e.g. using an applicator gun or a metering flask.

For the pour-on form of the composition, the volume applied can be of the order of about 0.3 to about 100 mL. In other embodiments, volume applied of the pour-on formulations may be about 1 ml to about 100 ml or about 1 ml to about 50 ml. In still other embodiments, the volume may be about 5 ml to about 50 ml or about 10 ml to about 100 ml.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

In another embodiment, application of the two active agents, an N-aryl-pyrazole compound and a formamidine compound can be administered together from separate compartments of a dual-cavity container. In yet another embodiment, an N-aryl-pyrazole compound and a formamidine compound can be combined in the same solvent system.

The application of an N-aryl-pyrazole compound and a formamidine compound would be expected to have efficacy against a wide range of parasites including fleas, ticks and mites. It was surprising that the application of a 1-arylpyrazole compound and a formamidine compound, whether applied from the same solvent system or from different solvent systems, resulted in synergistic effects with respect to efficacy against fleas and ticks. It was also surprising that a 1-arylpyrazole compound and a formamidine compound could be combined, since it has been observed that formamidine compounds may degrade in the presence of 1-arylpyrazole compounds.

In one embodiment of the method of use, a composition comprising a 1-arylpyrazole compound and a formamidine compound has an efficacy against ticks of about 80.0% or higher for at least about 37 days. In another embodiment of this method of use, a composition comprising a 1-arylpyrazole compound and a formamidine compound has an efficacy against ticks of about 90.0% or higher for at least about 37 days. In yet another embodiment of the invention, a composition comprising a 1-arylpyrazole compound and a formamidine compound has an efficacy of about 95% or higher for about 37 days or longer, about 44 days or longer, about 51 days or longer or for about 58 days or longer. In still another embodiment of the invention, a composition comprising a 1-arylpyrazole compound and a formamidine compound has an efficacy of about 99% or higher for about 51 days or longer or for about 58 days or longer. In each of these embodiments of use against ticks, a further embodiment of the invention is where the 1-arylpyrazole compound is fipronil; the formamidine compound is amitraz. In another embodiment, the 1-arylpyrazole compound is a 5-alkyl substituted 1-arylpyrazole compound and the formamidine compound is amitraz.

In another embodiment of the method of use, a composition comprising a 1-arylpyrazole compound and a formamidine compound has an efficacy against fleas of about 98.5% or higher for about 37 days or longer. In another embodiment of this method of use, a composition comprising a 1-arylpyrazole compound and a formamidine compound has an efficacy against ticks of about 98.5% or higher for about 37 days or longer or about 44 days or longer. In still another embodiment of this method of use, a composition comprising a 1-arylpyrazole compound and a formamidine compound has an efficacy against ticks of about 95.0% or higher for about 51 days or longer. In yet another embodiment, a composition comprising a 1-arylpyrazole compound and a formamidine compound has an efficacy of about 99% or higher for about 58 days or longer. In each of these embodiments of use against ticks, a further embodiment of the invention is where the 1-arylpyrazole compound is fipronil; the formamidine compound is amitraz. In another embodiment, the 1-arylpyrazole compound is a 5-alkyl substituted 1-arylpyrazole compound and the formamidine compound is amitraz.

The synergistic and long-lasting effects of the compositions of the embodiments either applied from the same solvent system or applied from different solvent systems for each 1-arylpyrazole and for a formamidine make them suitable for once a month (30 days or a calendar month) or once very two months (60 days or two calendar months) application of the composition in its deliverable form.

The animals that can be treated with the compositions of the invention include but are not limited to birds and mammals (either wild or domesticated), e.g., livestock and companion animals such as cats, dogs, horses, chickens, sheep, goats, pigs, turkeys and cattle. In one embodiment of the invention, the mammal is a cat or a dog.

In one embodiment of the location of administration, a single formulation containing the active agent in a substantially liquid carrier and in a form which makes possible a single application, or an application repeated a small number of times, will be administered to the animal over a localized region of the animal, e.g. between the two shoulders. In one embodiment of the invention, the localized region has a surface area of about 10 cm$^2$ or larger. In another embodiment of the invention, the localized region has a surface are of between about 5 and about 10 cm$^2$ area.

EXAMPLES

The invention is further described by the following non-limiting examples which further illustrate the invention, and are not intended, nor should they be interpreted to, limit the scope of the invention.

Example 1

Stability of 1-Arylpyrazole Formulations

Compound 1 (3-cyano-1-(2-chloro-6-fluoro-4-trifluoromethylphenyl)-4-dichlorofluoromethylsulfinyl-5-methyl-1H-pyrazole) was dissolved in a solvent or a combination of two or more solvents at 10% w/w. The formulations thus prepared were analyzed, using HPLC, for the content of compound 1 as the initial timepoint reading. Then all formulations were placed at 50° C., and the content of compound 1 in each of them was analyzed at the timepoints of two, four, six and, in some cases, 10 weeks. Compound 1 showed good stability in the solvents or combinations of solvents in Table 1 below. Thus formulations of Compound 1 in the solvents/carriers identified below are shown to be sufficiently stable.

TABLE 1

Stability of Formulations of comprising Compound 1
Stability Evaluation of Formulations
(Accelerated @ 50° C.)

| | | Compound 1 (%, w/w) | | | | |
|---|---|---|---|---|---|---|
| Form. # | Carrier Description | Initial | 2 wks | 4 wks | 6 wks | 10 wks |
| A | N-methylpyrrolidone | 8.80 | 8.78 | 8.72 | 9.19 | 8.80 |
| B | butyl acetate/octyl acetate | 10.41 | 10.51 | 10.42 | 10.32 | 10.41 |
| C | N-methylpyrrolidone/oleic acid | 8.70 | 8.95 | 8.83 | 9.26 | 9.25 |
| D | diethylene glycol monoethyl ether/ N-methylpyrrolidone | 9.10 | 9.10 | 8.93 | 8.99 | 9.20 |
| E | dipropylene glycol methyl ether/butyl acetate | 9.65 | 9.60 | 9.62 | 9.58 | 9.62 |
| F | diisopropyl adipate | 9.36 | 9.55 | 9.44 | 9.63 | 9.71 |
| G | butyl acetate/octyl acetate/ oleic acid | 10.54 | 10.58 | 10.41 | 10.32 | 10.32 |
| H | propylene carbonate | 8.20 | 8.30 | 8.50 | 8.36 | |
| I | diethylene glycol monoethyl ether | 9.88 | 9.95 | 10.06 | 9.95 | |
| J | dipropylene glycol methyl ether | 10.45 | 10.57 | 10.54 | 10.81 | |
| K | triacetin | 8.49 | 8.68 | 8.93 | 8.90 | |

Example 2

Flea and Tick Efficacy of 1-Arylpyrazole Formulations in Dogs: Study A

An initial clinical study was conducted to test the efficacy of Compound 1 (3-cyano-1-(2-chloro-6-fluoro-4-trifluoromethylphenyl)-4-dichlorofluoromethylsulfinyl-5-methyl-1H-pyrazole) against ticks and fleas in various test formulations. Five test groups and an untreated control were evaluated. Each test group included six dogs. Compound was dissolved in a solvent or a combination of two or more solvents at 10% w/w. Test articles were formulated as topical spot-on solutions containing compound 1, 10% w/v in a solvent or a combination of solvents as described above. Dogs were infested with approximately 50 ticks (*Rhipicephalus sanguineus*) on days −1, 7, 14, 21, 28, 35 and 42. Dogs were also infested with approximately 100 fleas (*Ctenocephalides felis*) on days −1, 8, 15, 22, 29, 36, and 43. Treatment was applied by parting the hair and applying the formulation directly onto the skin on one spot at the midline of the neck, between the base of the skull and the shoulder blades. The dose rate of each of the topical solutions was 0.1 ml/kg (10 mg/kg) body weight. The efficacy of compound 1 in various formulations is shown Table 2 below. Duration of flea and tick efficacy is shown in Tables 3 and 4 below. As can be seen from the tables below, formulations comprising Compound 1 in triacetin formulations provide improved efficacy against fleas and ticks in this study.

TABLE 2

Flea and Tick Efficacy of Compound 1 in Various Formulations.

| Trt. Group | Drug | Dose Vol./mg/kg | Solvent(s) | Efficacy against fleas on day 30 (%) | Efficacy against fleas on day 44 (%) | Efficacy against ticks on day 44 (%) |
|---|---|---|---|---|---|---|
| 1 | Untreated | NA | Commercial FRONTLINE vehicle | | | |
| 2 | Compound 1 | 0.1 ml/kg (10 mg/kg) | Butyl acetate/octyl acetate | 94.5 | 46.9 | −8.6 |
| 3 | Compound 1 | 0.1 ml/kg (10 mg/kg) | Diethylene glycol monoethyl ether (transcutol)/N-methyl-2-pyrrolidone | 91.4 | 38.9 | −10.8 |
| 4 | Compound 1 | 0.1 ml/kg (10 mg/kg) | Dipropylene glycol monomethyl ether/butyl acetate | 83.2 | 31.1 | −29.9 |
| 5 | Compound 1 | 0.1 ml/kg (10 mg/kg) | Diisopropyl adipate | 92.9 | 40.3 | 0.3 |
| 6 | Compound 1 | 0.1 ml/kg (10 mg/kg) | Triacetin | 99.7 | 93.0 | 47.8 |

TABLE 3

Duration of Flea Efficacy of Compound 1 in Various Formulations.
(% efficacy against fleas measured 24 hours after each weekly infestation)

| | % Efficacy at Days after Treatment | | | | | | |
|---|---|---|---|---|---|---|---|
| Trt. Group | Day 2 | Day 9 | Day 16 | Day 23 | Day 30 | Day 37 | Day 44 |
| 1 (control) | 0 | 0 | 0 | 0 | 0 | 0 | 0 |
| 2 | 99.6 | 100 | 100 | 99.4 | 94.5 | 80.4 | 46.9 |
| 3 | 96.0 | 100 | 99.8 | 98.8 | 91.4 | 85.3 | 38.9 |
| 4 | 100 | 100 | 100 | 99.5 | 83.2 | 76.5 | 31.1 |
| 5 | 100 | 100 | 100 | 100 | 92.9 | 69.1 | 40.3 |
| 6 | 98.0 | 100 | 100 | 100 | 99.7 | 98.9 | 93.0 |

Treatment groups in Table 3 were treated with the drug, dosage and solvent formulations as indicated in Table 2.

TABLE 4

Duration of Tick Efficacy of Compound 1 in Various Formulations.
(% efficacy against ticks measured 24 hours after each weekly infestation)

| | % Efficacy at Days after Treatment | | | | | | |
|---|---|---|---|---|---|---|---|
| Treatment Group | Day 1 | Day 2 | Day 9 | Day 16 | Day 23 | Day 30 | Day 44 |
| 1 (control) | 0 | 0 | 0 | 0 | 0 | 0 | 0 |
| 2 | 48.6 | 67.6 | 88.1 | 88.7 | 41.1 | 64.0 | −8.6 |
| 3 | 59.0 | 60.8 | 78.1 | 81.4 | 52.2 | 45.9 | −10.8 |
| 4 | 71.5 | 72.0 | 71.2 | 90.5 | 38.4 | 71.7 | −29.9 |
| 5 | 71.5 | 86.0 | 90.4 | 83.2 | 20.4 | 78.2 | 0.3 |
| 6 | 80.7 | 79.2 | 83.1 | 91.7 | 89.1 | 72.3 | 47.8 |

Treatment groups in Table 4 were treated with the drug, dosage and solvent formulations as indicated in Table 2. Negative values indicate % increase in tick counts relative to control.

Example 3

Flea and Tick Efficacy of 1-Arylpyrazole Formulations in Dogs: Study B

A separate clinical efficacy study in dogs was designed with an untreated control group and 5 test groups treated with compound 1. Each group had six dogs. Test articles were formulated as topical spot-on solutions containing compound 1, 10-20% w/v in a solvent or a combination of solvents as described above. Dogs were infested with approximately 50 ticks (*Rhipicephalus sanguineus*) on days −1, 7, 14, 21, 28, 35 and 42. Dogs were also infested with approximately 100 fleas (*Ctenocephalides felis*) on days −1, 8, 15, 22, 29, 36, and 43. Treatment was applied by parting the hair and applying the formulation directly onto the skin on one spot at the midline of the neck, between the base of the skull and the shoulder blades. The dose rate of each of the topical solutions was 0.1 ml/kg (10 mg/kg) body weight except for treatment group 4, which received 0.2 ml/kg (20 mg/kg). The efficacy of compound 1 is shown in Table 5 below. Duration of flea and tick efficacy is shown in Tables 6 and 7 below. As can be seen from the table, transcutol renders compound 1 superior efficacy. It should be noted that Study A and Study B were conducted at different times and locations, and the results of each clinical study may differ from the other based on various environmental factors. Thus, the results of one clinical study should not be compared with those of another due to these factors.

TABLE 5

Flea and Tick Efficacy of Compound 1 in Various Formulations.

| Trt. Group | Drug | Dose | Solvent(s) | Efficacy against fleas on day 58 (%) | Efficacy against ticks on day 58 (%) |
|---|---|---|---|---|---|
| 1 | Untreated | NA | Commercial FRONTLINE vehicle | | |
| 2 | Compound 1 | 0.1 ml/kg (10 mg/kg) | Triacetin | 99.6 | 74.6 |
| 3 | Compound 1 | 0.2 ml/kg (20 mg/kg) | Triacetin | 99.0 | 97.6 |
| 4 | Compound 1 | 0.1 ml/kg (10 mg/kg) | Diisopropyl adipate | 96.7 | 89.5 |
| 5 | Compound 1 | 0.1 ml/kg (10 mg/kg) | Diethylene glycol monoethyl ether (transcutol) | 100 | 94.1 |
| 6 | Compound 1 | 0.1 ml/kg (10 mg/kg) | Triacetin/diisopropyl adipate | 98.8 | 88.1 |

TABLE 6

Duration of Flea Efficacy of Compound 1 in Various Formulations.
(% efficacy against fleas measured 24 hours after each weekly infestation)

| Trt Group | % Efficacy at Days after Treatment | | | | | | | | |
|---|---|---|---|---|---|---|---|---|---|
| | Day 2 | Day 9 | Day 16 | Day 23 | Day 30 | Day 37 | Day 44 | Day 51 | Day 58 |
| 1 (control) | | | | | | | | | |
| 2 | 100 | 100 | 100 | 99.8 | 99.7 | 99.8 | 100 | 99.8 | 99.6 |
| 3 | 100 | 100 | 100 | 99.8 | 100 | 100 | 100 | 99.7 | 99.0 |
| 4 | 100 | 100 | 100 | 100 | 100 | 98.9 | 99.6 | 98.5 | 96.7 |
| 5 | 100 | 100 | 100 | 99.8 | 100 | 100 | 100 | 100 | 100 |
| 6 | 100 | 100 | 100 | 99.8 | 100 | 100 | 100 | 100 | 98.8 |

Treatment groups in Table 6 were treated with the drug, dosage and solvent formulations as indicated in Table 5.

TABLE 7

Duration of Tick Efficacy of Compound 1 in Various Formulations.
(% efficacy against ticks measured 24 hours after each weekly infestation)

| Trt Group | % Efficacy at Days after Treatment | | | | | | | | |
|---|---|---|---|---|---|---|---|---|---|
| | Day 1 | Day 2 | Day 9 | Day 16 | Day 23 | Day 30 | Day 44 | Day 51 | Day 58 |
| 1 (control) | | | | | | | | | |
| 2 | 94.8 | 99.6 | 100 | 100 | 100 | 98.8 | 94.5 | 90.8 | 74.6 |
| 3 | 93.9 | 98.9 | 100 | 100 | 100 | 100 | 99.4 | 99.3 | 97.6 |
| 4 | 95.6 | 98.9 | 100 | 100 | 99.1 | 99.1 | 93.4 | 87.9 | 89.5 |
| 5 | 87.4 | 98.5 | 100 | 100 | 100 | 98.8 | 98.5 | 98.9 | 94.1 |
| 6 | 94.8 | 99.6 | 100 | 100 | 100 | 98.8 | 96.6 | 91.6 | 88.1 |

Treatment groups in Table 7 were treated with the drug, dosage and solvent formulations as indicated in Table 5.

Example 4

Flea and Tick Efficacy of 1-Arylpyrazole Formulations in Dogs: Study C

The effectiveness of Compound 1 alone, fipronil alone, Compound 1 in combination with amitraz, or fipronil in combination with amitraz, when administered once as topical solutions to dogs against induced infestations of *Rhipicephalus sanguineus* and *Ctenocephalides felis* were determined in a third clinical study. Thirty-six beagles (18 males and 18 females) were selected for the study. Six replicates of 6 animals each were formed. Treatment Group 1 dogs were treated with a placebo. Treatment Groups 2, 3, 4, 5 and 6 received their respective treatments as a topical spot-on application once on Day 0. Each formulation included diethyleneglycol monoethyl ether (transcutol) as carrier. The Treatment Groups were: Treatment Group 2: fipronil at 0.1 mL/kg body weight (10 mg/kg); Treatment Group 3: Compound 1 at 0.1 mL/kg (10 mg/kg) body weight; Treatment Group 4: Compound 1 at 0.2 mL/kg (20 mg/kg) body weight; Treatment Group 5: Compound 1 at 0.1 mL/kg (10 mg/kg) body weight plus amitraz at 0.04 mL/kg (8 mg/kg) body weight; Treatment Group 6: fipronil at 0.1 mL/kg (10 mg/kg) body weight plus amitraz at 0.04 mL/kg (8 mg/kg) body weight. Treatment was applied by parting the hair and applying the formulation(s) directly onto the skin on one spot at the midline of the neck, except for Groups 4, 5 and 6 which were applied in approximately equal volumes on two spots, one spot between the base of the skull and the shoulder blades and the other at the front of the shoulder blades.

All dogs were infested with approximately 50 *Rhipicephalus sanguineus* ticks on Days −1, 7, 14, 21, 28, 35, 42, 49 and 56. Dogs were also infested with approximately 100 *Ctenocephalides felis* fleas on Days −1, 8, 15, 22, 29, 36, 43, 50 and 57. Ectoparasites were removed and counted on Day 2, approximately 48 hours after treatment and on Days 9, 16, 23, 30, 37, 44, 51 and 58 approximately 24 hours after flea infestation and 48 hours after tick infestation. Tables 8 and 9 below show the % efficacy of formulations comprising fipronil at 0.1 ml/kg of body weight, Compound 1 at 10 ml/kg and 20 ml/kg, and fipronil and Compound 1 both at 10 ml/kg in combination with amitraz at 0.04 ml/kg of body weight compared to control group without active compounds. The percent reduction in flea counts of the treated groups with respect to the Control group over the study is shown in Figure 14.

TABLE 8

Duration of Flea Efficacy of Compound 1 and Fipronil Alone and With Amitraz.(% efficacy against fleas measured 24 hours after each weekly infestation)

| Trt Group | DRUG | % Efficacy at Days after Treatment | | | | | | | | |
|---|---|---|---|---|---|---|---|---|---|---|
| | | Day 2 | Day 9 | Day 16 | Day 23 | Day 30 | Day 37 | Day 44 | Day 51 | Day 58 |
| 1 (control) | | | | | | | | | | |
| 2 | Fipronil 10 mg/kg | 100 | 100 | 100 | 100 | 100 | 100 | 99.8 | 100 | 99.1 |
| 3 | Cmpd 1 10 mg/kg | 100 | 100 | 100 | 100 | 99.8 | 99.4 | 98.6 | 98.5 | 94.6 |
| 4 | Cmpd 1 20 mg/kg | 100 | 100 | 100 | 100 | 100 | 100 | 100 | 99.8 | 100 |
| 5 | Cmpd 1, 10 mg/kg + amitraz 8 mg/kg | 100 | 100 | 100 | 100 | 100 | 100 | 100 | 100 | 100 |
| 6 | Fipronil 10 mg/kg + amitraz 8 mg/kg | 100 | 100 | 100 | 100 | 100 | 100 | 100 | 100 | 100 |

TABLE 9

Duration of Tick Efficacy of Compound 1 and Fipronil Alone and With Amitraz.(% efficacy against fleas measured 48 hours after each weekly infestation)

| Trt Group | Day 1 | Day 2 | Day 8 | Day 9 | Day 15 | Day 16 | Day 23 | Day 30 | Day 37 | Day 44 | Day 51 | Day 58 |
|---|---|---|---|---|---|---|---|---|---|---|---|---|
| 1 (control) | | | | | | | | | | | | |
| 2 | 88.6 | 90.9 | 99.4 | 100 | 100 | 100 | 98.8 | 100 | 99 | 98.2 | 92.8 | 82.7 |
| 3 | 88.1 | 96.8 | 93.5 | 97.7 | 98.5 | 100 | 98.4 | 99 | 94.3 | 92.4 | 84.7 | 83.1 |
| 4 | 98.6 | 98.9 | 98.6 | 100 | 99.3 | 100 | 100 | 99.5 | 98.6 | 92.3 | 86.5 | 87.4 |
| 5 | 90 | 100 | 100 | 100 | 100 | 100 | 99.4 | 100 | 100 | 99.6 | 97 | 72.9 |
| 6 | 87.9 | 98.9 | 100 | 100 | 100 | 100 | 100 | 100 | 100 | 100 | 100 | 99.5 |

Treatment Group 2: fipronil 10 mg/kg;
Group 3: Cmpd 1 10 mg/kg;
Group 4: Cmpd 1 20 mg/kg;
Group 5: Cmpd 1 (10 mg/kg) + amitraz (8 mg/kg);
Group 6: fipronil (10 mg/kg) + amitraz (8 mg/kg)

Example 5

Flea Efficacy of 1-Arylpyrazole Formulations in Cats: Study D

A fourth clinical study was conducted to determine the efficacy of topically administered Compound 1 and fipronil against induced infections of *Ctenocephalides felis* in cats. Twenty four cats (17 males, 7 females) were included in the study. Six replicates of four cats each were formed based on decreasing Day −5 flea counts. Within replicates, cats were randomly allocated to Treatment Groups 1, 2, 3 or 4, respectively, by using a die: Group 1—untreated (vehicle control); Group 2—Compound 1 (10 mg/kg); Group 3—Compound 1 (20 mg/kg); Group 4—fipronil (10 mg/kg). Treatment was performed by topical administration of the formulations in the midline of the neck, between the base of the skull and the shoulder blades in a single spot after parting the hair. Animals were observed hourly for approximately four hours following treatment.

The cats were infested with approximately 100 *Ct. felis* fleas each during acclimation on Day −6 for allocation purposes, and on Days −1, 14, 21, 28, 35 and 42 for treatment efficacy evaluation purposes. The fleas were removed by combing each cat approximately 24 hours following each infestation except for the Day −1 infestation which was followed by flea removal and count on Day 1 (~48 hours following infestation). Table 10 below shows the % efficacy of each treatment group compared to the control group.

TABLE 10

Duration of Flea Efficacy of Compound 1 and Fipronil (% efficacy against fleas measured 24 hours after each weekly infestation)

| Treatment Group | % Efficacy at Days after Treatment | | | | | |
|---|---|---|---|---|---|---|
| | Day 1 | Day 15 | Day 22 | Day 29 | Day 36 | Day 43 |
| 1 (control) | | | | | | |
| 2 | 99.84 | 99.81 | 100 | 100 | 99.43 | 97.28 |
| 3 | 100 | 100 | 100 | 100 | 100 | 100 |
| 4 | 97.96 | 100 | 100 | 95.59 | 99.24 | 97.81 |

Treatment Group 2: Cmpd 1 10 mg/kg; Group 3: Cmpd 1 20 mg/kg; Group 5: fipronil (10 mg/kg)

Flea counts on Days 1, 15, 22, 29, 36 and 43 indicated >97% efficacy against *C. felis* in Group 2 and 4 animals. Flea counts of Group 3 animals indicated 100% efficacy against *C. felis* at all time points. The study demonstrates the excellent efficacy of Compound 1 both at 10 mg/kg and 20 mg/kg against fleas in cats. Figure

Example 6

Stable Formulations Comprising Amitraz

Several formulations comprising amitraz in different carriers/solvents were prepared according the procedures below to evaluate the stability of amitraz in the formulations and to determine whether amitraz was sufficiently soluble in the formulations.

Formulation L

Anisole was added in the amount of about 50% of the volume to be prepared into a flask with a stopper. Amitraz was added to the anisole solution with stirring and the stirring was continued until the amitraz was fully dissolved. The volume was adjusted to 100% with anisole.

| Ingredients | Function | % |
|---|---|---|
| Amitraz | Active | 28.0 w/v |
| Anisole | Solvent | q.s. 100 |

Formulation M

Butyl acetate was added in the amount of about 50% of the volume to be prepared into a flask with a stopper. Amitraz was added to the butyl acetate solution with stirring and the stirring was continued until the amitraz was fully dissolved. The volume was adjusted to 100% with butyl acetate.

| Ingredients | Function | % |
|---|---|---|
| Amitraz | Active | 25.0 w/v |
| Butyl acetate | Solvent | q.s. 100 |

Formulation N

Ethyl benzoate was added in the amount of about 50% of the volume to be prepared into a flask with a stopper. Amitraz was added to the ethyl benzoate solution with stirring and the stirring was continued until the amitraz was fully dissolved. The volume was adjusted to 100% with ethyl benzoate.

| Ingredients | Function | % |
|---|---|---|
| Amitraz | Active | 28.0 w/v |
| Ethyl benzoate | Solvent | q.s. 100 |

Formulation O

Benzyl benzoate was added in the amount of about 50% of the volume to be prepared into a flask with a stopper. Amitraz was added to the benzyl benzoate solution with stirring and the stirring was continued until the amitraz is fully dissolved. The volume was adjusted to 100% with benzyl benzoate.

| Ingredients | Function | % |
|---|---|---|
| Amitraz | Active | 25.0 w/v |
| Benzyl benzoate | Solvent | q.s. 100 |

Formulation P

Butyl acetate was added in the amount of about 50% of the volume to be prepared into a flask with a stopper. Anisole was added to the butyl acetate solution and mixed. Amitraz was then added to the anisole/butyl acetate solution with stirring and the stirring was continued until the amitraz is fully dissolved. The volume was adjusted to 100% with butyl acetate.

| Ingredients | Function | % |
|---|---|---|
| Amitraz | Active | 25.0 w/v |
| Anisole | Solvent | 10.0 v/v |
| Butyl acetate | Solvent | q.s. 100 |

Formulation Q

Butyl acetate was added in the amount of about 50% of the volume to be prepared into a flask with a stopper. Methyl isobutyl ketone was added to the butyl acetate solution and mixed. Amitraz was then added to the methyl isobutyl ketone/butyl acetate solution with stirring and the stirring was continued until the amitraz was fully dissolved. The volume was adjusted to 100% with butyl acetate.

| Ingredients | Function | % |
|---|---|---|
| Amitraz | Active | 25.0 w/v |
| Methyl isobutyl ketone | Solvent | 10.0 v/v |
| Butyl acetate | Solvent | q.s. 100 |

Formulation R

Butyl acetate was added in the amount of about 50% of the volume to be prepared into a flask with a stopper. Benzyl benzoate was added to the butyl acetate solution and mixed. Amitraz was then added to the benzyl benzoate/butyl acetate solution with stirring and the stirring was continued until the amitraz was fully dissolved. The volume was adjusted to 100% with butyl acetate.

| Ingredients | Function | % |
|---|---|---|
| Amitraz | Active | 25.0 w/v |
| Benzyl benzoate | Solvent | 5.0 v/v |
| Butyl acetate | Solvent | q.s. 100 |

Formulation S

Butyl acetate was added in the amount of about 50% of the volume to be prepared into a flask with a stopper. Ethyl benzoate was added to the butyl acetate solution and mixed. Amitraz was then added to the ethyl benzoate/butyl acetate solution with stirring and the stirring was continued until the amitraz was fully dissolved. The volume was adjusted to 100% with butyl acetate.

| Ingredients | Function | % |
|---|---|---|
| Amitraz | Active | 25.0 w/v |
| Ethyl benzoate | Solvent | 5.0 v/v |
| Butyl acetate | Solvent | q.s. 100 |

Formulation T

Butyl acetate was added in the amount of about 50% of the volume to be prepared into a flask with a stopper. Benzyl acetate was added to the butyl acetate solution and mixed. Amitraz was then added to the benzyl acetate/butyl acetate solution with stirring and the stirring was continued until the amitraz was fully dissolved. The volume was adjusted to 100% with butyl acetate.

| Ingredients | Function | % |
|---|---|---|
| Amitraz | Active | 20.0 w/v |
| Benzyl acetate | Solvent | 10.0 v/v |
| Butyl acetate | Solvent | q.s. 100 |

Example 7

Stability of Amitraz in Solution

Formulation comprising amitraz in anisole (formulation L), butyl acetate (formulation M), methyl isobutyl ketone and ethyl benzoate were evaluated for stability by HPLC, similarly to the stability study for formulations comprising compound 1. Thus the formulations were tested for initial concentration of amitraz % (w/v) and aged at 50° C. for three months. The concentration of amitraz in each formulation was determined at 1 month, 2 months and 3 months to determine the stability of amitraz in each formulation. As shown in Table 11 below, formulations of amitraz in anisole, butyl acetate and methyl isobutyl ketone do not show degradation at these conditions.

TABLE 11

Stability of Amitraz Formulations

| Formulation Solvent: | % Amitraz (w/v) | % theoretical | | |
|---|---|---|---|---|
| | | 1 month | 2 months | 3 months |
| Anisole (formulation L) | 28 | 101 | 101 | 97 |
| Butyl acetate (formulation M) | 25 | 104 | 102 | 105 |
| Methyl isobutyl ketone (MIK) | 28 | 93 | 98 | 100 |
| Ethyl benzoate (formulation N) | 28 | 98 | 96 | 94 |

Example 8

Solubility of Amitraz in Solution

The solubility of amitraz in various solvents is shown in Table 12 below. Solutions of amitraz in certain solvents at high concentration result in the appearance of crystals over time. For example, Formulation P above resulted in a small amounts of crystal formation after 1 week of storage [at ambient temperature. However, when the concentration of amitraz in this formulation was decreased to 20% w/v, no crystal formation was observed after 1 week of storage. Formulation Q showed no crystallization after 1 week of storage. The solubility of amitraz in butyl acetate is lower then in anisole, MIK and ethyl benzoate. It has been observed during clinical studies that formulation of amitraz (25%) in butyl acetate produced white crystals on the coat of animals, therefore small amounts of other solvent, with higher solubility of amitraz, were added. Additionally, when amitraz (25%) in butyl acetate formulations were stored at 50° C. in a chamber, they evaporated slightly. Upon cooling to room temperature, these solutions precipitated crystals. Again, lowering concentration to 20% and addition of co-solvents with higher solubility of amitraz avoided crystallization of amitraz. Unexpectedly, this addition of co-solvents caused the effects described below in Example 9.

TABLE 12

Solubility of Amitraz

| Solvent | Solubility of amitraz (at room temperature, %) | Dielectric Constant of solvent |
|---|---|---|
| Acetone | 37.87 | 20.7 |
| Anisole (methoxybenzene) | 45.54 | 4.33 |
| Benzyl benzoate | 33.30 | 4.8 |
| Benzyl acetate | 21.85 | 5.0 |

TABLE 12-continued

Solubility of Amitraz

| Solvent | Solubility of amitraz (at room temperature, %) | Dielectric Constant of solvent |
|---|---|---|
| Butyl acetate | 27.10 | 5.0 |
| Ethyl benzoate | 39.43 | 6.02 |
| Methyl isobutyl ketone | 36.72 | 13.1 |

Example 9

Effect of Solvent on Odor and Odor Dissipation

Amitraz solutions in a single solvent exhibited an unpleasant smell that lasted from about 30 minutes to about 90 minutes when applied to filter paper. However, when the solutions of Formulations P and Q were applied to filter paper, the smell disappeared after only about 10 to about 15 minutes.

Example 10

Efficacy of Combination of Fipronil with Amitraz Against Ticks on Dogs

A fipronil formulation (commercial product) was prepared and stored separately from amitraz. Amitraz was formulated with the same carrier. Both parts, fipronil and amitraz in solvent(s) were stored separately and applied simultaneously. Amounts applied were calculated to keep dose at 10% (w/v) each in final formulation and 10 mg/kg BW of actives in amount applied.

Table 13 below shows the percent efficacy after topical application of the formulations comprising amitraz alone, fipronil alone or amitraz and fipronil to dogs. In brief, treatment was applied by parting the hair on the midline of the neck, between the base of the skull and the shoulder blades, and applying the formulation directly onto the skin.

TABLE 13

Efficacy of Compositions Comprising Amitraz and Fipronil Against Ticks

| | Days after treatment | | | | | |
|---|---|---|---|---|---|---|
| | 2 | 16 | 23 | 30 | 37 | 44 |
| Fipronil + Amitraz | 98.8 | 98.4 | 100 | 97.7 | 94.2 | 79.5 |
| Comparative Fipronil | 90.9 | 100 | 99.3 | 53.9 | 43.9 | 37.9 |
| Comparative Amitraz | 95.1 | 96.9 | 95.0 | 64.9 | 56.2 | 28.3 |

As can be seen from the data above, the combination of fipronil and amitraz shows markedly better efficacy against ticks than the use of fipronil or amitraz alone. Fipronil and amitraz were found to be compatible with each other when administered simultaneously to the animals.

Example 11

Efficacy of Combination of Fipronil and Amitraz Against Fleas on Dogs

The amitraz and fipronil composition described in Example 10 were used in this study. Table 14 below shows the percent efficacy after topical application of the formulation to dogs. Treatment was applied by parting the hair on the midline of the neck, between the base of the skull and the shoulder blades, and applying the formulation directly onto the skin.

TABLE 14

Efficacy of Compositions Comprising Fipronil and Amitraz Against Fleas

| | Days after treatment | | | | | |
|---|---|---|---|---|---|---|
| | 2 | 16 | 23 | 30 | 37 | 44 | 51 |
| Fipronil + Amitraz | 99.6 | 100 | 100 | 100 | 100 | 98.2 | 95.7 |
| Comparative Fipronil | 100 | 100 | 100 | 94.4 | 63.4 | 55.9 | 74.7 |
| Comparative Amitraz | 14.3 | 12.4 | 16.3 | 20.2 | 32.5 | 25.9 | — |

As can be seen from the data in Table 14 above, the combination of fipronil and amitraz shows markedly better efficacy against fleas than the use of fipronil or amitraz alone and is also surprising from the standpoint that fipronil and amitraz were found to be compatible with each other.

Example 12

Synergistic Effect of Fipronil with Amitraz in Tick Contact Assay

Fipronil was dissolved in acetone containing 0.019% of a mixture of Triton 152 and Triton 172 (1:3, v/v) and 0.4% DMSO to achieve the desired concentration. Dosages were serially diluted using this same formulation. For treatments containing amitraz, amitraz was added to the above solution to achieve the desired concentration. 0.5 ml of the solution was used to treat 20 ml scintillation vials containing a 0.125" hole in the cap. This was achieved by rolling the uncapped vials until the acetone had evaporated thus leaving the walls of the vial coated with the experimental compound(s). Filter papers treated with this same solution were placed in the cap and bottom of the treated vial. Vials were capped and held over night at 24° C. and 95% RH after which 10 adult *Rhipicephalus sanguineus* ticks were placed into each vial. The vials were held under the same conditions mentioned above for the duration of the test. The number of living and dead ticks in each vial was determined at 6, 24 and 48 hrs. Tables 15 and 16 below show the efficacy of fipronil alone and fipronil in combination with amitraz at various concentrations. Table 17 presents synergistic ratios of amitraz and fipronil and shows the calculated EC50 and EC90 values at 6 hours, 24 hours and 48 hours for fipronil alone and the combination of fipronil and amitraz.

TABLE 15

Tick Efficacy of fipronil in DMSO contact Test

| | | 6 hour % Mortality | | | 24 hour % Mortality | | | 48 hour % Mortality | | |
|---|---|---|---|---|---|---|---|---|---|---|
| Cmpd. | Rate ppm | Rep 1 | Rep 2 | Avg. % Mortality | Rep 1 | Rep 2 | Avg. % Mortality | Rep 1 | Rep 2 | Avg. % Mortality |
| fipronil | 25 | 40 | 60 | 50 | 80 | 90 | 85 | 100 | 100 | 100 |
| | 6.25 | 0 | 20 | 10 | 90 | 50 | 70 | 100 | 100 | 100 |
| | 1.6 | 0 | 0 | 0 | 20 | 40 | 30 | 50 | 60 | 55 |
| | 0.4 | 0 | 0 | 0 | 0 | 0 | 0 | 20 | 20 | 20 |
| | 0.1 | 0 | 0 | 0 | 0 | 0 | 0 | 0 | 0 | 0 |
| | 0.025 | 0 | 0 | 0 | 0 | 0 | 0 | 0 | 0 | 0 |
| | 0.006 | 0 | 0 | 0 | 0 | 0 | 0 | 0 | 0 | 0 |
| | 0.0016 | 0 | 0 | 0 | 0 | 0 | 0 | 0 | 0 | 0 |
| Solvent control | | 0 | 0 | 0 | 0 | 0 | 0 | 0 | 0 | 0 |
| Untreated Control | | 0 | 0 | 0 | 0 | 0 | 0 | 0 | 0 | 0 |

Rate is the ppm of the solution used to treat the vials.

TABLE 16

Synergistic Tick Efficacy of Fipronil with Amitraz in DMSO Contact Test

| | | 6 hour % Mortality | | | 24 hour % Mortality | | | 48 hour % Mortality | | |
|---|---|---|---|---|---|---|---|---|---|---|
| Cmpd | Rate ppm | Rep 1 | Rep 2 | Avg. % Mortality | Rep 1 | Rep 2 | Avg. % Mortality | Rep 1 | Rep 2 | Avg. % Mortality |
| fipronil + Amitraz (12.5 ppm) | 25 | 100 | 100 | 100 | 100 | 100 | 100 | 100 | 100 | 100 |
| | 6.25 | 100 | 100 | 100 | 100 | 100 | 100 | 100 | 100 | 100 |
| | 1.6 | 30 | 60 | 45 | 100 | 100 | 100 | 100 | 100 | 100 |
| | 0.4 | 0 | 10 | 5 | 100 | 100 | 100 | 100 | 100 | 100 |
| | 0.1 | 0 | 0 | 0 | 90 | 80 | 85 | 90 | 80 | 85 |
| | 0.025 | 0 | 0 | 0 | 60 | 40 | 50 | 60 | 40 | 50 |
| | 0.006 | 0 | 0 | 0 | 20 | 30 | 25 | 20 | 30 | 25 |
| | 0.0016 | 0 | 0 | 0 | 0 | 0 | 0 | 0 | 0 | 0 |
| Amitraz | 25 | 0 | 0 | 0 | 0 | 0 | 0 | 10 | 10 | 10 |
| | 12.5 | 0 | 0 | 0 | 0 | 0 | 0 | 0 | 0 | 0 |
| | 6.25 | 0 | 0 | 0 | 0 | 0 | 0 | 0 | 0 | 0 |

TABLE 16-continued

Synergistic Tick Efficacy of Fipronil with Amitraz in DMSO Contact Test

| Cmpd | Rate ppm | 6 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| Solvent control | | 0 | 0 | 0 | 0 | 0 | 0 | 0 | 0 | 0 |
| Untreated Control | | 0 | 0 | 0 | 0 | 0 | 0 | 0 | 0 | 0 |

Rate is the ppm of the solution used to treat the vials.

TABLE 17

EC50, EC90 and Synergistic Ratios of Tick Efficacy of Fipronil with Amitraz in DMSO Contact Test

| Compound | 6 hour Eval | | 24 hour Eval | | 48 hour Eval | |
|---|---|---|---|---|---|---|
| | EC50 | EC90 | EC50 | EC90 | EC50 | EC90 |
| fipronil | 25 | >25 | 3.45 | >25 | 1.24 | 5.17 |
| fipronil + Amitraz (12.5 ppm) | 1.7 | 3.7 | 0.022 | 0.16 | 0.022 | 0.16 |
| Synergistic Ratio for fipronil | 14.7 | >6.76 | 156.8 | >156 | 56.4 | 32.3 |

Synergistic ratio is EC50 or EC90 alone divided by EC50 or EC90 with Amitraz.

Example 13

Synergistic Effect of Fipronil with Amitraz at Different Dosages in Tick Contact Assay Another study shown in Tables 18 and 19 below further demonstrate the synergistic efficacy of fipronil and amitraz. The assay protocol was similar to the protocol of Example 12, with the following exceptions: 1) The vials were visually evaluated at 4, 24 and 48 hours post infestation for living/dead ticks and percent mortality was determined, and 2) the amitraz was added at dosages of 12.5 ppm, 6.25 ppm, and 3.13 ppm.

TABLE 18

Tick Efficacy of fipronil in DMSO contact Test

| Compound | Rate ppm | 4 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| fipronil | 25 | 80 | 90 | 85 | 100 | 100 | 100 | 100 | 100 | 100 |
| | 6.25 | 10 | 20 | 15 | 100 | 90 | 95 | 100 | 90 | 95 |
| | 1.6 | 0 | 0 | 0 | 70 | 30 | 50 | 100 | 70 | 85 |
| | 0.4 | 0 | 0 | 0 | 0 | 0 | 0 | 0 | 0 | 0 |
| | 0.1 | 0 | 0 | 0 | 0 | 0 | 0 | 0 | 0 | 0 |
| | 0.025 | 0 | 0 | 0 | 0 | 0 | 0 | 0 | 0 | 0 |
| Solvent control | | 0 | 0 | 0 | 0 | 0 | 0 | 0 | 0 | 0 |
| Untreated Control | | 0 | 0 | 0 | 0 | 0 | 0 | 0 | 0 | 0 |

Rate is the ppm of the solution used to treat the vials.

TABLE 19

Synergistic Tick Efficacy of Fipronil with Different Dosages of Amitraz in DMSO Contact Test

| Compound | Rate ppm | 4 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| Fipronil + Amitraz (12.5 ppm) | 25 | 100 | 100 | 100 | 100 | 100 | 100 | 100 | 100 | 100 |
| | 6.25 | 100 | 100 | 100 | 100 | 100 | 100 | 100 | 100 | 100 |
| | 1.6 | 20 | 30 | 25 | 100 | 100 | 100 | 100 | 100 | 100 |
| | 0.4 | 0 | 0 | 0 | 100 | 100 | 100 | 100 | 100 | 100 |
| | 0.1 | 0 | 0 | 0 | 90 | 90 | 90 | 90 | 90 | 90 |
| | 0.025 | 0 | 0 | 0 | 50 | 50 | 50 | 50 | 50 | 50 |
| Fipronil + Amitraz (6.25 ppm) | 25 | 100 | 100 | 100 | 100 | 100 | 100 | 100 | 100 | 100 |
| | 6.25 | 80 | 70 | 75 | 100 | 100 | 100 | 100 | 100 | 100 |
| | 1.6 | 10 | 0 | 5 | 100 | 100 | 100 | 100 | 100 | 100 |
| | 0.4 | 0 | 0 | 0 | 100 | 100 | 100 | 100 | 100 | 100 |
| | 0.1 | 0 | 0 | 0 | 90 | 90 | 90 | 90 | 100 | 95 |
| | 0.025 | 0 | 0 | 0 | 60 | 40 | 50 | 60 | 60 | 60 |

TABLE 19-continued

Synergistic Tick Efficacy of Fipronil with Different Dosages of Amitraz in DMSO Contact Test

| Compound | Rate ppm | 4 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| Fipronil + | 25 | 100 | 100 | 100 | 100 | 100 | 100 | 100 | 100 | 100 |
| Amitraz | 6.25 | 40 | 30 | 35 | 100 | 100 | 100 | 100 | 100 | 100 |
| (3.13 ppm) | 1.6 | 0 | 0 | 0 | 100 | 100 | 100 | 100 | 100 | 100 |
| | 0.4 | 0 | 0 | 0 | 100 | 100 | 100 | 100 | 100 | 100 |
| | 0.1 | 0 | 0 | 0 | 100 | 100 | 100 | 100 | 100 | 100 |
| | 0.025 | 0 | 0 | 0 | 60 | 60 | 60 | 60 | 60 | 60 |
| Amitraz | 25 | 0 | 0 | 0 | 0 | 0 | 0 | 0 | 0 | 0 |
| | 12.5 | 0 | 0 | 0 | 0 | 0 | 0 | 0 | 0 | 0 |
| | 6.25 | 0 | 0 | 0 | 0 | 0 | 0 | 0 | 0 | 0 |
| | 3.13 | 0 | 0 | 0 | 0 | 0 | 0 | 0 | 0 | 0 |
| Solvent control | | 0 | 0 | 0 | 0 | 0 | 0 | 0 | 0 | 0 |
| Untreated Control | | 0 | 0 | 0 | 0 | 0 | 0 | 0 | 0 | 0 |

Table 20 below shows the calculated EC50 and EC90 values for this study for fipronil alone and three different combinations of fipronil with amitraz. As the table shows, combinations of fipronil with amitraz are significantly more potent than fipronil alone even just 4 hours after administration.

TABLE 20

EC50, EC90 and Synergistic Ratios of Fipronil with Different Dosages of Amitraz in Tick Contact Test

| Compound | 4 hour Eval | | 24 hour Eval | | 48 hour Eval | |
|---|---|---|---|---|---|---|
| | EC50 | EC90 | EC50 | EC90 | EC50 | EC90 |
| fipronil | 12.5 | >25 | 1.61 | 3.7 | 1.19 | 1.73 |
| fipronil + Amitraz (12.5 ppm) | 1.7 | 1.91 | 0.025 | 0.098 | 0.025 | 0.098 |
| fipronil + Amitraz (6.25 ppm) | 4.31 | 9.03 | 0.025 | 0.098 | <0.025 | 0.066 |
| fipronil + Amitraz (3.13 ppm) | 6.48 | 7.31 | <0.025 | 0.031 | <0.025 | 0.031 |
| Synergistic Ratios | | | | | | |
| fipronil with Amitraz at 12.5 ppm | 7.35 | >13 | 64.4 | 37.8 | 47.6 | 17.7 |
| fipronil with Amitraz at 6.25 ppm | 2.9 | >2.8 | 64.4 | 37.8 | >47.6 | 26.2 |
| fipronil with Amitraz at 3.13 ppm | 1.9 | >3.4 | >64.4 | 119.4 | >47.6 | 55.8 |

Synergistic ratio is EC50 or EC90 alone divided by EC50 or EC90 with Amitraz.

Example 14

Tick Motility of Synergistic Formulations Comprising Amitraz and Fipronil

The synergistic efficacy of combinations of fipronil and amitraz was demonstrated by measuring the motility of ticks exposed to an environment containing different amounts of fipronil alone, amitraz alone or combinations of fipronil and amitraz. An imaging system was used for the automated analysis of tick motility in response to amitraz and fipronil treatments to remove the subjective interpretation of manual test evaluation. The study was designed to evaluate the affect of amitraz and fipronil alone and in combination, as compared to a control, on the motility of ticks over time.

The motility of adult *Rhipicephalus sanguineus* was compared for amitraz-only, fipronil-only and the combination of fipronil and amitraz in a petri dish assay using the imaging system. The assay was run using a fixed dilution of amitraz (0.32 ug/cm$^2$), with serial dilutions of fipronil (1.3, 0.33, 0.08, 0.02, or 0.005 ug/cm$^2$) alone and in combination with the fixed dilution of amitraz. Six independent replications were conducted.

A plate holding four petri dishes was custom made for the imaging system. At each time point the plate holding four petri dishes was placed on the imaging system and evaluated for motility. The set up of the plate for each evaluation is illustrated below in Table 21.

TABLE 21

Tick Motility Set Up

| Petri Dish Designation | Plate 1 | Plate 2 | Plate 3 | Plate 4 | Plate 5 |
|---|---|---|---|---|---|
| A1 | Ethanol Control | Ethanol Control | Ethanol Control | Ethanol Control | Ethanol Control |
| A2 | Amitraz 0.32 µg/cm$^2$ | Amitraz 0.32 µg/cm$^2$ | Amitraz 0.32 µg/cm$^2$ | Amitraz 0.32 µg/cm$^2$ | Amitraz 0.32 µg/cm$^2$ |
| B1 | Fipronil 1.3 µg/cm$^2$ + Amitraz 0.32 µg/cm$^2$ | Fipronil 0.33 µg/cm$^2$ + Amitraz 0.32 µg/cm$^2$ | Fipronil 0.08 µg/cm$^2$ + Amitraz 0.32 µg/cm$^2$ | Fipronil 0.02 µg/cm$^2$ + Amitraz 0.32 µg/cm$^2$ | Fipronil 0.005 µg/cm$^2$ + Amitraz 0.32 µg/cm$^2$ |
| B2 | Fipronil 1.3 µg/cm$^2$ | Fipronil 0.33 µg/cm$^2$ | Fipronil 0.08 µg/cm$^2$ | Fipronil 0.02 µg/cm$^2$ | Fipronil 0.005 µg/cm$^2$ |

For Dish A1, a volume of 625 µL of ethanol was used to treat the tops and 625 µL to treat the bottoms of the petri dish. All solutions were formulated in 100% ethanol. For Dish A2, a volume of 125 µL of the 25 ppm amitraz solution was used to treat the tops and 125 µL to treat the bottoms of the petri dish. For Dish B1, the top and bottom portions of the petri dishes were each treated with 500 µL of the 25 ppm solution of fipronil (serially diluted for each Plate 1-5) and 125 µL of the 25 ppm solution of amitraz. And for Dish B2, each of the top and bottom portions of the petri dishes were treated with 500 µL of the 25 ppm solution of fipronil (serially diluted for each Plate 1-5). After application of the corresponding solution to the petri dishes, the petri dishes were left open under a fan and allowed to dry for 1 hour. After drying, the dishes were infested with 10 adult *Rhipicephalus sanguineus* (supplied by Ecto Services, Inc. Henderson, N.C.). The ticks were left undisturbed for 1 hour before evaluation in the imaging system. Between evaluations ticks were maintained at approximately 21° C. and 60% RH.

After the initial hour, each Plate 1-5 was sequentially placed into the imaging system for evaluation. Image processing calculates the change in movement of the ticks between each image. The value generated is equal to the movement in each petri dish during the image time. The ticks in each individual petri dish were then stimulated to move by breathing/exhaling into the plate. After stimulation, the plates were placed back into the imaging system for another evaluation to determine if the treatment affected the tick's ability to move. Image capture was repeated as in the pre-stimulated evaluation.

Evaluations were made at 1, 4, 18, and 24 hours post infest (hpi) for 3 trials. For 3 trials the 4 hour evaluation was not done and for 3 trials the third evaluation was done at 21 to 22 hours. Raw data values were exported from the imaging system and comparative analysis of treatments over time was conducted. The geometric means of the movement values for stimulated ticks from all time points are shown in Table 22.

TABLE 22

Geometric Means of movement values for stimulated ticks at all time points.

| Hours Post Infestation | Treatment Group | Geometric Mean |
|---|---|---|
| 1 | Control | 43,300 |
| 1 | Amitraz | 56,900 |
| 1 | Fipronil + Amitraz | 59,400 |
| 1 | Fipronil | 51,000 |
| 4 | Control | 30,600 |
| 4 | Amitraz | 44,300 |
| 4 | Fipronil + Amitraz | 38,500 |
| 4 | Fipronil | 29,000 |
| 18 | Control | 30,400 |
| 18 | Amitraz | 33,200 |
| 18 | Fipronil + Amitraz | 3,700 |
| 18 | Fipronil | 17,400 |
| 21-22 | Control | 25,000 |
| 21-22 | Amitraz | 30,300 |
| 21-22 | Fipronil + Amitraz | 1,990 |
| 21-22 | Fipronil | 21,200 |
| 24 | Control | 27,600 |
| 24 | Amitraz | 34,300 |
| 24 | Fipronil + Amitraz | 598 |
| 24 | Fipronil | 19,700 |

Typically adult *R. sanguineus* will rest unless there is a source of stimulation, such as movement or $CO_2$. The amitraz-only treated ticks had an increase in motility as compared to the solvent control treated ticks over time (FIG. 11). Fipronil-only treated ticks showed a reduction in motility directly correlated to the dose response over time. At 18 and 21 hpi the doses as low as 0.08 µg/cm$^2$ of fipronil in the fipronil plus amitraz combination show the greatest reduction in motility. The ticks in the fipronil treatment group were not affected in this manner. For the 18, 21-22, and 24 hpi, evaluations only the highest dose of fipronil (1.3 µg/cm$^2$) had consistently low motility values after stimulation. The difference in the dose response for fipronil and fipronil plus amitraz illustrates that a lower amount of fipronil was adequate in combination with amitraz to cause the ticks to become nonmotile. This greater reduction in motility for fipronil plus amitraz was also measured at the 24 hpi time point down to the 0.02 µg/cm$^2$ dose of fipronil tested. Based on these results, the combination of fipronil and amitraz led to a greater reduction in motility at the later time points (FIG. 11). This results in a synergistic effect between the fipronil and amitraz.

Example 15

Tick Efficacy of Synergistic Formulations Comprising Amitraz and Compound 1—Tick DMSO Contact Assay Scintillation vials were treated with commercial and experimental compounds using the same procedure described in Example 12 above. The treated vials were used to determine the contact toxicity of compounds against adult brown dog ticks (*Rhipicephalus sanguineus*). The ticks were supplied by Ecto Services Inc. Henderson, N.C.

Unfed adult ticks were released into a metal pan and 10 living ticks were aspirated into each vial. The vials were visually evaluated at 6, 24 and 48 hours post infestation for living/dead ticks and percent mortality was determined. Two replicates were tested for each treatment and the results were averaged. Ticks were stimulated by gently exhaling in the vials. The efficacy of Compound 1 alone is shown in Table 23 below. The synergistic efficacy of Compound 1 with amitraz is shown in Table 24. Within the same time period, the addition of amitraz to an equal dosage of compound 1 increased mean mortality. The EC50 and EC90 values, and synergistic ratios of compound 1 and compound 1 with amitraz are shown in Table 25.

TABLE 23

Tick Efficacy of Compound 1 in DMSO Contact Test
Rate is the ppm of the solution used to treat the vials.

| | | 6 hour % Mortality | | | 24 hour % Mortality | | | 48 hour % Mortality | | |
|---|---|---|---|---|---|---|---|---|---|---|
| Compound | Rate ppm | Rep 1 | Rep 2 | Avg. % Mortality | Rep 1 | Rep 2 | Avg. % Mortality | Rep 1 | Rep 2 | Avg. % Mortality |
| 1 | 25 | 80 | 60 | 70 | 90 | 100 | 95 | 100 | 100 | 100 |
| | 6.25 | 10 | 10 | 10 | 50 | 100 | 75 | 70 | 100 | 85 |
| | 1.6 | 0 | 0 | 0 | 30 | 40 | 35 | 30 | 40 | 35 |
| | 0.4 | 0 | 0 | 0 | 30 | 0 | 15 | 30 | 0 | 15 |
| | 0.1 | 0 | 0 | 0 | 0 | 0 | 0 | 0 | 0 | 0 |
| | 0.025 | 0 | 0 | 0 | 0 | 0 | 0 | 0 | 0 | 0 |
| | 0.006 | 0 | 0 | 0 | 0 | 0 | 0 | 0 | 0 | 0 |
| | 0.0016 | 0 | 0 | 0 | 0 | 0 | 0 | 0 | 0 | 0 |

TABLE 23-continued

Tick Efficacy of Compound 1 in DMSO Contact Test
Rate is the ppm of the solution used to treat the vials.

| Compound | Rate ppm | 6 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| Solvent control | | 0 | 0 | 0 | 0 | 0 | 0 | 0 | 0 | 0 |
| Untreated Control | | 0 | 0 | 0 | 0 | 0 | 0 | 0 | 0 | 0 |

TABLE 24

Synergistic Tick Efficacy of Compound 1 with Amitraz in DMSO Contact Test.

| Compound | Rate ppm | 6 hour Eval | | | 24 hour Eval | | | 48 hour Eval | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| 1 + Amitraz (12.5 ppm) | 25 | 100 | 100 | 100 | 100 | 100 | 100 | 100 | 100 | 100 |
| | 6.25 | 100 | 100 | 100 | 100 | 100 | 100 | 100 | 100 | 100 |
| | 1.6 | 50 | 50 | 50 | 100 | 100 | 100 | 100 | 100 | 100 |
| | 0.4 | 20 | 0 | 10 | 100 | 100 | 100 | 100 | 100 | 100 |
| | 0.1 | 0 | 0 | 0 | 90 | 80 | 85 | 90 | 80 | 85 |
| | 0.025 | 0 | 0 | 0 | 40 | 70 | 55 | 40 | 70 | 55 |
| | 0.006 | 0 | 0 | 0 | 20 | 40 | 30 | 20 | 40 | 30 |
| | 0.0016 | 0 | 0 | 0 | 0 | 0 | 0 | 10 | 20 | 15 |
| Amitraz | 25 | 0 | 0 | 0 | 0 | 0 | 0 | 10 | 10 | 10 |
| | 12.5 | 0 | 0 | 0 | 0 | 0 | 0 | 0 | 0 | 0 |
| | 6.25 | 0 | 0 | 0 | 0 | 0 | 0 | 0 | 0 | 0 |
| Solvent control | | 0 | 0 | 0 | 0 | 0 | 0 | 0 | 0 | 0 |
| Untreated Control | | 0 | 0 | 0 | 0 | 0 | 0 | 0 | 0 | 0 |

Rate is the ppm of the solution used to treat the vials.

TABLE 25

EC50, EC90 and Synergistic Ratios of Tick Efficacy Formulations of Compound 1 with Amitraz in DMSO Contact Test.

| Compound | 6 hour Eval | | 24 hour Eval | | 48 hour Eval | |
|---|---|---|---|---|---|---|
| | EC50 | EC90 | EC50 | EC90 | EC50 | EC90 |
| 1 | 17 | >25 | 2.49 | 16.6 | 2.17 | 9.71 |
| 1 + Amitraz (12.5 ppm) | 1.54 | 4.37 | 0.0184 | 0.149 | 0.0163 | 0.193 |
| Synergistic Ratio for compound 1 | 11 | >5.72 | 135.3 | 111.4 | 133.1 | 50.3 |

Synergistic ratio is EC50 or EC90 alone divided by EC50 or EC90 with Amitraz.

Formulations of compound 1 with lower concentrations of Amitraz also exhibited synergistic activity. Example 16 provides data showing unexpected and improved efficacy of compound 1 with low concentrations of Amitraz. The EC90 values are substantially improved using compound 1.

Example 16

Tick Efficacy of Synergistic Formulations with Reduced Dosages of Acaricide—Tick DMSO Contact Assay The assay protocol was similar to the protocol of Example 15, with the following exceptions: 1) The vials were visually evaluated at 4, 24 and 48 hours post infestation for living/dead ticks and percent mortality was determined, and 2) the acaricide (amitraz) was added at dosages of 12.5 ppm, 6.25 ppm, and 3.13 ppm.

The efficacy of Compound 1 alone is shown in Table 26 below. The synergistic efficacy of Compound 1 with different dosages of amitraz is shown in Table 27. Within the same time period, the addition of amitraz to an equal dosage of compound 1 increased mean mortality. The EC50 and EC90 values of compound 1 and compound 1 with different dosages of amitraz are shown in Table 28, which clearly indicates superior efficacy.

TABLE 26

Tick Efficacy of Compound 1 in DMSO Contact Test

| Compound | Rate ppm | 4 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| 1 | 25 | 90 | 70 | 80 | 100 | 100 | 100 | 100 | 100 | 100 |
| | 6.25 | 40 | 70 | 55 | 100 | 100 | 100 | 100 | 100 | 100 |
| | 1.6 | 30 | 20 | 25 | 100 | 30 | 65 | 100 | 100 | 100 |

TABLE 26-continued

Tick Efficacy of Compound 1 in DMSO Contact Test

| Compound | Rate ppm | 4 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| | 0.4 | 0 | 0 | 0 | 0 | 0 | 0 | 20 | 0 | 10 |
| | 0.1 | 0 | 0 | 0 | 0 | 0 | 0 | 0 | 0 | 0 |
| | 0.025 | 0 | 0 | 0 | 0 | 0 | 0 | 0 | 0 | 0 |
| Solvent control | | 0 | 0 | 0 | 0 | 0 | 0 | 0 | 0 | 0 |
| Untreated Control | | 0 | 0 | 0 | 0 | 0 | 0 | 0 | 0 | 0 |

Rate is the ppm of the solution used to treat the vials.

TABLE 27

Synergistic Tick Efficacy of Compound 1 with Different Dosages of Amitraz in DMSO Contact Test.

| Cmpd. | Rate ppm | 4 hour % Mortality | | | 24 hour % Mortality | | | 48 hour % Mortality | | |
|---|---|---|---|---|---|---|---|---|---|---|
| | | Rep 1 | Rep 2 | Avg. % Mortality | Rep 1 | Rep 2 | Avg. % Mortality | Rep 1 | Rep 2 | Avg. % Mortality |
| 1 + Amitraz (12.5 ppm) | 25 | 100 | 90 | 95 | 100 | 100 | 100 | 100 | 100 | 100 |
| | 6.25 | 90 | 90 | 90 | 100 | 100 | 100 | 100 | 100 | 100 |
| | 1.6 | 60 | 50 | 55 | 100 | 100 | 100 | 100 | 100 | 100 |
| | 0.4 | 0 | 0 | 0 | 100 | 100 | 100 | 100 | 100 | 100 |
| | 0.1 | 0 | 0 | 0 | 90 | 100 | 95 | 90 | 100 | 95 |
| | 0.025 | 0 | 0 | 0 | 80 | 60 | 70 | 80 | 60 | 70 |
| 1 + Amitraz (6.25 ppm) | 25 | 90 | 100 | 95 | 100 | 100 | 100 | 100 | 100 | 100 |
| | 6.25 | 80 | 90 | 85 | 100 | 100 | 100 | 100 | 100 | 100 |
| | 1.6 | 30 | 70 | 50 | 100 | 100 | 100 | 100 | 100 | 100 |
| | 0.4 | 10 | 30 | 20 | 100 | 100 | 100 | 100 | 100 | 100 |
| | 0.1 | 0 | 10 | 5 | 100 | 100 | 100 | 100 | 100 | 100 |
| | 0.025 | 0 | 0 | 0 | 80 | 80 | 80 | 80 | 80 | 80 |
| 1 + Amitraz (3.13 ppm) | 25 | 100 | 100 | 100 | 100 | 100 | 100 | 100 | 100 | 100 |
| | 6.25 | 100 | 100 | 100 | 100 | 100 | 100 | 100 | 100 | 100 |
| | 1.6 | 40 | 70 | 55 | 100 | 100 | 100 | 100 | 100 | 100 |
| | 0.4 | 0 | 10 | 5 | 100 | 100 | 100 | 100 | 100 | 100 |
| | 0.1 | 0 | 0 | 0 | 100 | 100 | 100 | 100 | 100 | 100 |
| | 0.025 | 0 | 0 | 0 | 80 | 50 | 65 | 80 | 80 | 80 |
| Amitraz | 12.5 | 0 | 0 | 0 | 0 | 0 | 0 | 0 | 0 | 0 |
| | 6.25 | 0 | 0 | 0 | 0 | 0 | 0 | 0 | 0 | 0 |
| | 3.13 | 0 | 0 | 0 | 0 | 0 | 0 | 0 | 0 | 0 |

Rate is the ppm of the solution used to treat the vials.

TABLE 28

EC50, EC90 and Synergistic Ratios of Tick Efficacy Formulations of Compound 1 with Different Dosages of Amitraz in DMSO Contact Test.

| Compound | 4 hour Eval | | 24 hour Eval | | 48 hour Eval | |
|---|---|---|---|---|---|---|
| | EC50 | EC90 | EC50 | EC90 | EC50 | EC90 |
| 1 | 5.42 | >25 | 1.54 | 1.75 | 0.45 | 0.51 |
| 1 + Amitraz (12.5 ppm) | 1.51 | 4.13 | <0.025 | 0.06 | <0.025 | 0.06 |
| 1 + Amitraz (6.25 ppm) | 1.50 | 10.78 | <0.025 | 0.026 | <0.025 | 0.026 |
| 1 + Amitraz (3.13 ppm) | 1.47 | 3.45 | <0.025 | 0.03 | <0.025 | 0.026 |
| | Synergistic ratios | | | | | |
| 1 + Amitraz (12.5 ppm) | 3.59 | >6.05 | >61.6 | 29.2 | >18 | 8.5 |
| 1 + Amitraz (6.25 ppm) | 3.61 | >2.3 | >61.6 | 67.3 | >18 | 19.6 |
| 1 + Amitraz (3.13 ppm) | 3.69 | >7.25 | >61.6 | 58.3 | >18 | 19.6 |

Synergistic ratio is EC50 or EC90 alone divided by EC50 or EC90 with Amitraz.

Example 17

Formulations for Dual Cavity Container

One means for topically delivering the inventive combination of active ingredients such as those described in Examples above is to utilize a dual cavity container.

In one embodiment of the use of a dual cavity container, the first cavity of the dual-cavity container contains a clear colorless/light yellow composition comprising of amitraz and octyl benzoate as a solvent.

| Ingredients | Function | % |
|---|---|---|
| Amitraz | Active | 20.0 w/v |
| Octyl benzoate | Solvent | q.s. 100 |

This composition may also comprise 2,4-dimethylaniline, formamidine-2',4'-xylidide, N-methyl-N'-(2,4-xylyl)formamidine, and/or N,N'-bis(2,4-xylyl)formamidine; for example, in amounts ranging from about 0.1% to about 8% of the 20% w/v. In one embodiment of this composition, water may be present; for example, in an amount of up to about 0.06% w/w. In another embodiment of this composition, water may be present, for example, in an amount of up to about 0.4% w/w. The composition may also have a maximum acid value of about 0.14.

In the second cavity of the dual-cavity container is a clear amber composition comprising fipronil and s-methoprene

| Ingredients | Function | % |
| --- | --- | --- |
| Fipronil | Active | 10.0 w/v |
| s-Methoprene | Active | 9.0 w/v |
| Solvent | Solvent | q.s. 100 |

This composition may also include the antioxidants BHA and BHT. The amount of BHA if present ranges from 0.016-0.022% w/v and the amount for BHT if present ranges from 0.008-0.011% w/v. In one embodiment of this composition, water may be present in an amount of up to 1.5% w/w. In another embodiment of this composition, water may be present in an amount of up to 10% w/w.

In another embodiment of the use of a dual cavity container, the first cavity of the dual-cavity container contains a clear colorless/light yellow composition comprising of amitraz and octyl benzoate as a solvent.

| Ingredients | Function | % |
| --- | --- | --- |
| Amitraz | Active | 20.0 w/v |
| Octyl benzoate | Solvent | q.s. 100 |

This composition may also comprise 2,4-dimethylaniline, formamidine-2',4'-xylidide, N-methyl-N'-(2,4-xylyl)formamidine, and/or N,N'-bis(2,4-xylyl)formamidine; for example, in amounts ranging from about 0.1% to about 8% of the 20% w/v. In one embodiment of this composition, water may be present; for example, in an amount of up to about 0.06% w/w. In another embodiment of this composition, water may be present, for example, in an amount of up to about 0.4% w/w. The composition may also have a maximum acid value of about 0.14.

In the second cavity of the dual-cavity container is a clear amber composition comprising fipronil and s-methoprene

| Ingredients | Function | % |
| --- | --- | --- |
| Fipronil | Active | 9.8 w/w |
| s-Methoprene | Active | 8.82 w/w |
| Solvent | Solvent | q.s. 100 |

This composition may also include the antioxidants BHA and BHT. The amount of BHA if present ranges from 0.001-0.03% w/v and the amount for BHT if present ranges from 0.002-0.018% w/v. In one embodiment of this composition, water may be present in an amount of up to 1.5% w/w. In another embodiment of this composition, water may be present in an amount of up to 10% w/w.

The invention is further described by the following numbered paragraphs:

1. A veterinary formulation for treating or preventing a parasitic infestation in an animal comprising:
  (a) a 1-aryl-5-alkyl or 5-haloalkylpyrazole of formula (IA) or a veterinarily acceptable salt thereof,

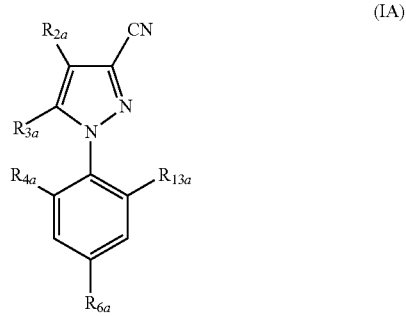

(IA)

wherein:
  $R_{2a}$ is —$S(O)_m R_{11a}$;
  $R_{3a}$ is methyl, ethyl or $C_1$-$C_4$ haloalkyl;
  $R_{4a}$ is halogen;
  $R_{6a}$ is $C_1$-$C_4$ alkyl or haloalkyl;
  $R_{13a}$ is halogen;
  $R_{11a}$ is $C_1$-$C_4$ haloalkyl; and
  m is 0, 1 or 2;
  (b) a veterinarily acceptable carrier; and
  (c) optionally a crystallization inhibitor.

2. A composition for the treatment or prevention of a parasitic infestation in an animal comprising at least one 1-arylpyrazole compound in a first veterinarily acceptable carrier, at least one formamidine compound in a second veterinarily acceptable carrier, and optionally at least one crystallization inhibitor(s), wherein the 1-arylpyrazole compound(s) and first veterinarily acceptable carrier are isolated and not in fluid communication with the formamidine compound(s) and the second veterinarily acceptable carrier.

3. The composition of paragraph 2, wherein the one or more 1-arylpyrazole compound(s) and the first veterinarily acceptable carrier are in one cavity of a dual-cavity container and the one or more formamidine compound(s) and the second veterinarily acceptable carrier are in a second cavity of a dual-cavity container, wherein the first cavity is defined by a front wall and a divider wall; and the second cavity is defined by a rear wall and the divider wall.

4. The composition of paragraph 2 or 3, wherein the at least one 1-arylpyrazole compounds has formula (IB):

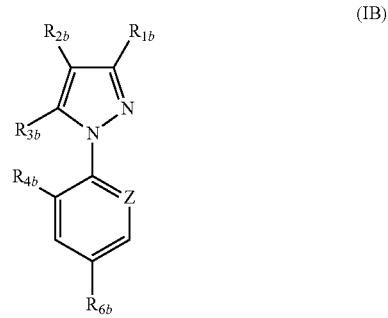

(IB)

wherein:

$R_{1b}$ is alkyl, CN or halogen;

$R_{2b}$ is $S(O)_nR_{14b}$ or 4,5-dicyanoimidazol-2-yl or haloalkyl;

$R_{14b}$ is alkyl or haloalkyl;

$R_{3b}$ is a hydrogen, halogen, —$NR_{7b}R_{8b}$, —$S(O)_mR_{9b}$, —$C(O)R_{9b}$, —$C(O)OR_{9b}$, alkyl, haloalkyl, —$OR_{10b}$ or an —$N=C(R_{11b})(R_{12b})$;

$R_{6b}$ is a halogen, haloalkyl, haloalkoxy, $S(O)_qCF_3$ or $SF_5$ group;

$R_{7B}$ and $R_{8B}$ independently represent a hydrogen, alkyl, haloalkyl, —C(O)alkyl, —$S(O)_rCF_3$, acyl or alkoxycarbonyl; or $R_{7b}$ and $R_{8b}$ can together form a divalent alkylene radical which is optionally interrupted by one or two divalent heteroatoms;

$R_{9b}$ is an alkyl or haloalkyl;

$R_{10b}$ is hydrogen, alkyl or haloalkyl;

$R_{11b}$ is hydrogen or alkyl radical;

$R_{12b}$ is an optionally substituted aryl or an optionally substituted heteroaryl group;

$R_{4b}$ and $R_{13b}$ represent, independently of one another, hydrogen, halogen CN or $NO_2$;

m, n, q and r represent, independently of one another, an integer equal to 0, 1 or 2; and Z represents a trivalent nitrogen atom or a C—$R_{13b}$ radical, the three other valencies of the carbon atom forming part of the aromatic ring.

5. The composition of paragraph 4, wherein:
   $R_{1b}$ is methyl, CN or halogen;
   $R_{2b}$ is $S(O)_nR_{14b}$;
   $R_{14b}$ is $C_1$-$C_6$-alkyl or $C_1$-$C_6$-haloalkyl;
   $R_{3b}$ is —$NR_{7b}R_{8b}$,
   $R_{7b}$ and $R_{8b}$ independently represent a hydrogen, $C_1$-$C_6$-alkyl, $C_1$-$C_6$-haloalkyl, —$C(O)C_1$-$C_6$-alkyl, —$S(O)_rCF_3$, $C_1$-$C_6$-acyl or $C_1$-$C_6$-alkoxycarbonyl radical;
   $R_{6b}$ is a halogen, $C_1$-$C_6$-haloalkyl, or $C_1$-$C_6$-haloalkoxy;
   m, n, q and r represent, independently of one another, an integer equal to 0 or 1; and
   Z is a C—$R_{13b}$ radical.

6. The composition of paragraph 4, wherein:
   $R_{1b}$ is methyl, CN or halogen;
   $R_{2b}$ is $S(O)_nR_{14b}$;
   $R_{14b}$ is $C_1$-$C_6$-alkyl or $C_1$-$C_6$-haloalkyl;
   $R_{3b}$ is alkyl or haloalkyl;
   $R_{6b}$ is a halogen, $C_1$-$C_6$-haloalkyl, or $C_1$-$C_6$-haloalkoxy;
   m, n, q and r represent, independently of one another, an integer equal to 0 or 1; and
   Z is a C—$R_{13b}$ radical.

7. The composition of paragraph 2, wherein the first veterinarily acceptable carrier comprises acetone, acetonitrile, benzyl alcohol, ethanol, isopropanol, diisobutyl adipate, diisopropyl adipate, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone, N-methylpyrrolidone, diethylene glycol monoethyl ether, triacetin, butyl acetate, octyl acetate, propylene carbonate, butylene carbonate, dimethyl sulfoxide, an amide, dimethylformamide, dimethylacetamide, or any combination thereof.

8. The composition of paragraph 2, wherein the second veterinarily acceptable carrier comprises aryl ethers, alkoxybenzene compounds; aliphatic carboxylic acid esters, aromatic carboxylic acid esters, aliphatic ketones, cyclic ketones, or mixtures thereof.

9. The composition of paragraph 2, wherein the second veterinarily acceptable carrier comprises methoxybenzene, butyl acetate, benzyl acetate, methyl isobutyl ketone, ethyl benzoate, benzyl benzoate, octyl acetate, or mixtures thereof.

10. The composition of paragraph 2, wherein the second veterinarily acceptable carrier comprises an aprotic solvent with a dielectric constant of about 2 to about 30.

11. A composition for the treatment and prevention of a parasitic infestation in an animal comprising at least one formamidine compound(s), at least one 1-arylpyrazole compound(s) of formula (IA), or veterinarily acceptable salts thereof,

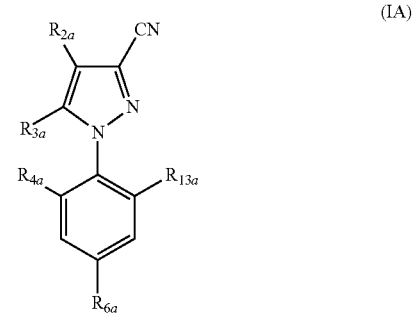

(IA)

wherein:
   $R_{2a}$ is —$S(O)_mR_{11a}$;
   $R_{3a}$ is methyl, ethyl or $C_1$-$C_4$ haloalkyl;
   $R_{4a}$ is halogen;
   $R_{6a}$ is $C_1$-$C_4$ alkyl or haloalkyl;
   $R_{13a}$ is halogen;
   $R_{11a}$ is $C_1$-$C_4$ haloalkyl; and
   m is 0, 1 or 2;

at least one veterinarily acceptable carriers; and optionally a crystallization inhibitor.

12. The composition of paragraph 2 or 11, wherein the at least one formamidine compound has the formula (II):

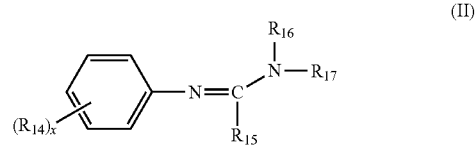

(II)

wherein:

x is an integer from 0-5;

$R_{14}$ is alkyl, halogen or —OC(=O)$NR_aR_b$, wherein $R_a$ and $R_b$ are independently hydrogen or alkyl;

$R_{15}$ is hydrogen or alkyl;

$R_{16}$ is hydrogen or alkyl; and $R_{17}$ is hydrogen, alkyl or

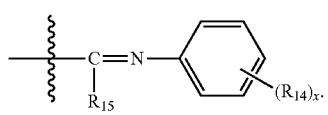

13. The composition of paragraph 2 or 11, wherein the at least one formamidine compound comprises amitraz, formetanate, chloromebuform, formparanate or chlodimeform.

14. The composition of paragraph 2 or 11, wherein the at least one 1-arylpyrazole compound(s) is combined with a first veterinarily acceptable carrier and the at least one formamidine compounds is combined with a second veterinarily acceptable carrier; and wherein the 1-arylpyrazole compound(s) and the first veterinarily acceptable carrier are compartmentalized together and not in fluid communication with, the at least one formamidine compound(s) and the second veterinarily acceptable carrier.

15. A composition for the treatment and prevention of a parasitic infestation in an animal comprising at least one formamidine compound and at least one aprotic solvent(s) with a dielectric constant of about 2 to about 30, wherein the composition is stable for at least 24 months at 25° C.

16. The composition of paragraph 15, wherein the at least one formamidine compound is amitraz.

17. The composition of paragraph 15, wherein the aprotic solvent(s) with a dielectric constant of about 2 to about 30 has a water content of less than about 0.05% (w/w).

18. The composition of paragraph 15, wherein the at least one aprotic solvent(s) with a dielectric constant of about 2 to about 30 is a $C_1$-$C_{10}$ carboxylic acid ester, a phenyl carboxylic acid ester, a carboxylic acid benzyl ester, a benzoic acid $C_1$-$C_4$ alkyl ester, a $C_1$-$C_6$ saturated aliphatic ketone, or a mixture thereof.

19. The composition of paragraph 15, comprising two or more aprotic solvents with a dielectric constant of about 2 to about 30, wherein a dissipation of an unpleasant odor from the composition occurs within about 5 minutes to within about 25 minutes after application.

20. A method for the treatment or prevention of a parasitic infestation in an animal comprising administering an effective amount of the composition of paragraph 2 or 11 to the animal in need thereof.

21. The method of paragraph 20, wherein the at least one 1-arylpyrazole compound is fipronil.

22. The method of paragraph 20, wherein the at least one formamidine compound is amitraz.

23. The method of paragraph 20, wherein the composition is administered using a dual-cavity container, wherein the 1-arylpyrazole compound(s) and the first veterinarily acceptable carrier are administered from a first cavity of the dual cavity container and the formamidine compound(s) and the second veterinarily acceptable carrier are administered from a second cavity of the dual cavity container.

24. The method of paragraph 22, wherein the 1-arylpyrazole compound(s) and the formamidine compound(s) are administered simultaneously.

25. A method for the treatment or prevention of a parasitic infestation in an animal comprising administering an effective amount of the composition of paragraph 11 to the animal in need thereof.

26. The method of paragraph 25, wherein the at least one 1-arylpyrazole compound(s) is in a first veterinarily acceptable carrier, and the at least one formamidine compound(s) is in a second veterinarily acceptable carrier; wherein the 1-arylpyrazole compound(s) and first veterinarily acceptable carrier are compartmentalized together and not in fluid communication with, the formamidine compound(s) and the second veterinarily acceptable carrier.

27. The method of paragraph 26, wherein the 1-arylpyrazole compound(s) and the formamidine compound(s) are administered simultaneously.

28. The method of paragraph 25, wherein the at least one formamidine compound is amitraz.

29. A method for the treatment or prevention of a parasitic infestation in an animal comprising administering to the animal an effective amount of a composition comprising at least one 1-arylpyrazole compound in a first veterinarily acceptable carrier and at least one formamidine compound in a second veterinarily acceptable carrier from a dual-cavity container; wherein the at least one 1-arylpyrazole compound(s) and the first veterinarily acceptable carrier are in one cavity of the dual-cavity container and the at least one formamidine compound and the second veterinarily acceptable carrier is in a second cavity of the dual-cavity container; and wherein the first cavity is defined by a front wall and a divider wall; and the second cavity is defined by a rear wall and the divider wall.

30. The method of paragraph 29, wherein the at least one 1-arylpyrazole compound is fipronil.

31. The method of paragraph 29, wherein the at least one formamidine compound(s) is amitraz.

32. The method of paragraph 29, wherein the 1-arylpyrazole compound(s) and the formamidine compound(s) are administered simultaneously.

33. A kit for the treatment or prevention of a parasitic infestation in an animal, comprising: at least one 1-arylpyrazole compound in a first veterinarily acceptable carrier, at least one formamidine compound in a second veterinarily acceptable carrier, and a multiple cavity container; wherein the at least one 1-arylpyrazole compound(s) in a first veterinarily acceptable carrier is in a first cavity of the multiple cavity container and the at least one formamidine compound(s) in a second veterinarily acceptable carrier is in a second cavity of the multiple cavity container; and wherein the first cavity is defined by a front wall and a divider wall; and the second cavity defined by a rear wall and the divider wall.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:
1. A kit for the treatment or prevention of a parasitic infestation in an animal, comprising:
(i) at least one 1-arylpyrazole compound of formula (IB) in a first veterinarily acceptable carrier:

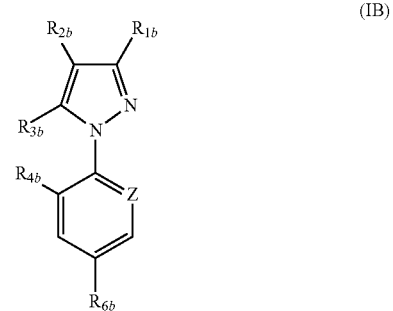

wherein:
$R_{1b}$ is alkyl, CN or halogen;
$R_{2b}$ is $S(O)_n R_{14b}$ or 4,5-dicyanoimidazol-2-yl or haloalkyl;
$R_{14b}$ is alkyl or haloalkyl;

$R_{3b}$ is a hydrogen, halogen, —$NR_{7b}R_{8b}$, —$S(O)_mR_{9b}$, —$C(O)R_{9b}$, —$C(O)OR_{9b}$, alkyl, haloalkyl, —$OR_{10b}$ or an —$N=C(R_{11b})(R_{12b})$;

$R_{6b}$ is a halogen, haloalkyl, haloalkoxy, $S(O)_qCF_3$ or $SF_5$ group;

$R_{7b}$ and $R_{8b}$ independently represent a hydrogen, alkyl, haloalkyl, —$C(O)$alkyl, —$S(O)_rCF_3$, acyl or alkoxycarbonyl; or $R_{7b}$ and $R_{8b}$ can together form a divalent alkylene radical which is optionally interrupted by one or two divalent heteroatoms;

$R_{9b}$ is an alkyl or haloalkyl;

$R_{10b}$ is hydrogen, alkyl or haloalkyl;

$R_{11b}$ is hydrogen or alkyl radical;

$R_{12b}$ is an optionally substituted aryl or an optionally substituted heteroaryl group;

$R_{4b}$ and $R_{13b}$ represent, independently of one another, hydrogen, halogen CN or $NO_2$;

m, n, q and r represent, independently of one another, an integer equal to 0, 1 or 2; and Z represents a trivalent nitrogen atom or a C—$R_{13b}$ radical, the three other valencies of the carbon atom forming part of the aromatic ring;

(ii) at least one formamidine compound of formula (II) in a second veterinarily acceptable carrier:

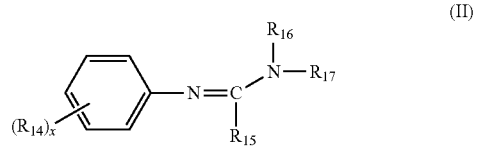

(II)

wherein:
x is an integer from 0-5;
$R_{14}$ is alkyl, halogen or —$OC(=O)NR^aR_b$,
wherein $R_a$ and $R_b$ are independently hydrogen or alkyl;
$R_{15}$ is hydrogen or alkyl;
$R_{16}$ is hydrogen or alkyl; and
$R_{17}$ is hydrogen, alkyl or

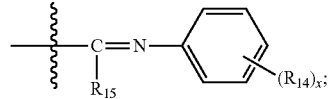

and
(iii) a dual-cavity container;
wherein the dual-cavity container comprises a front wall, a divider wall, a rear wall and an opening mechanism at one end of the container; the first cavity of the dual-cavity container is defined by the front wall and the divider wall; the second cavity of the dual-cavity container is defined by the rear wall and the divider wall; and wherein the front wall, the divider wall and the rear wall are coupled along part of their perimeter to define the two cavities;
the 1-arylpyrazole compound(s) of formula (IB) in the first veterinarily acceptable carrier is in the first cavity of the dual-cavity container and the formamidine compound(s) of formula (II) in the second veterinarily acceptable carrier is in the second cavity of the dual-cavity container; and wherein the 1-arylpyrazole compound(s) of formula (IB) in the first veterinarily acceptable carrier and the formamidine compound(s) of formula (II) in the second veterinarily acceptable carrier are not in fluid communication.

2. The kit of claim 1, wherein the first veterinarily acceptable carrier comprises C1-C10 alcohols or esters thereof, C10-C18 saturated fatty acids or esters thereof, C10-C18 monounsaturated fatty acids or esters thereof, monoesters or diesters of aliphatic diacids, glycerol monoesters, glycerol diesters, glycerol triesters, glycols, glycol ethers, glycol esters, glycol carbonates; or polyethylene glycols, or monoethers, diethers, monoesters or diesters thereof; or a combination thereof.

3. The kit of claim 2, wherein the first veterinarily acceptable carrier comprises a C1-C10 alcohol, a glycol ether, a polyethylene glycol monoether or a polyethylene glycol diether, or a mixture thereof.

4. The kit of claim 1, wherein the first veterinarily acceptable carrier comprises acetone, acetonitrile, benzyl alcohol, ethanol, isopropanol, diisobutyl adipate, diisopropyl adipate, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone, N-methylpyrrolidone, diethylene glycol monoethyl ether, triacetin, butyl acetate, octyl acetate, propylene carbonate, butylene carbonate, dimethyl sulfoxide, dimethylformamide or dimethylacetamide, or any combination thereof.

5. The kit of claim 1, wherein the second veterinarily acceptable carrier comprises aryl ethers, alkoxybenzene compounds, aliphatic carboxylic acid esters, aromatic carboxylic acid esters, aliphatic ketones or cyclic ketones, or mixtures thereof.

6. The kit of claim 1, wherein the second veterinarily acceptable carrier comprises methoxybenzene, butyl acetate, benzyl acetate, methyl isobutyl ketone, ethyl benzoate, benzyl benzoate or octyl acetate, or mixtures thereof.

7. The kit of claim 1, wherein the first veterinarily acceptable carrier further comprises about 1% to about 20% (w/v) of a crystallization inhibitor selected from anionic surfactants, cationic surfactants, an amine salt, non-ionic surfactants, amphoteric surfactants, polyvinylpyrrolidone, polyvinyl alcohols, copolymers of vinyl acetate and of vinylpyrrolidone, N-methylpyrrolidone, dimethylsufoxide, polyethylene glycols, benzyl alcohol, mannitol, glycerol, sorbitol, polyoxyethylenated esters of sorbitan, lecithin, sodium carboxymethylcellulose and polymers derived from acrylic monomers, or a mixture thereof.

8. The kit of claim 7, wherein the crystallization inhibitor comprises polyvinylpyrrolidone, a copolymer of vinyl acetate and vinylpyrrolidone, a polyethylene glycol or a non-ionic surfactant, or a combination thereof.

9. The kit of claim 7, wherein the non-ionic surfactant is a polyoxyethylenated ester of sorbitan, a polyoxyethylenated alkyl ether, polyethylene glycol stearate, a polyoxyethylenated derivative of castor oil, a polyglycerol ester, a polyoxyethylenated fatty alcohol, a polyoxyethylenated fatty acid or a copolymer of ethylene oxide and propylene oxide.

10. The kit of claim 1, wherein the composition further comprises about 0.01 to about 0.05% (w/v) of an antioxidant.

11. The kit of claim 10, wherein the antioxidant is butylated hydroxyanisole, butylated hydroxytoluene, ascorbic acid, sodium metabisulphite, propyl gallate or sodium thiosulfate or a mixture thereof.

12. The kit of claim 1, wherein the 1-arylpyrazole compound is fipronil.

13. The kit of claim 1, wherein the formamidine compound is amitraz.

14. The kit of claim 12, wherein fipronil is present at a concentration of about 5% (w/v) to about 15% (w/v).

15. The kit of claim 13, wherein amitraz is present at a concentration of about 1% (w/v) to about 30% (w/v).

16. The kit of claim 1, wherein the 1-arylpyrazole compound is fipronil; the formamidine compound is amitraz; and wherein fipronil is present in the first veterinarily acceptable carrier at a concentration of about 5% (w/v) to about 15% (w/v) and amitraz is present in the second veterinarily acceptable carrier at a concentration of about 5% (w/v) to about 20% (w/v).

17. The kit of claim 16, wherein the first veterinarily acceptable carrier comprises ethanol, isopropanol, diethyleneglycol monoethyl ether, N-methylpyrrolidone, or a mixture thereof; and the second veterinarily acceptable carrier comprises methoxybenzene, butyl acetate, benzyl acetate, ethyl benzoate, benzyl benzoate or octyl acetate, or a mixture thereof.

18. The kit of claim 17, wherein the second veterinarily acceptable carrier comprises octyl acetate.

19. The kit of claim 17, wherein the first veterinarily acceptable carrier further comprises about 1% to about 20% (w/v) of a crystallization inhibitor selected from non-ionic surfactants, polyvinylpyrrolidone, polyvinyl alcohols, copolymers of vinyl acetate and of vinylpyrrolidone, polyethylene glycols, mannitol, sorbitol, polyoxyethylenated esters of sorbitan, or a mixture thereof.

20. The kit of claim 19, wherein the polyoxyethylenated ester of sorbitan is polysorbate 80.

21. The kit of claim 20, wherein the crystallization inhibitor is a mixture of polyvinylpyrrolidone and a polysorbate 80.

22. The kit of claim 1, wherein the first veterinarily acceptable carrier or the second veterinarily acceptable carrier further comprises an additional parasiticidal active agent.

23. The kit of claim 22, wherein the additional parasiticidal active agent is an avermectin or milbemycin compound, an insect growth regulator, a pyrethroid, a benzimidazole, an imidazothiazole, praziquantel, an isoxazoline compound, an amino acetonitrile compound or an aryloazol-2-yl cyanoethylamino compound.

24. The kit of claim 23, wherein the insect growth regulator is methoprene, pyriproxyfen, hydroprene, cyromazine, fluazuron, lufenuron or novaluron.

25. The kit of claim 23, wherein the avermectin or milbemycin compound is abamectin, dimadectin, doramectin, emamectin, eprinomectin, ivermectin, latidectin, lepimectin, selamectin, milbemectin, milbemycin D, moxidectin, nemadectin or milbemycin oxime.

26. The kit of claim 1, wherein the divider wall has a thickness of about 10% to about 40% of either the front wall or the rear wall.

27. The kit of claim 1, wherein the divider wall has a thickness of about 30% to about 70% of either the front wall or the rear wall.

28. The kit of claim 1, wherein the divider wall has a thickness of about 40% to about 60% of either the front wall or the rear wall.

29. The kit of claim 1, wherein the divider wall comprises a barrier film selected from a flexible monolayer film or a laminate flexible film.

30. The kit of claim 29, wherein the divider wall comprises a material selected from the group consisting of polyester, polypropylene, polyethylene, ethyl vinyl alcohol, ethyl vinyl acetate, polyamide, poly acrylonitrile, fluoropolymer, poly chlorotrifluoroethylene and aluminium foil.

31. The kit of claim 1, wherein the front wall and the rear wall comprise a film selected from a rigid monolayer film or a laminate rigid film.

32. The kit of claim 31, wherein the front wall and the rear wall comprise a material selected from the group consisting of polyethylene terephthalate, amorphous polyethylene terephthalate, polyethylene terephthalate glycol, crystalline polyethylene terephthalate, polyvinyl chloride, polypropylene, polyethylene, polyamide, cycloolefin copolymers, poly acrylonitrile, fluoropolymer and poly chlorotrifluoroethylene.

33. The kit of claim 1, wherein the opening mechanism comprises a fracture line, a die cut or a perforation, or a combination thereof, at one end of the container.

34. The kit of claim 33, wherein the opening mechanism is a die cut.

35. The kit of claim 33, wherein the opening mechanism comprises two half-moon shaped die cuts adjacent to a fracture line.

36. The kit of claim 1, wherein the first and second cavities are formed by a thermoforming process.

37. The kit of claim 1, wherein the divider wall is constructed from a central ribbon and the front and rear walls are constructed from an external ribbon.

38. The kit of claim 1, wherein the front wall, the divider wall and the back wall are coupled along part of their perimeter to define the two cavities by bonding or welding them together.

39. The kit of claim 1, wherein in the compound of formula (IB):
$R_{1b}$ is CN;
$R_{2b}$ is $S(O)_n R_{14b}$;
$R_{14b}$ is haloalkyl;
$R_{3b}$ is $-NR_{7b}R_{8b}$ or alkyl;
$R_{6b}$ is haloalkyl;
$R_{7b}$ and $R_{8b}$ are each independently hydrogen or alkyl;
$R_{4b}$ and $R_{13b}$ are independently halogen; and
Z is C—$R_{13b}$.

40. The kit of claim 1, wherein in the compound of formula (II):
x is 1 or 2;
$R_{14}$ is $C_1$-$C_4$-alkyl, chloro or —OC(=O)NR$_a$R$_b$ where $R_a$ and $R_b$ are independently hydrogen or $C_1$-$C_4$-alkyl;
$R_{15}$ is hydrogen;
$R_{16}$ is $C_1$-$C_4$-alkyl; and
$R_{17}$ is $C_1$-$C_4$-alkyl or

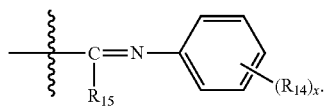

* * * * *